US012497516B2

(12) United States Patent
Bartholomew et al.

(10) Patent No.: US 12,497,516 B2

(45) **Date of Patent: *Dec. 16, 2025**

(54) WATER-SOLUBLE POLYMERIC DYES HAVING PENDANT CHROMOPHORES

(71) Applicant: BECTON, DICKINSON AND COMPANY, Franklin Lakes, NJ (US)

(72) Inventors: Glenn Bartholomew, San Marcos, CA (US); Yongchao Liang, Irvine, CA (US); Brian Wall, Poway, CA (US); David Moureau, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 421 days.

This patent is subject to a terminal disclaimer.

(21) Appl. No.: 18/201,649

(22) Filed: May 24, 2023

(65) Prior Publication Data

US 2023/0295441 A1 Sep. 21, 2023

Related U.S. Application Data

(63) Continuation of application No. 17/531,067, filed on Nov. 19, 2021, now Pat. No. 11,702,547, which is a (Continued)

(51) Int. Cl.
*C09B 69/10* (2006.01)
*G01N 33/58* (2006.01)

(52) U.S. Cl.
CPC ......... *C09B 69/109* (2013.01); *G01N 33/582* (2013.01)

(58) Field of Classification Search
CPC .... C08G 2261/1426; C08G 2261/3243; C08G 2261/124; C08G 2261/414;

(Continued)

(56) References Cited

U.S. PATENT DOCUMENTS 4,689,482 A 8/1987 Kazuo et al.
6,580,739 B1 6/2003 Coldren et al.

(Continued)

FOREIGN PATENT DOCUMENTS

CN 105602276 A 5/2016
JP 2005136365 A 5/2005

(Continued)

OTHER PUBLICATIONS

Liu, B. et al., "Polyacetylenes containing BODIPY pendants with different connectivities: synthesis, characterization and opto-electronic properties", Polymer Chemistry, Sep. 11, 2013, vol. 5, No. 2, pp. 372-381. Abstract Only.

(Continued)

*Primary Examiner* — Shane Fang

(74) *Attorney, Agent, or Firm* — Bret E. Field; BOZICEVIC, FIELD & FRANCIS LLP

(57) ABSTRACT

Water soluble light harvesting multichromophores having pendant chromophore groups are provided. The light harvesting multichromophore has a polymeric backbone including non-conjugated repeat units and a plurality of pendant donor chromophore groups linked to a non-conjugated repeat unit of the polymeric backbone. A pendant chromophore group can be a BODIPY group substituted with one or more water soluble groups. Polymeric tandem dyes based on the subject multichromophores are provided that further include an acceptor fluorophore linked to a non-conjugated repeat unit of the polymeric backbone and configured in energy-receiving proximity to a pendant donor chromophore group. Also provided are labelled specific binding members that include the subject polymeric tandem dyes. Methods of evaluating a sample for a target analyte and methods of labelling a target molecule in which the subject polymeric tandem dyes find use are provided. Sys- (Continued)

tems and kits for practicing the subject methods are also provided.

19 Claims, 10 Drawing Sheets

Specification includes a Sequence Listing.

Related U.S. Application Data continuation of application No. 17/003,591, filed on Aug. 26, 2020, now Pat. No. 11,214,688, which is a continuation of application No. 16/368,513, filed on Mar. 28, 2019, now Pat. No. 10,844,228.

(60) Provisional application No. 62/715,722, filed on Aug. 7, 2018, provisional application No. 62/650,935, filed on Mar. 30, 2018.

(58) Field of Classification Search
CPC ............ C08G 2261/91; H01L 51/0036; H01L 51/0047; H01L 51/4253; Y02E 10/549
See application file for complete search history.

(56) References Cited

U.S. PATENT DOCUMENTS

| | | | |
|---|---|---|---|
| 6,965,103 | B2 | 11/2005 | Shapiro et al. |
| 8,835,000 | B2 | 9/2014 | Natarajan et al. |
| 2002/0190221 | A1 | 12/2002 | Hutchinson et al. |
| 2003/0099999 | A1 | 5/2003 | Wei et al. |
| 2003/0178607 | A1 | 9/2003 | Swager et al. |
| 2004/0175768 | A1 | 9/2004 | Kushon et al. |
| 2007/0127123 | A1 | 6/2007 | Brown et al. |
| 2011/0092666 | A1 | 4/2011 | Liaw |
| 2012/0091437 | A1 | 4/2012 | Le et al. |
| 2014/0273193 | A1 | 9/2014 | Li |
| 2016/0181764 | A1 | 6/2016 | Kanskar et al. |
| 2016/0266131 | A1 | 9/2016 | Liang et al. |
| 2019/0153232 | A1 | 5/2019 | Matray et al. |
| 2019/0203052 | A1 | 7/2019 | Xu et al. |
| 2020/0261602 | A1 | 8/2020 | Desai et al. |

FOREIGN PATENT DOCUMENTS

| | | | |
|---|---|---|---|
| JP | 2014120560 | A | 6/2014 |
| JP | 2018509502 | A | 2/2015 |
| JP | 2015512955 | A | 4/2015 |
| JP | 2015218304 | A | 12/2015 |
| WO | WO2007011630 | A2 | 1/2007 |
| WO | WO2011154405 | A1 | 12/2011 |
| WO | WO2015027176 | A1 | 2/2015 |
| WO | WO2015109136 | A2 | 7/2015 |
| WO | WO2016138457 | A1 | 9/2016 |
| WO | WO2016138461 | A1 | 9/2016 |
| WO | WO2016144652 | A1 | 9/2016 |
| WO | WO2016183185 | A1 | 11/2016 |
| WO | WO2017173348 | A1 | 3/2017 |
| WO | WO2017105927 | A1 | 6/2017 |
| WO | WO2017173355 | A1 | 10/2017 |
| WO | WO2017177065 | A2 | 10/2017 |
| WO | WO2018078066 | A1 | 10/2017 |
| WO | WO2017196954 | A1 | 11/2017 |
| WO | WO2017197144 | A1 | 11/2017 |
| WO | WO2017214165 | A1 | 12/2017 |
| WO | WO2018022925 | A1 | 2/2018 |
| WO | WO2019071153 | A1 | 10/2018 |
| WO | WO2018231805 | A2 | 12/2018 |
| WO | WO2019071208 | A1 | 4/2019 |
| WO | WO2019099789 | A1 | 5/2019 |
| WO | WO2019118714 | A1 | 6/2019 |
| WO | WO2019140128 | A1 | 7/2019 |
| WO | WO2019140227 | A1 | 7/2019 |
| WO | WO2019140301 | A1 | 7/2019 |
| WO | WO2019182765 | A1 | 9/2019 |
| WO | WO2019182766 | A1 | 9/2019 |
| WO | WO2020006285 | A1 | 1/2020 |
| WO | WO2020014634 | A1 | 1/2020 |

OTHER PUBLICATIONS

Thapaliya, et al. "Bioimaging with Macromolecular Probes Incorporating Multiple BODIPY Fluorophores", Bioconjugate Chem. 2017, 28, 5, 1519-1528.

Xia, et al. "Influence of Nanostructure on the Exciton Dynamics of Multichromophore Donor-Acceptor Block Copolymers", ACS Nano 2017, 11, 5, 4593-4598.

or

WATER-SOLUBLE POLYMERIC DYES HAVING PENDANT CHROMOPHORES

CROSS-REFERENCE TO RELATED APPLICATION

Pursuant to 35 U.S.C. § 119(e), this application claims priority to the filing dates of U.S. Provisional Patent Application Ser. No. 62/650,935, filed Mar. 30, 2018, and U.S. Provisional Patent Application Ser. No. 62/715,722, filed Aug. 7, 2018; the disclosures of which applications are incorporated herein by reference.

INCORPORATION BY REFERENCE OF SEQUENCE LISTING PROVIDED AS A SEQUENCE LISTING XML FILE

A Sequence Listing is provided herewith as a Sequence Listing XML, "BECT-152CON3_SEQLIST", created on Oct. 28, 2025 and having a size of 56 bytes. The contents of the Sequence Listing XML are incorporated herein by reference in their entirety.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g. in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

SUMMARY

Water soluble light harvesting multichromophores having a plurality of pendant chromophore groups are provided. The light harvesting multichromophore has a polymeric backbone including non-conjugated repeat units and a plurality of pendant donor chromophore groups each independently linked to a non-conjugated repeat unit of the polymeric backbone. A pendant chromophore group can be a BODIPY group substituted with one or more water soluble groups. Polymeric tandem dyes based on the subject multichromophores are also provided that further include an acceptor fluorophore linked to a non-conjugated repeat unit of the polymeric backbone and configured in energy-receiving proximity to at least one pendant donor chromophore group of the light harvesting multichromophore. Also provided are labelled specific binding members that include the subject polymeric tandem dyes. Methods of evaluating a sample for the presence of a target analyte and methods of labelling a target molecule in which the subject polymeric tandem dyes find use are also provided. Systems and kits for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
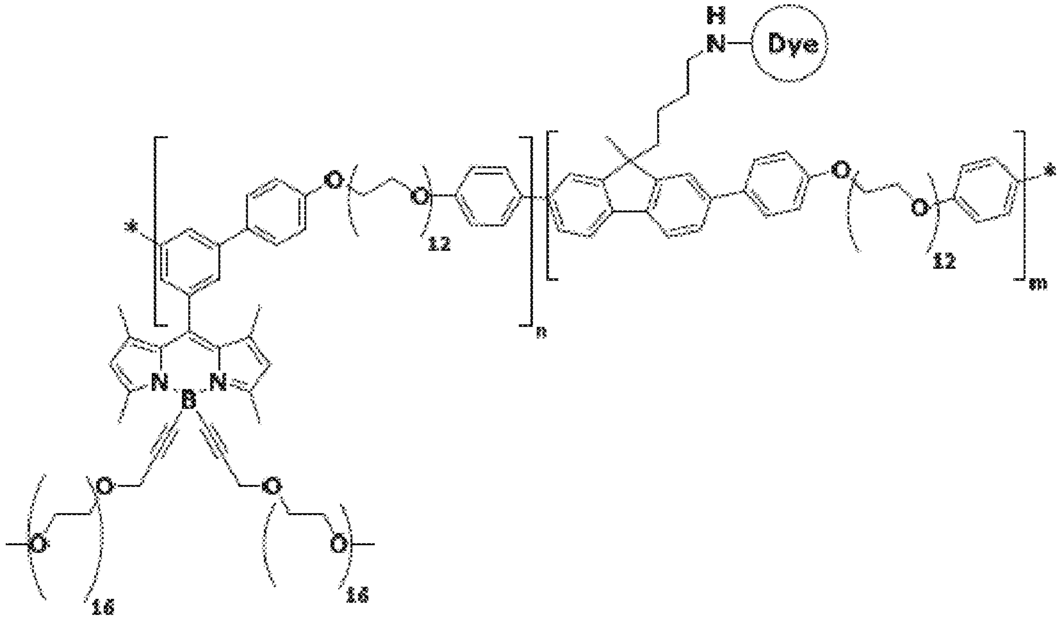
FIG. 1 depicts the general structure of an exemplary polymeric tandem dye where the "Dye" is an acceptor fluorophore.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a dye" refers to one or more dyes, i.e., a single dye and multiple dyes. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), tetrazine, transcyclooctene, dienes and dienophiles, and azide, sulfur(VI) fluoride exchange chemistry (SuFEX), sulfonyl fluoride, as well as hydroxyl, hydrazido, hydrazino, aldehyde, ketone, azido, alkyne, phosphine, epoxide, and the like.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

The term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 5 or more, such as 6 or more, 7 or more, 8 or more, 9 or more, 10 or more, 20 or more, 30 or more, 40 or more, 50 or more, 60 or more, 70 or more, 80 or more, 90 or more, 100 or more, 300 or more, 1000 or more, 3000 or more, 10,000 or more, 100,000 or more members.

Numeric ranges are inclusive of the numbers defining the range.

The term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$ M, at least $10^{-9}$ M, such as up to $10^{-10}$ M.

"Affinity" refers to the strength of binding, increased binding affinity being correlated with a lower Kd.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

The term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The terms "polyethylene oxide", "PEO", "polyethylene glycol" and "PEG" are used interchangeably and refer to a polymeric group including a chain described by the formula $-(CH_2-CH_2-O-)_n-$ or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

The term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, a lower alkyl group includes from 1 to 6 carbon atoms, such as from 1 to 4 carbon atoms. This term includes, by way of example, linear and branched hydrocarbyl groups such as methyl ($CH_3-$), ethyl ($CH_3CH_2-$), n-propyl ($CH_3CH_2CH_2-$), isopropyl ($(CH_3)_2CH-$), n-butyl ($CH_3CH_2CH_2CH_2-$), isobutyl ($(CH_3)_2CHCH_2-$), sec-butyl ($(CH_3)(CH_3CH_2)CH-$), t-butyl ($(CH_3)_3C-$), n-pentyl ($CH_3CH_2CH_2CH_2CH_2-$), and neopentyl ($(CH_3)_3CCH_2-$).

The term "substituted alkyl" refers to an alkyl group as defined herein wherein one or more carbon atoms in the alkyl chain have been optionally replaced with a heteroatom such as —O—, —N—, —S—, $-S(O)_n-$ (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, $-SO_2$-alkyl, $-SO_2$-aryl, $-SO_2$-heteroaryl, and $-NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl ($-C\equiv CH$), and propargyl ($-CH_2C\equiv CH$).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, $-SO_2$-alkyl, $-SO_2$-substituted alkyl, $-SO_2$-aryl, and $-SO_2$-heteroaryl.

"Amino" refers to the group $-NH_2$. The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Substituted aryl", unless otherwise constrained by the definition for the aryl substituent, refers to an aryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Substituted heteroaryl", unless otherwise constrained by the definition for the substituent, refers to an heteroaryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —$NR^{10}$—, —$NR^{10}C(O)$—, —$C(O)NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —O $P(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Other definitions of terms may appear throughout the specification.

DETAILED DESCRIPTION

As summarized above, water soluble light harvesting multichromophores having a plurality of pendant chromophore groups are provided. The light harvesting multichromophore has a polymeric backbone including non-conjugated repeat units and a plurality of pendant donor chromophore groups each independently linked to a non-conjugated repeat unit of the polymeric backbone. A pendant chromophore group can be a BODIPY group substituted with one or more water soluble groups. Polymeric tandem dyes based on the subject multichromophores are also provided that further include an acceptor fluorophore linked to a non-conjugated repeat unit of the polymeric backbone and configured in energy-receiving proximity to at least one pendant donor chromophore group of the light harvesting multichromophore. Also provided are labelled specific binding members that include the subject polymeric tandem dyes. Methods of evaluating a sample for the presence of a target analyte and methods of labelling a target molecule in which the subject polymeric tandem dyes find use are also provided. Systems and kits for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms “a”, “an”, and “the” include plural referents unless the context clearly dictates otherwise. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of “means” or “steps” limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing the subject invention, light harvesting multichromophores and related polymeric tandem dyes including an acceptor fluorophore are described first in greater detail. Next, labelled specific binding members which include the subject polymeric tandem dyes are described. Then, methods of interest in which the subject polymeric tandem dyes find use are reviewed. Systems and kits that may be used in practicing methods of the present disclosure are also described.

Light Harvesting Multichromophores

As summarized above, the present disclosure includes a light harvesting multichromophore having a modular scaffold to which pendant light-absorbing chromophore groups are attached. The term “pendant group” refers to a sidechain group that is connected to the backbone of the modular scaffold but which is not part of the backbone. In contrast to the light absorbing co-monomers of conjugated polymer dyes, the pendant light-absorbing chromophore groups of the subject multichromophores are not pi-conjugated to each other and do not form a delocalized pi-electron system. Rather, the modular scaffold of the subject multichromophores provides for the configuration of a plurality of light-absorbing chromophore groups in a compact area sufficient for efficient energy transfer between the chromophores (see e.g., FIG. 6A), and when present, to an acceptor fluorophore (see e.g., FIG. 6B). Taken together this configuration of pendant light-absorbing chromophore groups forms a light harvesting multichromophore having an absorption wavelength (e.g., as described herein) at which the optically active chromophore groups absorb light to form an excited state. As such, the light-absorbing chromophore groups are configured in energy-receiving proximity to each other and are capable of donating energy to an acceptor fluorophore when present.

The terms “light harvesting multichromophore” and “polymeric dye” are used interchangeably and refer to a polymer of the present disclosure which has a plurality of pendant chromophore groups capable of harvesting light with a particular absorption maximum wavelength and converting it to emitted light at a longer emission maximum wavelength. The polymer can have a backbone which is saturated or partially unsaturated.

Further pendant groups such as acceptor fluorophores, secondary donor chromophores, linkers and chemoselective tags capable of biomolecule conjugation and water solubilizing groups can also be attached to the modular scaffold. In some cases, an acceptor fluorophore can be installed in conjunction with two types of donor chromophores (a primary and a secondary donor chromophore) to provide for a desired fluorescent emission from the acceptor fluorophore. The number and positioning of acceptor fluorophores relative to the configuration of pendant donor chromophores can be controlled.

A particular configuration of pendant groups can be determined and controlled by the arrangement of the repeat units of the underlying modular scaffold to which the pendant groups are attached. The subject multichromophores can include a plurality of water solubilizing groups attached to the scaffold and/or the pendant groups at any convenient locations to provide a water soluble light harvesting multichromophore. The modular scaffold can be composed of repeat units which form a polymeric backbone having sidechains groups to which the pendant groups can be attached. The repeat units can be arranged in a variety of configurations to provide for a water soluble light harvesting multichromophore having desirable spectroscopic properties. The distances and arrangement between sites for covalent attachment of the pendant donor chromophores and the acceptor fluorophore (when present) can be controlled to provide for desirable energy transfer processes. This can lead to desirable high light harvesting and signal amplification properties.

Figure 6A:
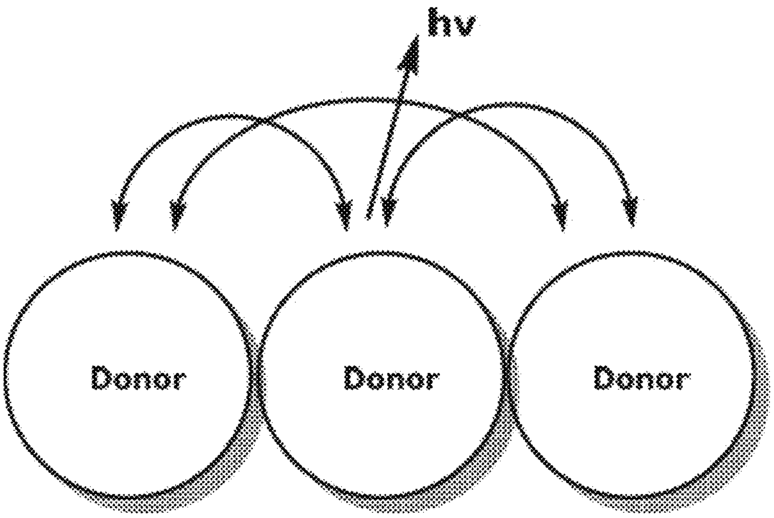
FIG. 6A illustrates homo-energy transfer between pendant donor chromophores which leads preferentially to continued reversible energy transfer amongst equal chromophores rather than emission from a single chromophore. This process can result in self-quenching and quantum yields that are significantly lower than those observed for a single isolated chromophore.
Figure 6B:
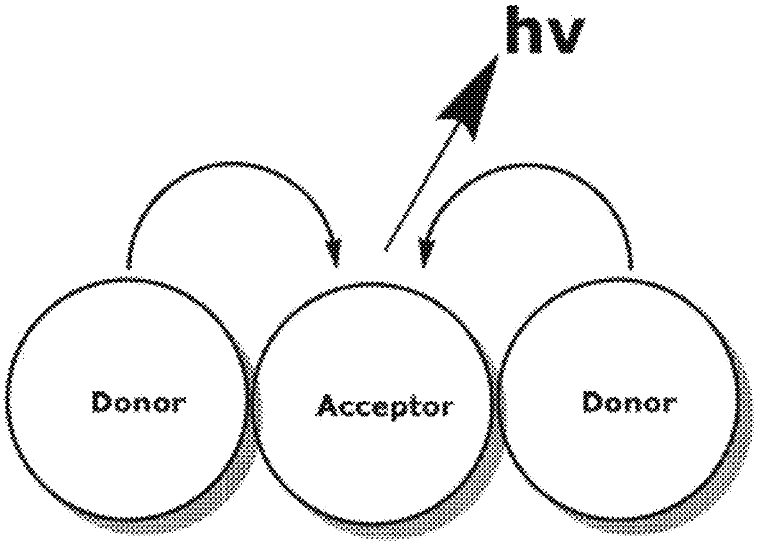
FIG. 6B illustrates hetero-energy transfer which leads to primarily one way energy transfer between different chromophores. Energy transfer to the secondary chromophore leads preferentially to emission, limited by the quantum yield of the acceptor and a single donor chromophore.

As depicted in FIG. 6A, the configuration of pendant donor chromophore groups can exhibit, upon excitation with incident light, self-quenching of fluorescence relative to an unquenched isolated donor chromophore group. By self-quenching is meant that 10% or more, such as 20% or more, 25% or more, 30% or more, 40% or more, or 50% or more of the fluorescence relative to unquenched isolated donor chromophore groups.

The modular scaffold can be composed of a polymeric backbone of non-conjugated repeat units having any convenient configuration, such as a linear, branched or dendrimer configuration. The polymeric backbone can be a linear polymer. The polymeric backbone can be branched. In some instances, the light harvesting multichromophore includes a plurality of pendant donor chromophore groups each independently linked to a non-conjugated repeat unit of the polymeric backbone. The configuration of pendant groups can be installed during or after synthesis of the polymeric backbone. The incorporation of pendant groups can be with achieved with a random configuration, a block configuration, or in a sequence-specific manner via stepwise synthesis, depending on the particular method of synthesis utilized.

The term “unit” refers to a structural subunit of a polymer. The term unit is meant to include monomers, co-monomers, co-blocks, repeating units, and the like. A “repeating unit” or “repeat unit” is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer, a random arrangement of units or a defined sequence, each block may define a distinct repeating unit. It is understood that a variety of arrangements of repeating units or blocks are possible and that in the depicted formula of the subject multichromophores described herein any convenient linear arrangements of various lengths can be included within the structure of the overall polymer. It is understood that the polymer may also be represented by a formula in terms of mol % values of each unit in the polymer and that such formula may represent a variety of arrangements of repeat unit, such as random or multiblock polymer or a defined sequence of residues. In some cases, a repeating unit of the polymer includes a single monomer group. In certain instances, a repeating unit of the polymer includes two or more monomer groups, i.e., co-monomer groups, such as two, three, four or more co-monomer groups. The term "co-monomer" or "co-monomer group" refers to a structural unit of a polymer that may itself be part of a repeating unit of the polymer.

The light harvesting multichromophore includes a modular scaffold that has a linear polymeric backbone of non-conjugated repeat units. The modular scaffold can have a polymeric backbone including a random configuration of non-conjugated repeat units. The modular scaffold can have a polymeric backbone including a block or co-block configuration of non-conjugated repeat units. Alternatively, the modular scaffold can have a polymeric backbone including a particular defined sequence of non-conjugated repeat units, e.g., amino acid residues of a polypeptide sequence. These configurations can be characterized by polymeric segments of repeat units (e.g., as described herein), which segments can themselves be repeated throughout the modular scaffold.

By "non-conjugated" is meant that at least a portion of the repeat unit includes a saturated backbone group (e.g., a group having two or more consecutive single covalent bonds) which precludes pi conjugation or an extended delocalized electronic structure along the polymeric backbone from one repeat unit to the next. It is understood that even though one repeat unit may not be conjugated to an adjacent repeat unit, such a repeat unit may include one or more isolated unsaturated groups including an unsaturated bond (e.g., of an alkenylene group or an alkynylene group) and/or an aryl or heteroaryl group, which groups can be a part of the backbone. In some cases, each repeat unit of the polymeric backbone includes one sidechain including a linked pendant group or a chemoselective tag for linking to a pendant group.

In some instances, the multichromophore includes a segment of the formula (I):

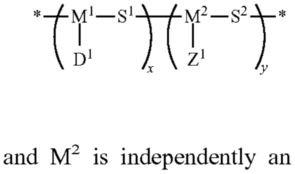
(I)

wherein:

each $M^1$ and $M^2$ is independently an unsaturated co-monomer;

each $S^1$ and $S^2$ is independently a non-conjugated spacer unit;

each $D^1$ is independently a pendant light absorbing chromophore (e.g., as described herein) linked to $M^1$;

each $Z^1$ is independently a chemoselective tag linked to $M^2$;

x is 75 mol % or more; and y is 25 mol % or less, where * is a connection to the polymeric backbone of the multichromophore.

In some cases of formula (I), $M^1$ and $S^1$ form a first repeat unit ($M^1$-$S^1$) and $M^2$ and $S^2$ form a second repeat unit ($M^2$-$S^2$) of the polymeric backbone. The first and second repeat units can be arranged in a random or co-block configuration. In the first repeat units, $D^1$ can be linked to $M^1$ via conjugation of a first chemoselective tag to a $D^1$ precursor. In the second repeat units, the $Z^1$ groups can be further conjugated to a molecule of interest via a second chemoselective tag ($Z^2$) to install a pendant group, such as a second light absorbing chromophore, an acceptor fluorophore or a linked biomolecule (e.g., as described herein). In certain cases of formula (I), the $D^1$ pendant groups of the first repeat units include two or more (e.g., two or three) distinct types of pendant light harvesting chromophores that together provide a light harvesting multichromophore system. In certain instances of formula (I), the $D^1$ pendant groups of the first repeat units are all the same.

In some instances of formula (I), x is 80 mol % or more, such as 85 mol % or more, 90 mol % or more, 95 mol % or more, 96 mol % or more, 97 mol % or more, 98 mol % or more, or 99 mol % or more. In some instances of formula (I), y is 20 mol % or less, such as 15 mol % or less, 10 mol % or less, 5 mol % or less, 4 mol % or less, 3 mol % or less, 2 mol % or less, 1 mol % or less.

Any convenient unsaturated co-monomers can be utilized as $M^1$ and $M^2$ groups in the subject multichromophores, e.g., of formula (I). By unsaturated co-monomer is meant a co-monomer having at least one unsaturated covalent bond in the polymeric backbone. Unsaturated co-monomers of interest include, but are not limited to, aryl or heteroaryl co-monomers, alkynyl co-monomers (e.g., ethynylene) or segments and alkenyl co-monomers (e.g., vinylene) or segments. Aryl or heteroaryl co-monomers of interest which find use in the multichromophores (e.g., of formula (I)) include, but are not limited to, phenyl co-monomers, biphenyl co-monomers, benzooxazole co-monomers, benzothiazole co-monomers, poly-phenylene co-monomers, and fused tricyclic co-monomers, such as fluorene co-monomers, carbazole co-monomers, silole co-monomers and bridged biphenyl co-monomers. The aryl or heteroaryl co-monomers may be optionally further substituted, e.g., as described herein. In some cases of formula (I), each $M^1$ and $M^2$ independently includes one or more groups selected from fluorene, carbazole, silole, biphenylene and phenylene.

The light harvesting multichromophore of formula (I) includes a polymeric backbone of non-conjugated repeat units where each $S^1$ and $S^2$ is independently a saturated spacer unit that precludes pi-conjugation from between adjacent $M^1$ and/or $M^2$ co-monomers. In some cases, $S^1$ and $S^2$ are independently selected from a divalent polyethylene glycol (PEG) and a divalent modified PEG group. By divalent is meant a PEG or modified PEG linker that connects two adjacent co-monomers. In certain instances, the PEG or modified PEG includes 3 to 100 polyethylene glycol units, such as 6 to 100 units (e.g., $PEG_6$ to $PEG_{100}$).

In some instances, the multichromophore includes a segment of the formula (II):

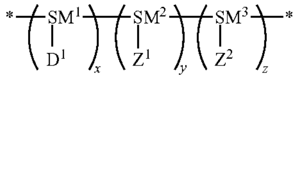
(II)

wherein:

the polymeric backbone of non-conjugated repeat units comprises $SM^1$, $SM^2$ and $SM^3$ co-monomers that are each independently a non-conjugated co-monomer;

each $D^1$ is independently a pendant light absorbing chromophore linked to $SM^1$;

each $Z^1$ is independently a chemoselective tag linked to $SM^2$;

each $Z^2$ is an optional sidechain group linked to $SM^3$;

x is 50 mol % or more; and y+z is 50 mol % or less, where * is a connection to the polymeric backbone of the multichromophore.

$Z^2$ can be absent or any convenient sidechain group, such as a light absorbing chromophore, a chemoselective tag, a linker, a linked biomolecule, a acceptor fluorophore, a WSG, etc. In certain cases of formula (II), $SM^3$ is a spacer co-monomer where $Z^2$ is absent. In certain instances of formula (II), $SM^3$ is a co-monomer including a $Z^2$ group that is a second pendant light absorbing chromophore, where each $D^1$ and each $Z^2$ together provide a light harvesting multichromophore system. In some cases, $SM^3$ is a co-monomer including a second chemoselective tag ($Z^2$), e.g., a protected functional group or a tag that is orthogonal to $Z^1$ that provides for the selective installation of a moiety of interest.

In certain cases of formula (II), x is 60 mol % or more, such as 65 mol % or more, 70 mol % or more, 75 mol % or more, 80 mol % or more, 85 mol % or more, 90 mol % or more, 95 mol % or more, or even more. In certain instances of formula (II), y+z is 40 mol % or less, such as 30 mol % or less, 25 mol % or less, 20 mol % or less, 15 mol % or less, 10 mol % or less, 5 mol % or less, or even less. In certain instances of formula (II), y is at least 1 mol % and 25 mol % or less, such as 20 mol % or less, 15 mol % or less, 10 mol % or less, 5 mol % or less, or even less. In certain instances of formula (II), z is at least 1 mol % and 10 mol % or less, such as 5 mol % or less, or even less.

In certain instances of formula (II), $SM^3$ is absent, i.e., z is 0 mol %. As such, the multichromophore can include a segment of the formula (III):

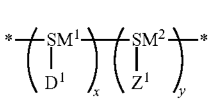

(III)

wherein:

the polymeric backbone of non-conjugated repeat units comprises $SM^1$ and $SM^2$ co-monomers that are each independently a non-conjugated co-monomer;

each $D^1$ is independently a pendant light absorbing chromophore linked to $SM^1$;

each $Z^1$ is independently a chemoselective tag linked to $SM^2$;

x is 75 mol % or more; and y is 25 mol % or less, where * is a connection to the polymeric backbone of the multichromophore.

In certain embodiments of formula (III), $SM^1$ and $SM^2$ are each independently a saturated non-conjugated co-monomer, e.g., a co-monomer providing only single covalent C—C bonds. In some embodiments of formula (III), $SM^1$ and $SM^2$ are each independently a partially saturated non-conjugated co-monomer, e.g., a co-monomer providing an isolated double C═C covalent bond in a backbone of saturated covalent bonds. The first and second repeat units ($SM^1$ and $SM^2$) of formula (III) can be arranged in a random configuration, a block or co-block configuration, or in a particular sequence. In the first repeat units, $D^1$ can be linked to $SM^1$ via conjugation of a first chemoselective tag to a $D^1$ precursor. In the second repeat units ($SM^2$), the $Z^1$ groups can be further conjugated to a molecule of interest via a second chemoselective tag ($Z^2$) to install a pendant group, such as a second light harvesting chromophore, an acceptor fluorophore or a linked biomolecule (e.g., as described herein). In certain cases of formula (III), the $D^1$ pendant groups of the first repeat units include two or more (e.g., two or three) distinct types of pendant light absorbing chromophores that together provide a light harvesting multichromophore system. In certain instances of formula (III), the $D^1$ pendant groups of the first repeat units are all the same.

In some instances of formula (III), x is 80 mol % or more, such as 85 mol % or more, 90 mol % or more, 95 mol % or more, 96 mol % or more, 97 mol % or more, 98 mol % or more, or 99 mol % or more. In some instances of formula (III), y is 20 mol % or less, such as 15 mol % or less, 10 mol % or less, 5 mol % or less, 4 mol % or less, 3 mol % or less, 2 mol % or less, 1 mol % or less.

Any convenient co-monomers can be utilized to provide a polymeric backbone in the multichromophore of formula (II) or (III). Co-monomers of interest which find use in preparing fully saturated or partially saturated polymeric backbones include, but are not limited to, co-monomers derived from an acrylate, a methacrylate, an acrylamide, a polystyrene, a ROMP (ring-opening metathesis polymerization) monomer, an ADMET (acyclic diene metathesis) monomer, a cyclic carbonate, monomers derived from polyethylene glycol and monomers derived from polyethylenimine. The co-monomers can be optionally substituted, e.g., with a chemoselective tag. Co-monomers can be polymerized or linked using any convenient chemistries, including but not limited, alkene polymerization, ring-opening polymerization, radical polymerization and Click chemistry or conjugations between compatible chemoselective functional groups or tags. ADMET monomers of interest include, but are not limited to those described by Mutlu et al. ("Acyclic diene metathesis: a versatile tool for the construction of defined polymer architectures", Chem. Soc. Rev., 2011, 40, 1404-1445). In some instances, $SM^1$, $SM^2$ and/or $SM^3$ has the following formula:

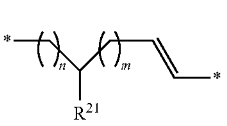

wherein:

$R^{21}$ is $-L^1-D^1$ or $-L^2-Z^1$, where $D^1$ is a pendant donor chromophore, $Z^1$ is a chemoselective tag and $L^1$ and $L^2$ are optional linkers;

n and m are independently an integer from 1 to 6 (e.g., 1 or 2); and

* is a connection to the polymeric backbone of the multichromophore.

ROMP monomers of interest include, but are not limited to, those described by Song et al. ("Scope of the Ring-Opening Metathesis Polymerization (ROMP) Reaction of 1-Substituted Cyclobutenes", J. Am. Chem. Soc., 2010, 132 (30), pp 10513-10520). In some instances, $SM^1$, $SM^2$ and/or $SM^3$ has one of the following formulae:

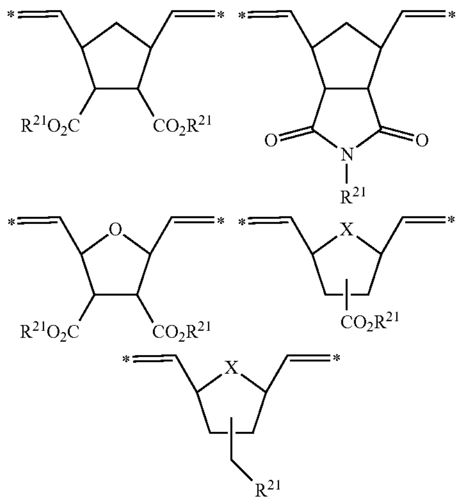

wherein:

$R^{21}$ is $-L^1-D^1$ or $-L^2-Z^1$, where $D^1$ is a pendant donor chromophore, $Z^1$ is a chemoselective tag and $L^1$ and $L^2$ are optional linkers;

X is $CH_2$ or O; and

* is a connection to the polymeric backbone of the multichromophore.

In some instances, $SM^1$, $SM^2$ and/or $SM^3$ include one of the following formulae:

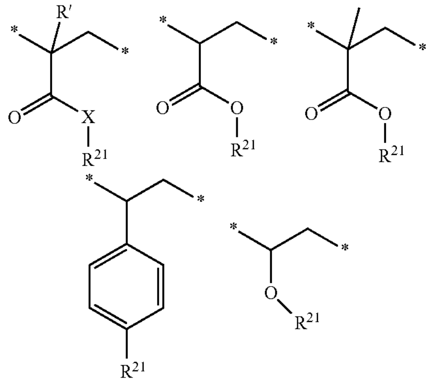

wherein:

$R^{21}$ is $-L^1-D^1$ or $-L^2-Z^1$;

$D^1$ is a pendant donor chromophore;

$Z^1$ is a chemoselective tag;

$L^1$ and $L^2$ are optional linkers;

X is O or NR";

R' is H or lower alkyl (e.g., methyl);

R" is H, lower alkyl, substituted lower alkyl and WSG; and

* is a connection to the polymeric backbone of the multichromophore. In some instances, the polymeric backbone includes a mixture of polystyrene and acrylate or acrylamide-derived co-monomers (e.g., as described herein).

The multichromophore can have a hydrocarbon backbone prepared using any convenient polymerization methods. In some cases, the hydrocarbon backbone is derived from acrylate, acrylamide or styrene co-monomers, or a derivative thereof. In some cases, the multichromophore is described by formula (X):

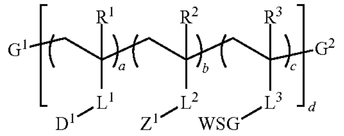

(X)

wherein:

each $D^1$ is independently a pendant donor chromophore;

each $Z^1$ is a chemoselective tag (e.g., as described herein);

each $L^1$, $L^2$ and $L^3$ is independently a linker;

a, b and c are mol % values for each co-monomer;

d represents the total polymerization or average length of the polymer (e.g., d is 2-1000, such as 2-500, 2-200, 2-100 or 2-50);

WSG is a water solubilizing group (e.g., as described herein); and $G^1$ and $G^2$ are each independently selected from terminal group, polymer segment, donor chromophore group, acceptor fluorophore, linker and a linked specific binding member. In some instances of formula (X), c=0. In some instances of formula (X), a>0 and b>0. In some instances of formula (X), a is 80 mol % or more, such as 85 mol % or more, 90 mol % or more, 95 mol % or more, 96 mol % or more, 97 mol % or more, 98 mol % or more, or 99 mol % or more. In some instances of formula (X), b is 20 mol % or less, such as 15 mol % or less, 10 mol % or less, 5 mol % or less, 4 mol % or less, 3 mol % or less, 2 mol % or less, 1 mol % or less. In some instances of formula (X), a is 65-95 mol %, b is 5-35 mol % and c is 0-30 mol %, where a+b+c=100%. In certain instances of formula (X), $L^1$-$L^3$ includes a linkage to the backbone of the polymer selected from: —COO—, —CONR"—, -Ph-, —O—, where R" is H, lower alkyl, substituted lower alkyl or WSG. Such linkages cam be utilized to connect $D^1$, $Z^1$ and WSG to the polymer backbone.

In certain instances of formula (X), $L^1$-$D^1$ is described by one of the following:

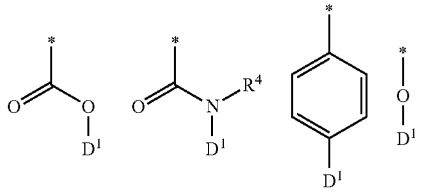

where $R^4$ is H, lower alkyl, substituted lower alkyl or WSG. In certain instances of formula (X), the WSG is a water solubilizing group as described in any one of the embodiments and structures of such groups described herein.

Figure 7A:
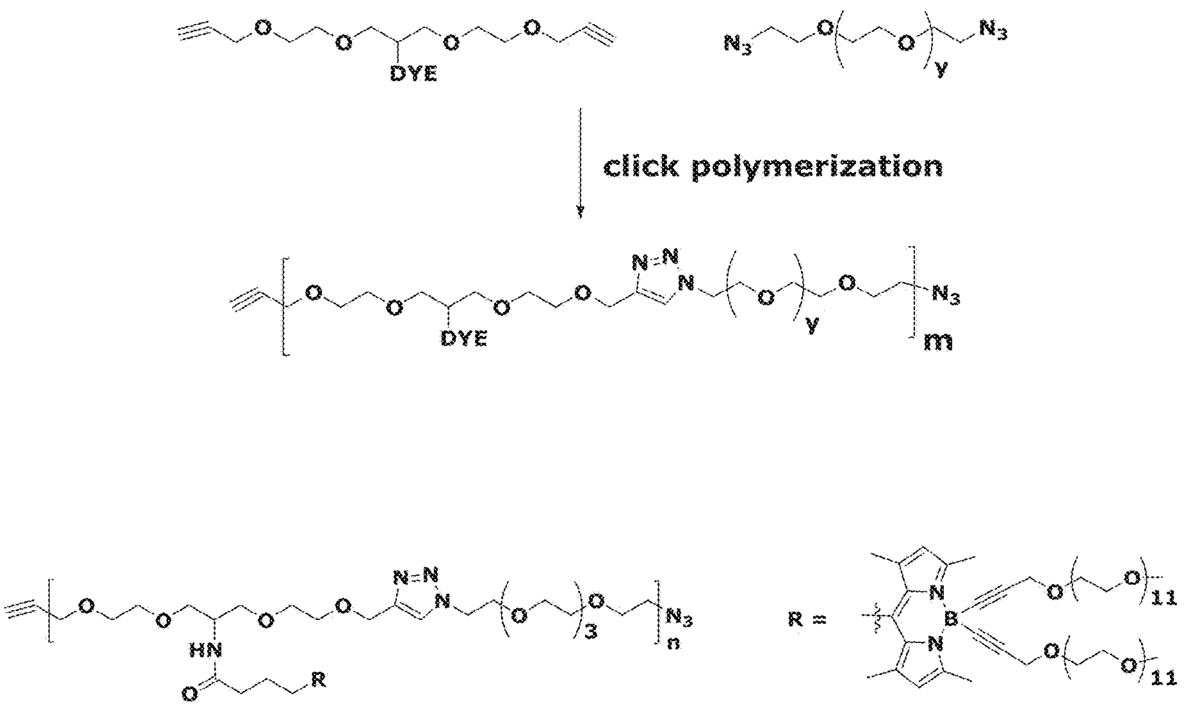
FIG. 7A-7B illustrate synthetic schemes for the preparation of exemplary multichromophores having a linked BODIPY dye ("Dye") (FIG. 7A) and polymeric tandem dye (FIG. 7B) using click polymerization methods. "Dye" and "Donor" can refer to a donor dye such as a BODIPY and "Acceptor" is an acceptor fluorophore.
Figure 7B:
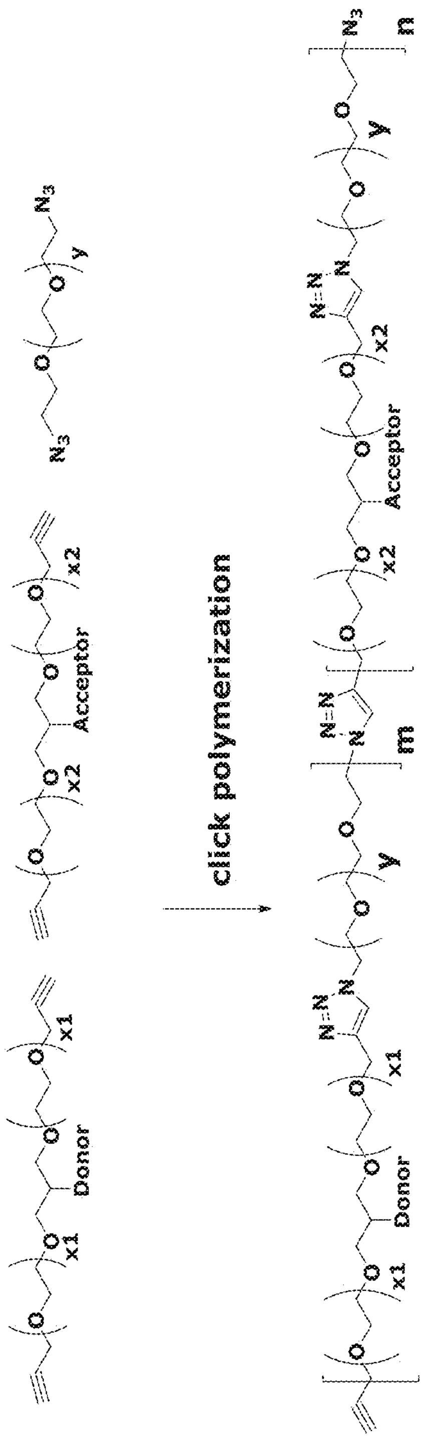

The multichromophore can have a backbone derived from co-monomers connected via linkages or groups that are derived from Click chemistry conjugation reactions (e.g., as described herein). Any convenient divalent co-monomer groups can be derivatized with terminal chemoselective tags and polymerized via conjugation of compatible chemoselective tag. FIGS. 7A and 7B illustrate exemplary schemes for polymerization of co-monomers having alkyne and azide chemoselective tags via Click chemistry. In some cases, the co-monomers include one or more ethyleneoxide or ethyleneamino groups that make up part of the backbone of the polymer. Such groups can provide for desirable water solubility of the resulting polymeric dye. The co-monomer can further include a trivalent unit for linking to a sidechain group such as a donor or acceptor dye or a WSG. In some cases, the co-monomer includes a propyleneoxide or propyleneamino group in the backbone which is further substituted at the 2-position with a sidechain group or substituent. This group can include a linked chemoselective tag, linked donor or acceptor dye, or a linked WSG.

In some instances of formula (II), the multichromophore is of formula (XXI):

(XXI)

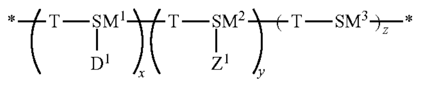

wherein:

- the polymeric backbone of non-conjugated repeat units comprises $SM^1$, $SM^2$ and $SM^3$ co-monomers that are each linked via a group T that is the product of a click chemistry or chemoselective group conjugation reaction (e.g., an azide-alkyne click chemistry);
- $SM^3$ optionally comprises a linked WSG;
- each $D^1$ is independently a pendant light absorbing chromophore linked to $SM^1$;
- each $Z^1$ is independently a chemoselective tag linked to $SM^2$;
- each $Z^2$ is an optional sidechain group linked to $SM^3$;
- x is 50 mol % or more; and
- y+z is 50 mol % or less, where * is a connection to the polymeric backbone of the multichromophore or a terminal group, e.g., as described herein. In certain instances of formula (XXI), $SM^1$, $SM^2$ and $SM^3$ comprise repeating units selected from ethylene oxide, ethylenamino, 2-substituted propyleneoxide and 2-substituted propyleneamino. In some instances of formula (II), each T is 1,4-substituted 1,2,3-triazole, i.e., the product of azide-alkyne click chemistry conjugation reaction.

In some instances of formula (XXII), $SM^1$, $SM^2$ and $SM^3$ have the following structures:

$SM^1$

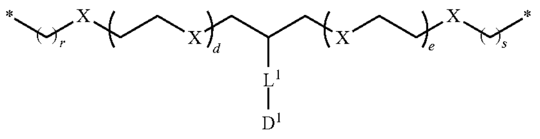

-continued $SM^2$

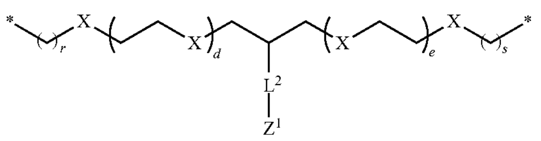

$SM^3$

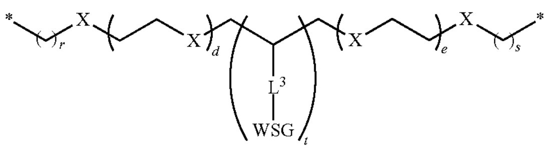

wherein:

- each X is independently O or $NR^{31}$ wherein $R^{31}$ is H, alkyl, substituted alkyl, alkanoyl or substituted alkanoyl;
- each r and s is independently 1-6 (e.g., 1, 2 or 3);
- each d and e is independently 1-12 (e.g., 1-6, such as 1, 2, 3, 4, 5 or 6);
- t is 0 or 1;
- $D^1$ is a pendant donor chromophore;
- $Z^1$ is a chemoselective tag (e.g., as described herein);
- WSG is a water solubilizing group (e.g., as described herein);
- each $L^1$, $L^2$ and $L^3$ is independently a linker; and
- * is a connection to a 1,4-substituted 1,2,3-triazole (T).

It is understood that for any of the co-monomers from which the structures of $SM^1$-$SM^3$ described above are derived, either an azide or an alkyne group may be utilized at the terminal of the co-monomer for linking during polymerization. As such, the 1,4-substituted 1,2,3-triazole (T) may be present in one of two possible orientations as follows:

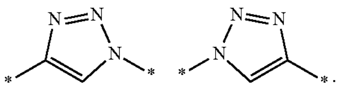

The terminals of the polymeric backbone can include any convenient terminal groups, such as an azide or alkyne group, linker or linked specific binding moiety.

Exemplary multichromophore structures and precursors thereof are shown in Example 3 of the experimental section and in the following structures:

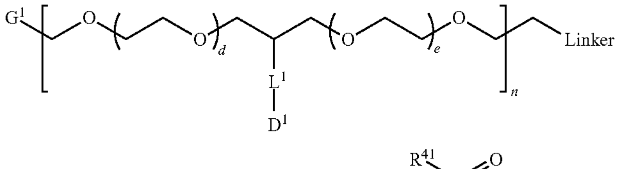

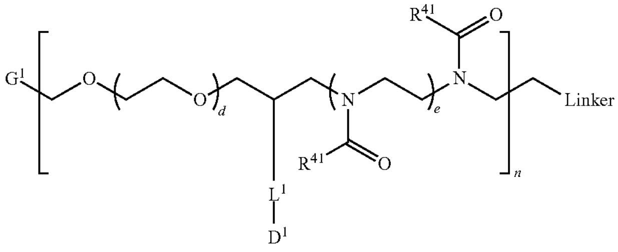

-continued

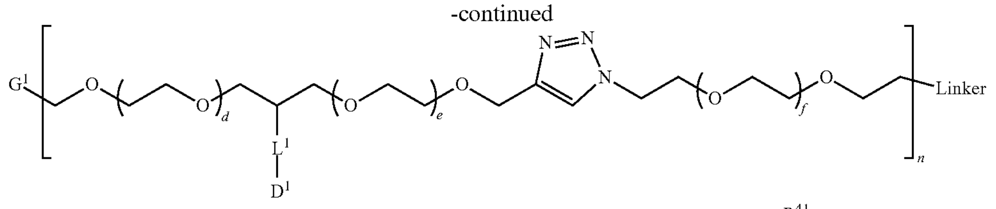

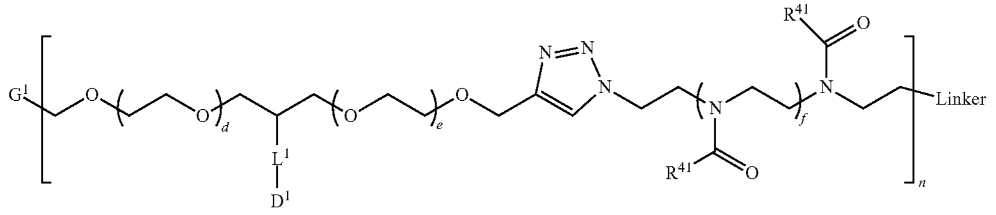

wherein:

$G^1$ is a terminal group (e.g., as described herein);

$L^1$ and $L^2$ are independently a linker;

$D^1$ is a pendant chromophore (e.g., as described herein);

each d, e and f is independently 1-6;

n is 1-1000 (e.g., 2-1000, 2-500, 2-100 or 2-50);

each $R^{41}$ is selected from alkyl, substituted alkyl and WSG; and

"Linker" is a linker including an optional chemoselective functional group, e.g., for conjugation to a co-monomer or a biomolecule. In some instances of formula (XXI), $L^1$-$L^3$ comprise a linkage to the backbone of the polymer selected from —NHCO-alkyl.

Cyclic carbonate and protected carbonate monomers of interest which can be adapted for use in preparing polymeric backbones of the subject multichromophores (see e.g., formula (IX) as described herein) includes, but are not limited to, those described by Barnes et al. in WO2013036532, Cooley et al. (J. Am. Chem. Soc., 131, 45, 1640-3, 2009), and Rothbard et al. in U.S. Pat. No. 7,169,814. Such monomers are utilized in a polymerization reaction using an initiator and a suitable feed ratio of cyclic carbonate monomers to provide a polymeric backbone. Alternative, protected carbonate monomers can be assembled in a step wise synthesis to provide a defined sequence. In some cases of formulae (II)-(III), the polymeric backbone has a polycarbonate backbone. As such, the multichromophore can have formula (IX):

(IX)

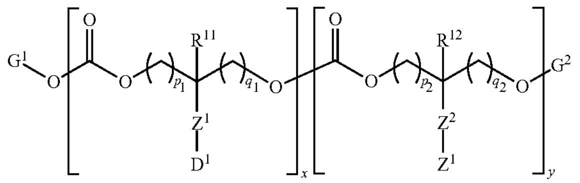

wherein:

each $D^1$ is independently a pendant donor chromophore group;

each $Z^1$ is independently a chemoselective tag;

each $L^1$ and $L^2$ is independently a linker;

x is 75 mol % or more;

y is 25 mol % or less; and $G^1$ and $G^2$ are each independently selected from the group consisting of a terminal group, a polymer segment, a donor chromophore group, an acceptor fluorophore, a linker and a linked specific binding member.

In certain embodiments, the repeat units ($SM^1$, $SM^2$ and/or $SM^3$) of formulae (II)-(III) are arranged in a defined linear sequence. Any convenient co-monomers which can be polymerized in a defined stepwise fashion can be utilized in constructing a multichromophore of formulae (II)-(III). Co-monomers can be derived from amino acids, peptoid monomers, or a protected or cyclic carbonate monomer.

In some cases of formulae (II)-(III), the polymeric backbone is a polypeptide having a defined sequence of α-amino acid residues and/or β-amino acid residues. Two types of β-amino acids and polypeptides can find use in the polymeric backbones of subject multichromophores: those with the sidechain group next to the amine are called β3-peptides/residues and those with the sidechain group next to the carbonyl group are called β2-peptides/residues. In certain embodiments, the multichromophore is of the formula (IV):

(IV)

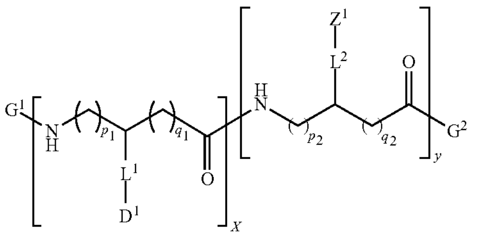

wherein:

each $D^1$ is independently a pendant light absorbing chromophore group;

each $Z^1$ is independently a chemoselective tag;

each $L^1$ and $L^2$ are independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ and $G^2$ are each independently selected from a terminal group, a polymer segment, a light absorbing (e.g., donor) chromophore group, an acceptor fluorophore, a linker and a linked specific binding member.

In some embodiments of formula (IV), $p_1$ and $p_2$ are each 0 and $q_1$ and $q_2$ are each 1 (e.g., β3-amino acid residues). In some embodiments of formula (IV), $p_1$ and $p_2$ are each 1 and $q_1$ and $q_2$ are each 0 (e.g., β2-amino acid residues). In some cases, $p_1$, $p_2$, $q_1$ and $q_2$ are each 0 and the multichromophore is of formula (V):

(V)

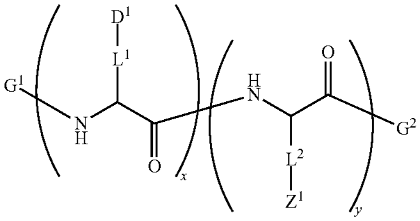

wherein:

each $D^1$ is independently a pendant donor chromophore group;

each $Z^1$ is independently a chemoselective tag;

$L^1$ and $L^2$ are each independently a linker;

x is 75 mol % or more;

y is 25 mol % or less; and $G^1$ and $G^2$ are each independently selected from a terminal group, a polymer segment, a light absorbing (e.g., donor) chromophore group, an acceptor fluorophore, a linker and a linked specific binding member. It is understood that the multichromophores described by formula (V) include any convenient arrangements of co-monomers in a defined linear sequence, which have in total the defined mol % ratios of x and y. In some cases, the $Z^1$ containing co-monomers are spaced throughout the sequence of the polymeric backbone and as such are always flanked on both sides by one or more D1 containing co-monomers.

In certain instances of formula (V), the multichromophore includes a segment of formula (VI):

(VI)

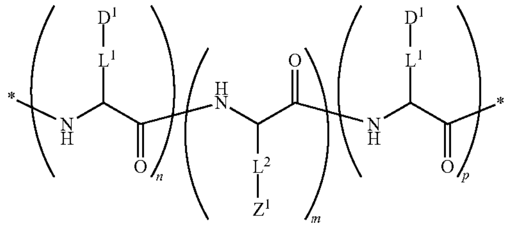

wherein:

each $D^1$ is independently a pendant light absorbing chromophore group;

each $Z^1$ is independently a chemoselective tag;

each $L^1$ and $L^2$ are independently a linker;

n and p are each independently an integer from 1 to 20 wherein n+p≥2; and m is 1 or 2.

In some cases of formula (VI), n and p are each independently 1 to 10 such as 2 to 20, 3 to 10 or 3 to 6. In some instances of formula (VI), n+p is an integer from 2 to 20, such as 3 to 20, 4 to 20, 5 to 20, 5 to 15 or 5 to 12. In certain embodiments of formula (VI), m is 1.

The subject multichromophore can include multiple segments of formula (VI) where each segment includes one isolated $Z^1$ containing co-monomers flanked by blocks of $D^1$ containing co-monomers. In some cases, the multichromophore includes two or more segments of formula (VI) located directed adjacent to each other to provide two isolated $Z^1$ containing co-monomers separated by a block of 2-20 $D^1$ containing co-monomers, such as a block of 3 to 20, 4 to 20, 5 to 20, 5 to 15 or 5 to 12 $D^1$ containing co-monomers. As such, in certain embodiments, the multichromophore includes q segments of a block copolymer and is of formula (VII):

(VII)

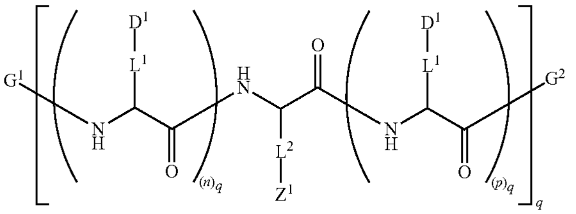

wherein: each $(n)_q$ and each $(p)_q$ is independently an integer from 1 to 20, wherein for each of the q segments $(n)_q+(p)_q≥3$; and q is an integer from 1 to 100.

It is understood that an α-amino acid residue of formulae (V)-(VII) could be replaced with a β2-amino acid residue or β3-amino acid residue to provide a corresponding polypeptide product. In formulae (V)-(VII), $D^1$ can be linked to the amino acid sidechain linker L1 via conjugation of a first chemoselective tag to a $D^1$ precursor. In formulae (V)-(VII), the $Z^1$ groups can be further conjugated to a molecule of interest via a second chemoselective tag ($Z^2$) to install a pendant group, such as a second light harvesting chromophore, an acceptor fluorophore or a linked biomolecule (e.g., as described herein).

Any convenient amino acids can be adapted for use to provide a polymeric backbone to which pendant groups can be covalently linked. The amino acids can be naturally occurring or non-naturally occurring. For example, amino acids such as lysine, ornithine have sidechain amino groups suitable for conjugation with an amino-reactive group such as an activated carboxylic acid. Cysteine includes a sidechain thiol group suitable for conjugation with a thiol-reactive group such as a maleimide or a haloacetyl. Aspartate and glutamate have sidechain carboxylic acid groups which can be conjugated with a nucleophilic group such as an amino group. Methods of preparing the subject multichromophores including peptide synthesis methods are described herein.

In some instances, the polymeric backbone of the multichromophore has one or more of the following polypeptide sequence segments:

XYXX

XXYXX

XXXYXXX

XXXYXXXX

XXXXYXXX

XXXXYXXXX

XXXXXYXXXXX

XXXXXXYXXXXXX

XXXXXXXYXXXXXXX

XXXXXXXXYXXXXXXXX

-continued

XXXXXXXXXYXXXXXXXXX

Y(X)$_n$Y

XY(X)$_n$YX

XXY(X)$_n$YXX

XXXY(X)$_n$YXXX

XXXXY(X)$_n$YXXXX

XXXXXY(X)$_n$YXXXXX where:

each X is a first amino acid residue having a sidechain-linked first chemoselective tag, or a sidechain-linked pendant donor chromophore;

each Y is a second amino acid residue having a sidechain-linked second chemoselective tag, or a sidechain-linked pendant acceptor fluorophore; and n is an integer of 2 to 20, such as 2 to 10, 3 to 10, 4 to 10 or 5 to 10, e.g., n is 2, 3, 4, 5, 6, 7, 8, 9 or 10.

In certain embodiments, in addition to the one or more polypeptide segments described herein, a third type of amino acid residue (Z) can be incorporated into the polymeric backbone, e.g., between two of the segments. In certain cases, a single isolated third amino acid residue is incorporated between any two of the segments described herein, e.g., (segment 1)-Z-(segment 2). This third amino acid residue can be a spacer residue, or a residue having a chemoselective functional group suitable for selective installation of an additional moiety of interest, such as a second pendant light absorbing chromophore, a chemoselective tag (e.g., a bio-orthogonal click chemistry tag), a linker, a linked biomolecule, a acceptor fluorophore, a WSG, etc. In certain instances the additional moiety of interest is incorporated into the third amino acid residue prior to preparation.

In certain instances, the first amino acid residue (X) includes a sidechain amino group, e.g., lysine or ornithine or a protected version thereof. During SPPS of the polymeric backbone, these sidechain amino groups can remain protected (e.g., with a Cbz or Boc protecting group), and then subsequently be orthogonally deprotected to provide for conjugation of the first residues to a pendant donor chromophore group. In certain cases, the second amino acid residue includes a sidechain thiol group, e.g., cysteine or a protected version thereof. Similarly, during SPPS of the polymeric backbone, these sidechain thiol groups can remain protected, and then subsequently be orthogonally deprotected to provide for conjugation of the second residues to a pendant group of interest, e.g., an acceptor fluorophore.

In some embodiments, the polymeric backbone of the multichromophore has, or is derived from, one or more of the following polypeptide sequence segments:

(SEQ ID NO: 1)
KCKK (SEQ ID NO: 2)
KKCK (SEQ ID NO: 3)
KKYKK (SEQ ID NO: 4)
KKKYKK

-continued (SEQ ID NO: 5)
KKYKKK (SEQ ID NO: 6)
KKKYKKK (SEQ ID NO: 7)
KKKYKKKK (SEQ ID NO: 8)
KKKKYKKK (SEQ ID NO: 9)
KKKKCKKKK (SEQ ID NO: 10)
KKKKKCKKKKK (SEQ ID NO: 11)
KKKKKKCKKKKKK (SEQ ID NO: 12)
KKKKKKKCKKKKKKK (SEQ ID NO: 13)
KKKKKKKKCKKKKKKKK (SEQ ID NO: 14)
KKKKKKKKKCKKKKKKKKK (SEQ ID NO: 15)
KKKKCKKKKKKKKKKCKKKKK (SEQ ID NO: 16)
C(K)$_n$C (SEQ ID NO: 17)
KC(K)$_n$CK (SEQ ID NO: 18)
KKC(K)$_n$CKK (SEQ ID NO: 19)
KKKC(K)$_n$CKKK (SEQ ID NO: 20)
KKKKC(K)$_n$CKKKK (SEQ ID NO: 21)
KKKKKC(K)$_n$CKKKKK wherein: each K is a lysine residue, a protected lysine residue, or a lysine residue covalently linked via the sidechain amino group to a pendant donor chromophore group; n is an integer from 2 to 20 (such as 2 to 10, 3 to 10, 4 to 10 or 5 to 10, e.g., n is 2, 3, 4, 5, 6, 7, 8, 9 or 10); and C is a cysteine residue or a protected cysteine residue.

In some embodiments, the polymeric backbone of the multichromophore has, or is derived from, one or more of the following polypeptide sequence segments:

(SEQ ID NO: 22)
OCOO (SEQ ID NO: 23)
OOCO (SEQ ID NO: 24)
OOCOO (SEQ ID NO: 25)
OOOCOO (SEQ ID NO: 26)
OOCOOO

-continued (SEQ ID NO: 27)
OOOCOOO (SEQ ID NO: 28)
OOOCOOOO (SEQ ID NO: 29)
OOOOCOOO (SEQ ID NO: 30)
OOOOCOOOO (SEQ ID NO: 31)
OOOOOCOOOOO (SEQ ID NO: 32)
OOOOOOCOOOOOO (SEQ ID NO: 33)
OOOOOOOCOOOOOOO (SEQ ID NO: 34)
OOOOOOOOCOOOOOOOO (SEQ ID NO: 35)
OOOOOOOOOCOOOOOOOOO (SEQ ID NO: 36)
OOOOOOOOOOCOOOOOOOOOO (SEQ ID NO: 37)
$C(O)_nC$ (SEQ ID NO: 38)
$OC(O)_nCO$ (SEQ ID NO: 39)
$OOC(O)_nCOO$ (SEQ ID NO: 40)
$OOOC(O)_nCOOO$ (SEQ ID NO: 41)
$OOOOC(O)_nCOOOO$ (SEQ ID NO: 42)
$OOOOOC(O)_nCOOOOO$ wherein:

O is an ornithine residue, a protected ornithine residue, or an ornithine residue covalently linked via the sidechain amino group to a pendant donor chromophore group; n is an integer from 2 to 20 (such as 2 to 10, 3 to 10, 4 to 10 or 5 to 10, e.g., n is 2, 3, 4, 5, 6, 7, 8, 9 or 10); and C is a cysteine residue or a protected cysteine residue.

In some cases of formulae (II)-(III), the polymeric backbone is a peptoid backbone. As such, the multichromophore can have formula (VIII):

(VIII)

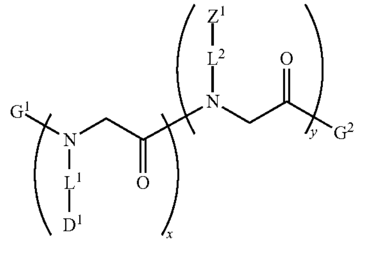

wherein each $D^1$ is independently a pendant donor chromophore group;

each $Z^1$ is independently a chemoselective tag;

each $L^1$ and $L^2$ is independently a linker;

x is 75 mol % or more;

y is 25 mol % or less; and $G^1$ and $G^2$ are each independently selected from a terminal group, a polymer segment, a light absorbing (e.g., donor) chromophore group, an acceptor fluorophore, a linker and a linked specific binding member. It is understood that the multichromophores described by formula (VIII) can include any convenient arrangements of co-monomers in a defined linear sequence, which have in total the defined mol % ratios of x and y. In some cases, the $Z^1$ containing co-monomers are spaced throughout the sequence of the polymeric backbone and as such are always flanked on both sides by one or more D1 containing co-monomers.

In some instances of formulae (IV), (V), (XIII) and (IX), x is 80 mol % or more, such as 85 mol % or more, 90 mol % or more, 95 mol % or more, 96 mol % or more, 97 mol % or more, 98 mol % or more, or 99 mol % or more. In some instances of formula (IV), (V), (XIII) and (IX), y is 20 mol % or less, such as 15 mol % or less, 10 mol % or less, 5 mol % or less, 4 mol % or less, 3 mol % or less, 2 mol % or less, 1 mol % or less.

Pendant Chromophore Groups

Any convenient light absorbing chromophore groups can be adapted for use in the subject multichromophores. The terms "light absorbing chromophore group" and "donor chromophore group" are used interchangeably and refer to a pendant group of the multichromophore capable of absorbing light at a particular absorption maximum wavelength and transferring energy to a proximate chromophore or acceptor fluorophore or converting it to emitted light at a longer emission maximum wavelength.

BODIPY Chromophore Groups

A pendant chromophore group can be a BODIPY group. In some cases of formulae (I)-(IX), each $D^1$ is independently a BODIPY group. In some cases, the BODIPY group is a pendant donor chromophore group. The term "BODIPY group" refers to a pendant group of the multichromophore which includes a chromophore having the following boron-dipyrromethene (BODIPY) core structure:

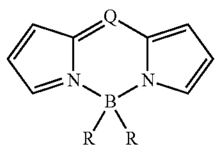

where Q is C or N and each R is any convenient boron substituent. In some cases, Q is C. In some instances, each R is independently selected from F, OH, H, alkyl, substituted alkyl, aryl, substituted aryl, heteroaryl, substituted heteroaryl, alkoxy, substituted alkoxy, alkynyl and substituted alkynyl.

The BODIPY core structure may be linked to a repeat unit of the multichromophore via any convenient positions of the core structure, via an optional sidechain linker. The BODIPY core structure may be further optionally substituted. In certain embodiments, the BODIPY group defines a sidechain group of a co-monomer which is part of a repeating unit. Any convenient BODIPY-containing structures may be adapted for use in the subject multichromophores as a BODIPY group. BODIPY-containing structures of interest include, but are not limited to, those BODIPY dyes and derivatives described by Loudet and Burgess in "BODIPY Dyes and Their Derivatives: Syntheses and Spectroscopic Properties", Chem. Rev. 2007, 107 (11): 4891-4932, Suzuki et al. in U.S. Pat. No. 8,193,350, Ulrich et al. in U.S. Pat. No. 8,476,461 and Ulrich et al. in U.S. Pat. No. 7,897,786, the disclosures of which are herein incorporated by reference in their entirety.

A BODIPY pendant chromophore group can be described by formula (XI):

(XI)

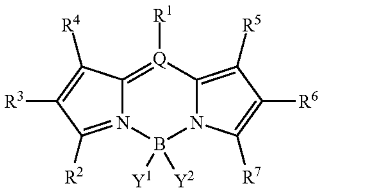

wherein:

Q is C or N;

$R^1$-$R^7$ are each independently selected from H, alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and -$L^1$-$Z^1$, or optionally any one or more pairs of substituents selected from $R^6$ and $R^7$, $R^2$ and $R^3$, $R^5$ and $R^6$, $R^3$ and $R^4$, $R^4$ and $R^1$ and $R^5$ and $R^1$, together form a divalent radical and are cyclically linked and together with the carbon atoms to which they are bound provide a 5- or 6-membered fused heterocycle, carbocycle, aryl or heteroaryl ring (e.g., a 5- or 6-membered ring comprising carbon atoms and 0-3 heteroatoms selected from O, S and N), which ring may be unsubstituted or further substituted with a substituent independently selected from alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and -$L^1$-$Z^1$;

$L^1$ is a linker;

$Z^1$ is a non-conjugated repeat unit of the polymeric backbone; and $Y^1$ and $Y^2$ are independently selected from F, OH, H, cyano, alkyl, substituted alkyl, aryl, substituted aryl, heteroaryl, substituted heteroaryl, alkoxy, substituted alkoxy, alkenyl, substituted alkenyl, alkynyl, substituted alkynyl and WSG;

wherein one of $Y^1$, $Y^2$ and $R^1$-$R^7$ is linked to a non-conjugated repeat unit of the polymeric backbone. In formula (XI), it is understood that the substituents $Y^1$, $Y^2$ and $R^1$-$R^7$ can be selected from groups that do not inhibit the fluorescence of the BODIPY group. In certain instances of formula (XI), Q is C. It is understood that for any of the BODIPY group formulae described herein, a corresponding formula may be included where the atom represented by Q in formula (XI) is a nitrogen atom. In certain embodiments of formula (XI), one or more of $Y^1$, $Y^2$ and $R^1$-$R^7$ includes a WSG. In certain instances of formula (XI), $Y^1$ and $Y^2$ each include a WSG. In certain instances of formula (XI), the linker of -$L^1$-$Z^1$ includes a WSG.

In formula (XI), the substituent pairs $R^6$ and $R^7$ and/or $R^2$ and $R^3$ can be cyclically linked to provide a 5- or 6-membered fused ring, which ring is unsubstituted or substituted. In some cases of formula (XI), the 5- or 6-membered fused ring is an aryl or heteroaryl ring selected from furan, thiophene, pyrrole, oxazole, isooxazole, thiazole, isothiazole, imidazole and pyrazole. In some instances of formula (XI), the BODIPY group is of formula (XIIa) or (XIIb):

(XIIa)

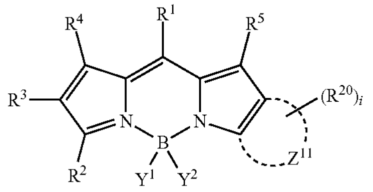

(XIIb)

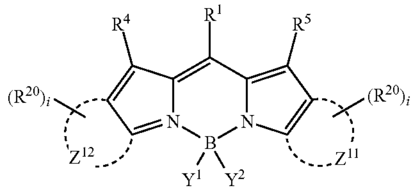

wherein:

$Z^{11}$ and $Z^{12}$ are independently the fused 5- or 6-membered fused heterocycle, carbocycle, aryl or heteroaryl ring;

each "i" is independently 0-3; and each $R^{20}$ is independently a substituent group as defined for $R^2$-$R^7$ in formula (X). In certain embodiments of formulae (XIIa)-(XIIb), $Z^{11}$ and $Z^{12}$ are independently a 5- or 6-membered fused aryl or heteroaryl ring. In some cases, $Z^{11}$ and $Z^{12}$ are independently selected from furan, thiophene, pyrrole, oxazole, isooxazole, thiazole, isothiazole, imidazole and pyrazole. In some cases of formulae (XIIa)-(XIIb), $Z^{11}$ and/or $Z^{12}$ are furan or thiophene. In certain cases of formula (XIIa), none of $R^1$-$R^5$ are cyclically linked. In some instances of formulae (XIa)-(XIIb), $Z^{11}$ and $Z^{12}$ are independently selected from the following rings:

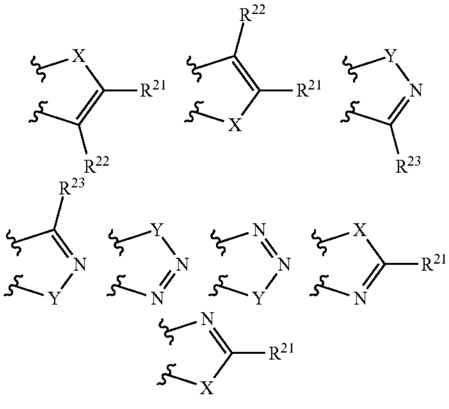

wherein:

X is O or S;

Y is O, S or NR, wherein R is H, alkyl, substituted alkyl or a substituent as defined for $R^{20}$ in formulae (XIIa)-(XIIb); and $R^{21}$-$R^{23}$ are independently selected from H and a substituent as defined for $R^{20}$ in formulae (XIIa)-(XIIb). In certain instances of formulae (XIIa)-(XIIb), $Z^{11}$ and $Z^{12}$ are independently selected from the following rings:

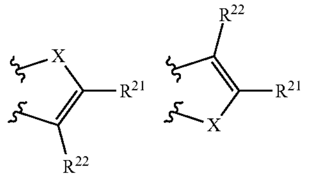

as defined above.

In certain cases of formulae (XIIb), $Z^{11}$ and $Z^{12}$ are the same rings. In certain instances, $Z^{11}$ and $Z^{12}$ include different rings.

In certain embodiments of formula (XIIa), the BODIPY group is of formula (XIIIa) or (XIIIb):

(XIIIa)

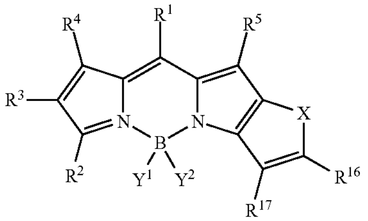

(XIIIb)

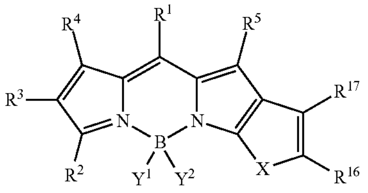

wherein:

X is O or S: and $R^{16}$ and $R^{17}$ are substituents as defined for $R^6$ and $R^7$ in formula (I).

In certain cases of formula (XIIIa) or (XIIIb), none of $R^1$-$R^5$ are cyclically linked.

In certain embodiments of formula (XI) and (XIIb), the BODIPY group is of formula (XIVa) or (XIVb):

(XIVa)

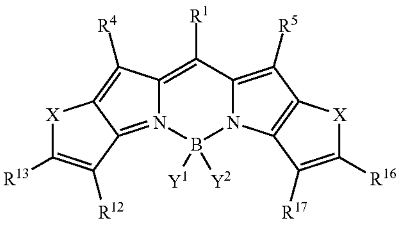

-continued (XIVb)

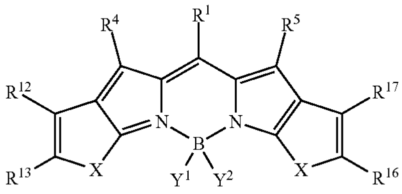

wherein:

each X is O or S; and $R^{12}$, $R^{13}$, $R^{16}$ and $R^{17}$ and are substituents as defined for $R^2$, $R^3$, $R^6$ and $R^7$ in formula (I).

In certain embodiments of formulae (XI)-(XIVb), the BOBIPY group includes a linked chemoselective functional group or molecule of interest, such as a light harvesting multichromophore (e.g., $-L^1-Z^1$). In some instances, one of $R^1$-$R^7$ includes $-L^1-Z^1$. In certain instances, $Y^1$ or $Y^2$ includes $-L^1-Z^1$. In certain embodiments of formulae (XI)-(XIVb), $R^1$ is $-L^1-Z^1$ where $L^1$ is a linker and $Z^1$ is a chemoselective functional group or a light harvesting multichromophore. In certain embodiments of formulae (XI)-(XIVb), $R^4$ or $R^5$ is $-L^1-Z^1$. In certain embodiments of formulae (XI), (XIIa) and (XIIIa)-(XIIIb), $R^2$ or $R^7$ is $-L^1-Z^1$. In certain embodiments of formulae (XI), (XIIa) and (XIIIa)-(XIIIb), $R^3$ or $R^6$ is $-L^1-Z^1$. In certain embodiments of formulae (XIIa)-(XIIb), a $R^{20}$ substituent is $-L^1-Z^1$. In certain embodiments of formulae (XIIIa)-(XIIIb), $R^{16}$ or $R^{17}$ is $-L^1-Z^1$. In certain embodiments of formulae (XIVa)-(XIVb), $R^{12}$, $R^{13}$, $R^{16}$ or $R^{17}$ is $-L^1-Z^1$.

In some cases, $R^1$ is $-L^1-Z^1$ where $L^1$ is a linker (e.g., as described herein) having a backbone of 20 atoms or less in length. In some instances of $R^1$, $L^1$ is selected from an alkyl or substituted alkyl linker, an alkoxy or substituted alkoxy linker, a PEG linker, a sulfonamido-alkyl or substituted sulfonamido-alkyl linker, an amido-alkyl or substituted amido-alkyl linker and an alkyl-amido-alkyl or substituted alkyl-amido-alkyl linker. The linker may be substituted with a WSG, such as a PEG group. In certain instances of $R^1$, $L^1$ is selected from a $C_1$-$C_{12}$ alkyl or substituted alkyl linker, a $C_1$-$C_{12}$ alkoxy or substituted alkoxy linker, a $C_1$-$C_{12}$ amido-alkyl or substituted amido-alkyl linker and a $C_1$-$C_{12}$ alkyl-amido-alkyl or substituted alkyl-amido-alkyl linker. In certain instances of $R^1$, $Z^1$ is conjugated to the BODIPY group via a carboxylic acid or an active ester thereof.

In certain instances of formulae (XI)-(XIVb), $R^1$ includes an optionally substituted carbocyclic or heterocyclic group linked to a repeat unit of the light harvesting multichromophore or to a chemoselective functional group. In certain instances, $R^1$ is an optionally substituted aryl or heteroaryl linked to a repeat unit of the light harvesting multichromophore, e.g., via a chemoselective functional group. Bivalent carbocyclic or heterocycle groups of interest include, but are not limited to, 1,4-cyclohexyl, 1,3-cyclohexyl, piperidinyl (e.g., 1,4-piperidinyl), piperazinyl (e.g., 1,4-piperazinyl), and the like. Bivalent aryl or heteroaryl groups of interest include, but are not limited to, 1,4-phenyl, 1,3-phenyl, 2,5-pyridyl, 2,6-pyridyl, 3,5-pyridyl, and the like. The bivalent carbocyclic or heterocycle group or the bivalent aryl or heteroaryl group of $R^1$ may be linked to $-L^2-Z^1$, where $L^2$ is a linking group, e.g., as described in any one of the embodiments herein.

In some embodiments of formula (XI), Q is C and $R^1$-$R^7$ are each independently selected from H, alkyl, substituted alkyl, alkoxy, substituted alkoxy, aryl, substituted aryl, heteroaryl, substituted heteroaryl, alkenyl, substituted alkenyl, alkynyl and substituted alkynyl. In certain instances of formula (XI), $Y^1$ and $Y^2$ are each include one or more water solubilizing groups (WSGs). In some cases, $Y^1$ and $Y^2$ are an alkynyl substituted with a WSG. In some cases, $Y^1$ and $Y^2$ are each an alkynyl substituted with a branched WSG. In some instances of formula (XI), $Y^1$ and $Y^2$ are each —CC—$CH_2)_n$—$O(CH_2CH_2O)_m$—R, wherein n is 1 to 6, m is 2 to 50, such as 2 to 30, 2 to 20, 6 to 20, 8 to 20, or 10 to 20, and R is H, alkyl or substituted alkyl (e.g., methyl).

In some embodiments of formula (XI), the BODIPY pendant donor chromophore group can be described by formula (XIa):

(XIa)

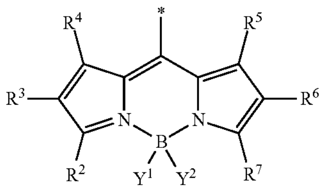

wherein:

* is a point of linkage to a non-conjugated repeat unit of the polymeric backbone;

$Y^1$ and $Y^2$ are each alkynyl substituted with one or more WSGs. In some cases, $Y^1$ and $Y^2$ are each alkynyl substituted with a branched WSG. In some instances of formula (XIa), each $R^{10}$ is —CC—$CH_2)_n$—O$(CH_2CH_2O)_m$—R, wherein n is 1 to 6, m is 2 to 50, such as 2 to 30, 2 to 20, 6 to 20, 8 to 20, or 10 to 20, and R is H, alkyl or substituted alkyl (e.g., methyl).

In certain instances of formula (XI), the BODIPY group is of formula (XV):

(XV)

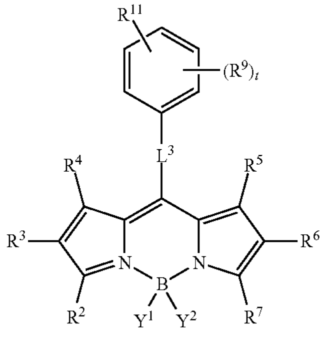

wherein:

$L^3$ is a covalent bond, oxo (—O—), alkylene (e.g., $C_1$-$C_6$-alkylene), —O-alkylene or a substituted version thereof;

$R^{11}$ is as defined for $R^1$;

each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4. In certain cases of formula (XV), $L^3$ is a covalent bond. In some cases of formula (XV), $L^3$ is oxo. In certain cases of formula (XV), $L^3$ is a covalent bond.

In certain instances of formula (XV), the BODIPY group is of formula (XVa):

(XVa)

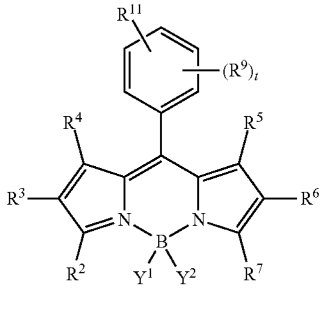

wherein: $R^{11}$ is as defined for $R^1$; each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4. In some cases of formulae (XV)-(XVa), $R^{11}$ is $L^1$-$Z^1$ (e.g., as described herein). In some cases of formulae (XV)-(XVa), $R^{11}$ includes a sulfonamido-alkyl or substituted sulfonamido-alkyl linker, an amido-alkyl or substituted amido-alkyl linker or an alkyl-amido-alkyl or substituted alkyl-amido-alkyl linker. In certain instances of formulae (XV)-(XVa), $R^2$, $R^4$, $R^5$ and $R^7$ are each independently H, alkyl or substituted alkyl. In certain instances of formulae (XV)-(XVa), $R^3$ and $R^6$ are each independently H, alkyl or substituted alkyl. In some cases, $R^3$ and $R^6$ are each H. In certain instances of formulae (XV)-(XVa), $R^2$, $R^4$, $R^5$ and $R^7$ are each independently $C_1$-$C_6$alkyl or substituted $C_1$-$C_6$alkyl.

In certain instances of formula (XV), the BODIPY group is of formula (XVIa) or (XVIb):

(XVIa)

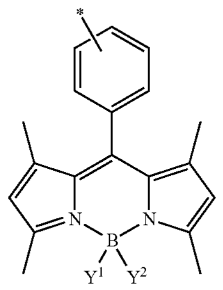

(XVIb)

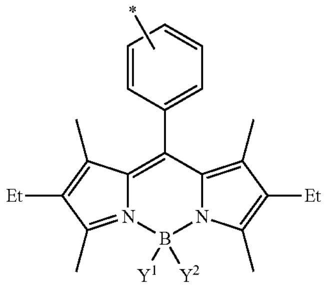

wherein:

* is a point of linkage to a repeat unit of the light harvesting multichromophore or a chemoselective functional group; and $Y^1$ and $Y^2$ are independently selected from the group consisting of F, OH, H, alkyl, substituted alkyl, aryl, substituted aryl, heteroaryl, substituted heteroaryl, alkoxy, substituted alkoxy, alkynyl, substituted alkynyl and WSG.

In certain instances of formula (XI), the BODIPY group is of formula (XVIIa) or (XVIIb):

(XVIIa)

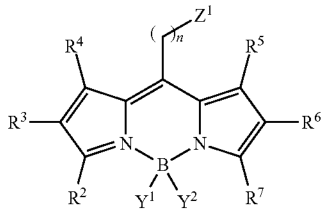

(XVIIb)

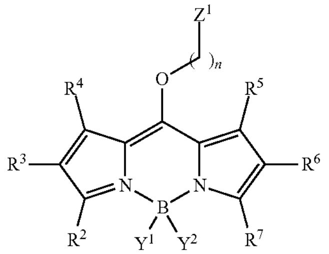

wherein: n is 0-12 and $Z^1$ is a chemoselective functional group (e.g., as described herein) or linked molecule of interest. In certain cases of formulae (XVIIa)-(XVIIb), n is 1-12 or 1-6, e.g., 1, 2, 3, 4, 5 or 6. In certain instances of formulae (XVIIa)-(XVIIb), $R^2$-$R^4$ and $R^5$-$R^7$ are each independently selected from H, $C_1$-$C_6$ alkyl and substituted $C_1$-$C_6$ alkyl. In certain instances of formulae (XVIIa)-(XVIIb), $R^2$ and $R^4$ and/or $R^5$ and $R^7$ are each independently selected from $C_1$-$C_6$ alkyl and substituted $C_1$-$C_6$ alkyl. In certain instances of formulae (XVIIa)-(XVIIb), $R^3$ and/or $R^6$ are H. In certain instances of formulae (XVIIa)-(XVIIb), $R^3$ and/or $R^6$ are alkyl or substituted alkyl.

In certain instances of formula (XIIIa), the BODIPY group is of formula (XVIII):

(XVIII)

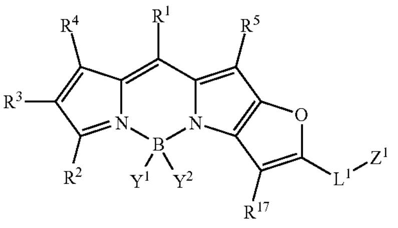

wherein: $L^1$ is a linker and $Z^1$ is a linked non-conjugated repeat unit of the polymeric backbone (e.g., as described herein). In certain instances of formula (XVIII), the BODIPY group is of formula (XVIIIa):

(XVIIIa)

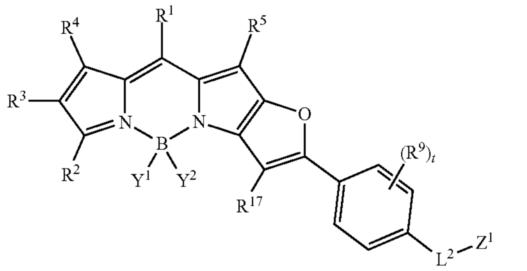

wherein: $L^2$ is a linker (e.g., a linking group component of $L^1$); each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4.

In certain instances of formula (XIVa), the BODIPY group is of formula (XIX):

(XIX)

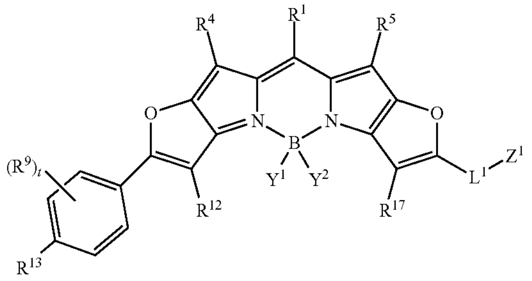

wherein: $R^{12}$ and $R^{13}$ are substituents as defined for $R^2$ and $R^3$ in formula (XI); $L^1$ is a linker and $Z^1$ is a linked non-conjugated repeat unit of the polymeric backbone (e.g., as described herein). In certain instances of formula (XIX), the BODIPY group is of formula (XIXa):

(XIXa)

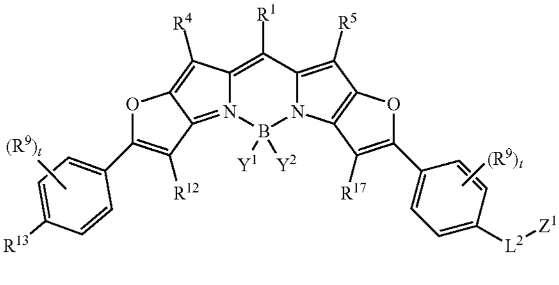

wherein: $L^2$ is a linker (e.g., a linking group component of $L^1$); each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4.

In any of the embodiments of formula (XI)-(XIXa) described herein, the BODIPY group can include a particular $-L^1-Z^1$ group as described in one of the following embodiments.

$L^1$ can be a linker (e.g., as described herein) having a backbone of 20 atoms or less in length. In some instances, $L^1$ is selected from an alkyl or substituted alkyl linker, an alkoxy or substituted alkoxy linker, a PEG linker, a sulfonamido-alkyl or substituted sulfonamido-alkyl linker, an amido-alkyl or substituted amido-alkyl linker and an alkyl-amido-alkyl or substituted alkyl-amido-alkyl linker. The linker may be substituted with a WSG, such as a PEG group. In certain instances, $L^1$ is selected from a $C_1$-$C_{12}$ alkyl or substituted alkyl linker, a $C_1$-$C_{12}$ alkoxy or substituted alkoxy linker, a $C_1$-$C_{12}$ amido-alkyl or substituted amido-alkyl linker and a $C_1$-$C_{12}$ alkyl-amido-alkyl or substituted alkyl-amido-alkyl linker. The linker L can include several linked components, such as one or linking groups independently selected from lower alkylene, substituted lower alkylene, alkenylene (—CH═CH—), substituted alkenylene, alkynylene (—CC—), substituted or unsubstituted amido (e.g., —NRCO— or —CONR—, where R Is H, alkyl or substituted alkyl), substituted or unsubstituted sulfonamido (e.g., —$NRSO_2$— or —$SO_2NR$—, where R Is H, alkyl or substituted alkyl), oxo (—O—), thio (—S—), ethylene glycol (—$OCH_2CH_2O$—), polyethylene glycol (e.g., —$(CH_2CH_2O)_n$— where n is 2-20, such as 2-10 or 2-6, or 2, 3, 4, 5 or 6), arylene, substituted arylene, heteroarylene, substituted heteroarylene, alpha-amino acid residue, beta-amino acid residue, and the like.

The linked non-conjugated repeat unit of the polymeric backbone ($Z^1$) can be conjugated to the BODIPY group via any convenient chemoselective functional group, e.g., a functional group suitable for conjugation to a molecule of interest having a compatible functional group. Chemoselective functional groups of interest which find use in linked the subject BODIPY groups to the polymeric backbone include, but are not limited to, amine groups (e.g., —$NH_2$), carboxylic acid (—$CO_2H$), active ester (e.g., NHS or sulfo-NHS ester), thiol, maleimide, iodoacetamide, hydroxyl, hydrazido, hydrazino, aldehyde, ketone, azido, alkyne, tetrazine, alkene, phosphine and epoxide. It is understood that in some cases, the chemoselective functional group used to link a BODIPY group is a synthetic precursor or protected version of the functional group of interest, which may be converted to a reactive functional group capable of conjugation the polymeric backbone. For example, a carboxylic acid is a chemoselective functional group which can be coupled with an amine group on a molecule of interest. The carboxylic acid may be converted to an active ester that couples with the amine group, either in situ or prior to coupling.

In some embodiments of formulae (XI)-(XIXa), $L^1$ includes an optionally substituted carbocyclic or heterocyclic group linked to a non-conjugated repeat unit of the polymeric backbone. In certain instances, $L^1$ is an optionally substituted aryl or heteroaryl. Bivalent carbocyclic or heterocycle groups of interest include, but are not limited to, 1,4-cyclohexyl, 1,3-cyclohexyl, piperidinyl (e.g., 1,4-piperidinyl), piperazinyl (e.g., 1,4-piperazinyl), and the like. Bivalent aryl or heteroaryl groups of interest include, but are not limited to, 1,4-phenyl, 1,3-phenyl, 2,5-pyridyl, 2,6-pyridyl, 3,5-pyridyl, and the like. The bivalent carbocyclic or heterocycle group or the bivalent aryl or heteroaryl group of $L^1$ may be linked to -$L^2$-$Z^1$, where $L^2$ is a linking group, e.g., as described in any one of the embodiments herein. In some embodiments of formulae (I)-(IXa), -$L^1$-$Z^1$ is described by one of the following structures:

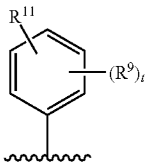

wherein:

$R^{11}$ is $L^2$-$Z^1$;

$L^2$ is a linker and $Z^1$ is a non-conjugated repeat unit of the polymeric backbone;

t is 0-4; and each $R^9$ is independently selected from alkyl, substituted alkyl, alkoxy, substituted alkoxy, hydroxy, aryl, substituted aryl, heteroaryl, substituted heteroaryl, halogen, sulfonic acid and water solubilizing group (WSG). In certain embodiments, -$L^1$-$Z^1$ is described by one of the following structures:

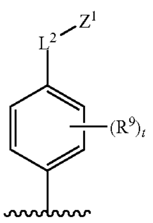

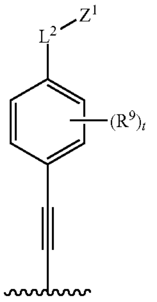

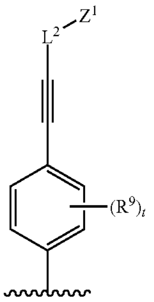

wherein:

$L^2$ is a linker and $Z^1$ is a non-conjugated repeat unit of the polymeric backbone;

t is 0-4; and each $R^9$ is independently selected from alkyl, substituted alkyl, alkoxy, substituted alkoxy, hydroxy, aryl, substituted aryl, heteroaryl, substituted heteroaryl, halogen, sulfonic acid and water solubilizing group (WSG). In certain embodiments, -$L^1$-$Z^1$ is described by one of the following structures:

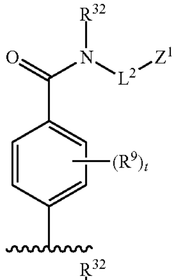

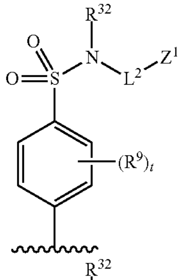

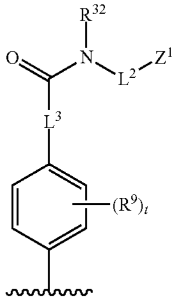

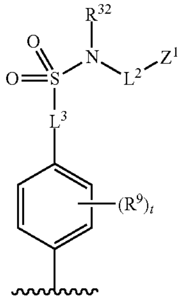

wherein:

$L^2$ is a linker and $Z^1$ is a non-conjugated repeat unit of the polymeric backbone;

$R^{32}$ is H, alkyl, substituted alkyl, and water solubilizing group (WSG);

$L^3$ is a linker selected from alkylene (e.g., $C_1$-$C_6$-alkylene), —O-alkylene and substituted versions thereof;

t is 0-4; and each $R^9$ is independently selected from alkyl, substituted alkyl, alkoxy, substituted alkoxy, hydroxy, aryl, substituted aryl, heteroaryl, substituted heteroaryl, halogen, sulfonic acid and water solubilizing group (WSG).

In any of the embodiments of formulae (XI)-(XIXa) described herein, the BODIPY group can include particular $Y^1$ and $Y^2$ groups as described in one of the following embodiments. In some cases of formulae (XI)-(XIXa), $Y^1$ includes a water solubilizing groups (WSG). In certain cases, $Y^1$ is alkynyl substituted with WSG. $Y^2$ can be the same as $Y^1$ or different. In some cases of formulae (XI)-(XIXa), $Y^2$ is selected from F, OH, H, cyano, alkyl, substituted alkyl, aryl, substituted aryl, heteroaryl, substituted heteroaryl, alkenyl, substituted alkenyl, alkynyl and substituted alkynyl. In some instances, $Y^2$ is selected from F, CN, phenyl and substituted phenyl.

In some cases of formulae (XI)-(XIXa), $Y^1$ and $Y^2$ each comprises a water solubilizing group (WSG). In certain instances, $Y^1$ and/or $Y^2$ is alkynyl substituted with a WSG (e.g., as described herein). In certain instances, $Y^1$ and/or $Y^2$ is alkynyl substituted with polyethylene glycol (PEG) or modified (PEG). In certain cases of any of the embodiments of formulae (I)-(IXa), $Y^1$ and/or $Y^2$ is of the formula:

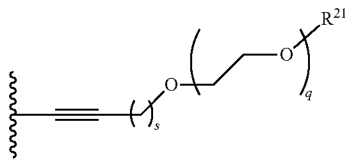

wherein:

s is 1 to 12;

q is 0 to 50; and $R^{21}$ is H, alkyl or substituted alkyl. In certain cases, s is 1 to 6, such as 1, 2 or 3. In some instances, q is 1 to 50, 1 to 30, 2 to 30, 4 to 30, 6 to 30, 8 to 30, 10 to 30, 10 to 20 or 11 to 16. In certain cases, q is 10 to 50, such as 10 to 30, 10 to 20 or 11 to 16.

In certain embodiments of formula (XI) and (XVIIa), the BODIPY group has the structure:

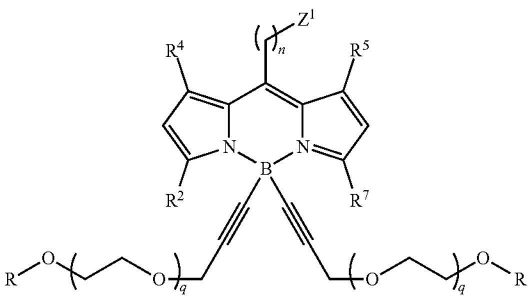

where $Z^1$ is a linked non-conjugated repeat unit of the polymeric backbone; n is 0-6; each R, $R^2$, $R^4$, $R^5$ and $R^7$ is independently H, $C_1$-$C_6$alkyl or substituted $C_1$-$C_6$alkyl; and each q is 6-20 (e.g., 10-20). In certain embodiments of formula (XI) and (XVIIa), the BODIPY group has one of the following structures:

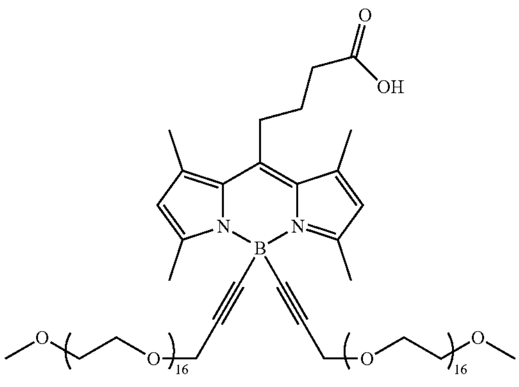

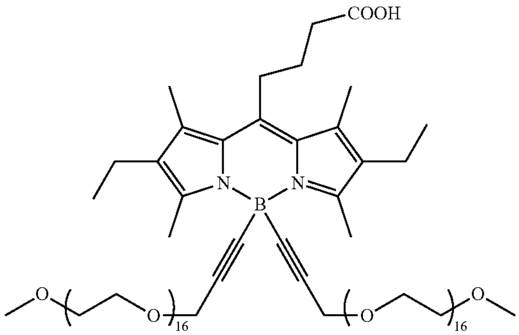

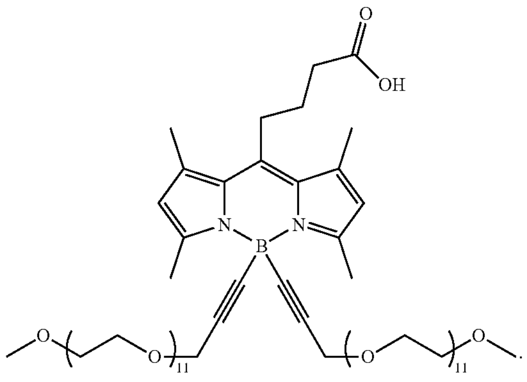

In certain embodiments of formulae (XV) and (XVa), the BODIPY dye has the structure:

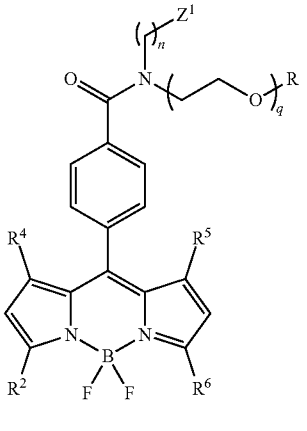

where $Z^1$ is a linked non-conjugated repeat unit of the polymeric backbone; n is 0-6; R, $R^2$, $R^4$, $R^5$ and $R^7$ is independently H, $C_1$-$C_6$alkyl or substituted $C_1$-$C_6$alkyl; and each q is 6-20 (e.g., 10-20). In certain embodiments of formulae (XV), (XVa) and (XVIa) or (XVIb), the BODIPY dye has one of the following structures:

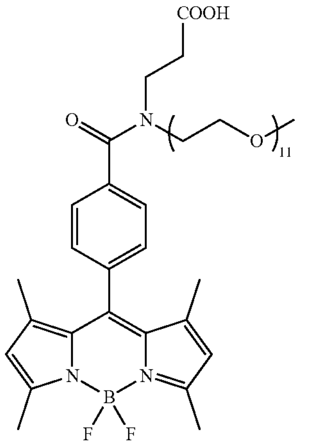

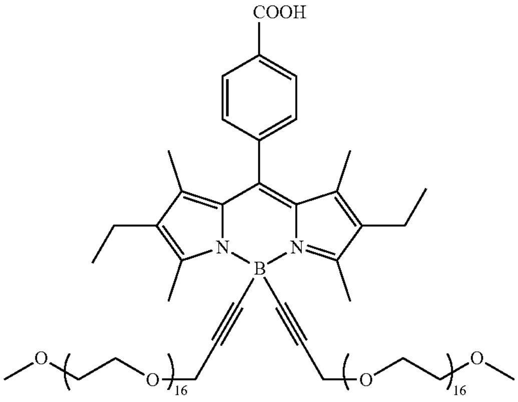

-continued

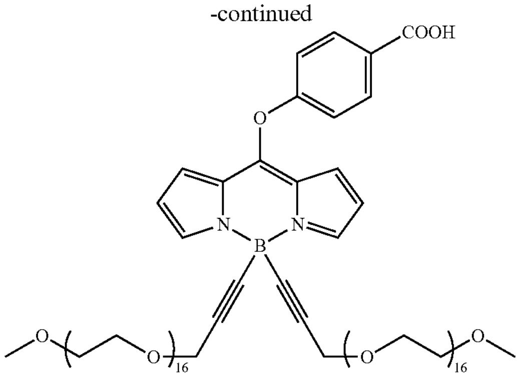

In certain embodiments of formulae (XVIII), the BODIPY group has the structure:

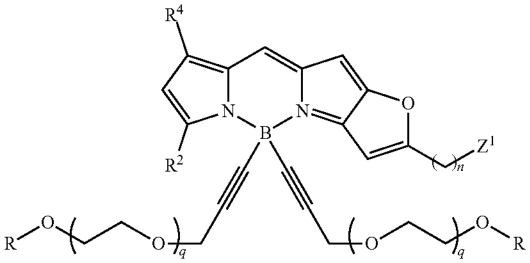

where $Z^1$ is a linked non-conjugated repeat unit of the polymeric backbone; n is 0-6; each R, $R^2$ and $R^4$ is independently H, $C_1$-$C_6$alkyl or substituted $C_1$-$C_6$alkyl; and each q is 6-20 (e.g., 10-20). In certain embodiments of formulae (XVIII), the BODIPY group has one of the following structures:

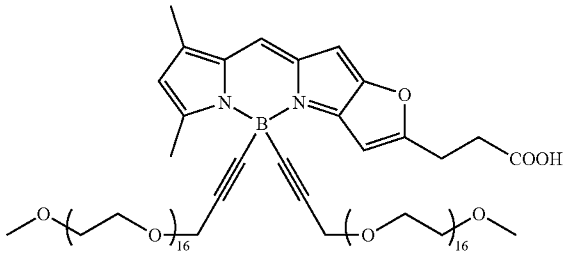

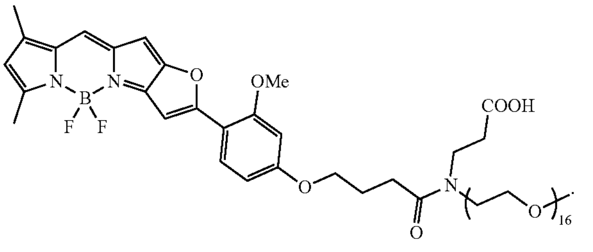

In certain embodiments of formulae (XIX)-(XIXa), the BODIPY group has the structure:

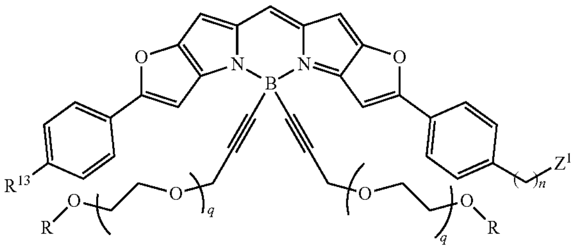

where $Z^1$ is a linked non-conjugated repeat unit of the polymeric backbone; n is 0-6; each R and $R^{13}$ is independently H, $C_1$-$C_6$alkyl or substituted $C_1$-$C_6$alkyl; and each q is 6-20 (e.g., 10-20). In certain embodiments of formulae (XIX)-(XIXa), the BODIPY group has the structure:

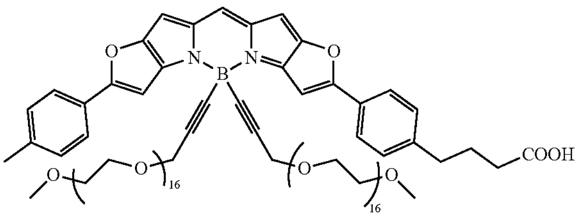

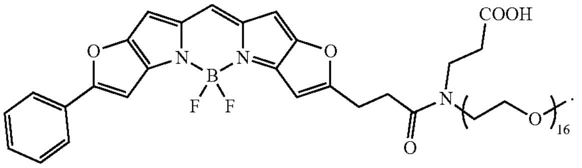

In certain embodiments of formulae (XIIIa), the BODIPY group has the structure:

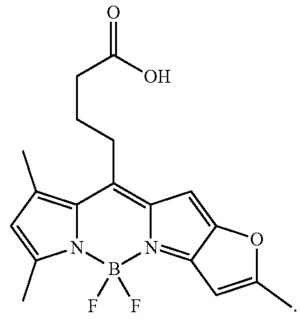

In certain embodiments of formulae (XIVa), the BODIPY group has the structure:

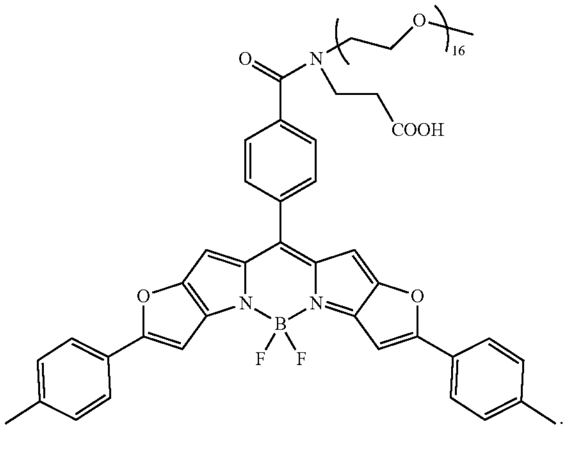

In certain embodiments of formulae (XIXa), the BODIPY group has one of the following structures:

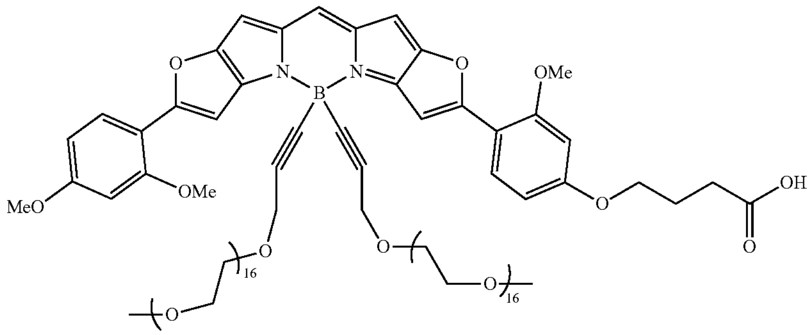

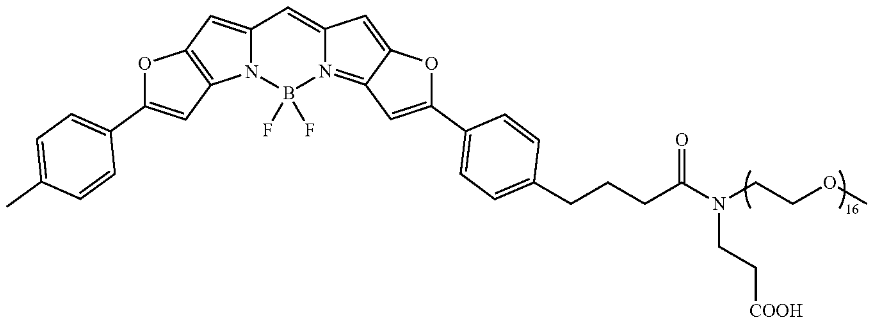

-continued

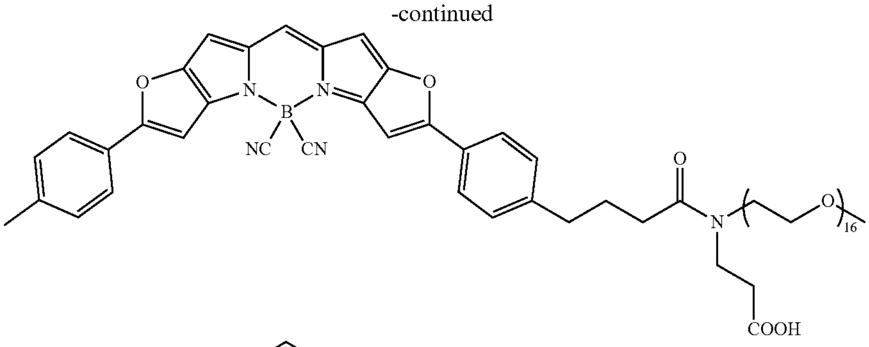

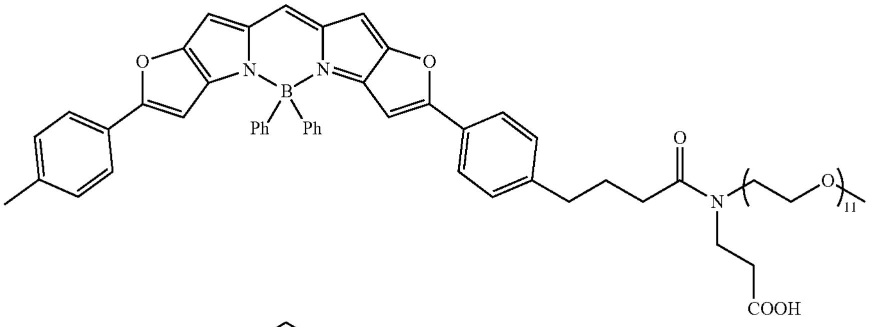

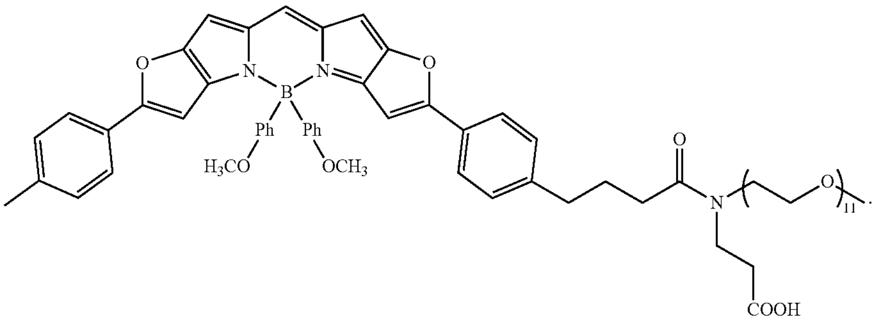

Aryl or Heteroaryl Chromophore Groups

The light absorbing chromophore group can be an aryl or heteroaryl chromophore group. Aryl or heteroaryl chromophore groups of interest which find use in the subject multichromophores (e.g., of formulae (I)-(IX) include, but are not limited to, phenyl, biphenyl, benzooxazole, benzothiazole, poly-phenylene, and fused tricyclic groups, such as fluorene, carbazole, silole, biphenyl and bridged biphenyl. The aryl or heteroaryl chromophore groups may be optionally further substituted, e.g., with a water solubilizing group and/or an aryl or heteroaryl substituent that imparts desirable light absorbing properties to the aryl or heteraryl group. In some cases of formulae (I)-(IX), each $D^1$ independently includes a fused tricyclic aryl or heteroaryl. In some cases of formulae (I)-(IX), each $D^1$ independently includes one or more groups selected from fluorene, carbazole, silole, biphenyl and bridged biphenyl.

A fused tricyclic chromophore is a group including a tricyclic aromatic group having three fused rings in a configuration where two aryl or heteroaryl 6-membered rings are fused to a central 5 or 6-membered carbocyclic or heterocyclic ring. In some cases, the fused tricyclic group includes two benzo or pyrido rings fused to a central 5 or 6 membered carbocyclic or heterocyclic ring. The fused tricyclic group can be linked to the sidechain of a co-monomer in the polymeric backbone via any convenient ring atoms of the fused rings. The central 5- or 6-membered ring may be a carbocycle or a heterocycle, aromatic or partially saturated, and may further include a sidechain substituent, e.g., a WSG and/or a linker to a chemoselective tag or the co-monomer sidechain. A bridged biphenyl co-monomer is a fused tricyclic group having a biphenyl group where the two phenyl rings are further linked with each other via a central 6 membered carbocyclic or heterocyclic ring.

In certain instances of the multichromophore (e.g., in formulae (I)-(IX)), a pendant donor chromophore group is a fused tricyclic aryl or heteroaryl having one of the following formulae:

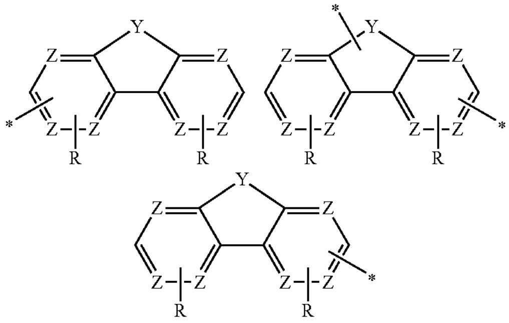

wherein:

* is a point of linkage to a non-conjugated repeat unit of the polymeric backbone;

Y is $C(R^{13})_2$, $—C(R^{13})_2C(R^{13})_2—$, $—C(R^{13})_2Si(R^{13})_2—$, $NR^{13}$, $Si(R^{13})_2$ or Se;

each Z is independently CH, CR or N;

each $R^{13}$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a non-conjugated repeat unit and a WSG, or wherein any two convenient $R^3$ groups are optionally cyclically linked; and each R is independently H or one or more substituents (e.g., WSGs) and wherein any two convenient R groups are optionally cyclically linked. In some cases, one of R and $R^{13}$ is linked to a non-conjugated repeat unit of the polymeric backbone.

In certain instances, the fused tricyclic group is described by one of the following structures:

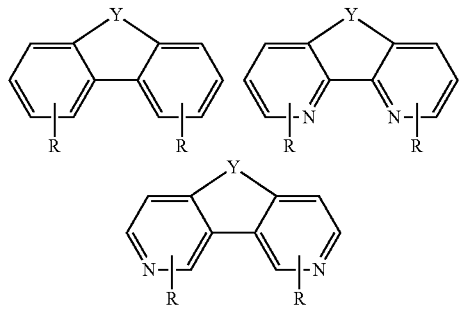

wherein Y and each R are as defined above; and the fused tricyclic group can be linked to the non-conjugated repeat unit of the polymeric backbone via Y or R.

In certain cases, the fused tricyclic group is a fluorene where Y is $C(R^3)_2$. In some cases, the fused tricyclic group is a carbazole where Y is $NR^3$. In some cases, the fused tricyclic group is a silole where Y is $Si(R^3)_2$. In some cases, the fused tricyclic group is a bridged biphenyl where Y is $—C(R^3)_2C(R^3)_2—$ or is $—C(R^3)_2Si(R^3)_2—$. In some cases, the fused tricyclic is a bridged biphenyl where Y is $—CHR^3CHR^3—$. In certain instances of any of the fused tricyclic groups described herein, each R is independently selected from H, halogen, alkoxy, substituted alkoxy, alkyl and substituted alkyl. In certain cases, each R is independently selected from H, fluoro, chloro, methoxy, substituted alkoxy, alkyl and substituted alkyl.

In certain embodiments of the fused tricyclic group, the group includes two R substituent groups that are cyclically linked to provide a carbocyclic or heterocyclic ring A that is optionally further substituted:

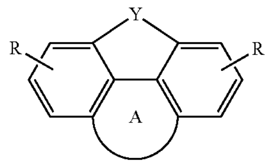

wherein Y is $C(R^3)_2$, $—C(R^3)_2C(R^3)_2—$, $—C(R^3)_2Si(R^3)_2—$, $NR^3$, $Si(R^3)_2$ or Se; and each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG; each R is as defined above; and the fused tricyclic group can be linked to the non-conjugated repeat unit of the polymeric backbone via $R^3$ or R. In certain cases, the fused tricyclic group has the structure:

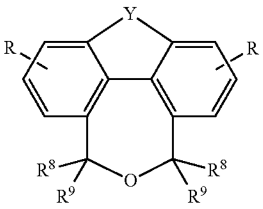

wherein $R^8$-$R^9$ are each independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, $-L^{11}-Z^1$, where $L^{11}$ is a linker and $Z^1$ is a chemoselective tag (e.g., a tag including a chemoselective functional group) and a WSG; Y and each R is as defined above; and the fused tricyclic group can be linked to the non-conjugated repeat unit of the polymeric backbone via Y, $R^8$-$R^8$ or R. In some cases of the co-monomer, Y is $C(R^3)_2$.

Water Solubilizing Groups

The present disclosure includes water soluble light harvesting multichromophores having pendant chromophore groups and polymeric tandem dyes including acceptor fluorophores. The multichromophore can be substituted with a plurality of water solubilizing groups (WSG). In some cases, the WSGs are pendant groups connected directly to the modular scaffold, e.g., as sidechains of a polymeric backbone. In certain cases, the WSGs are substituent groups attached to a pendant donor chromophore or pendant acceptor fluorophore. In some instances, each of the pendant donor chromophore groups are substituted with one or more WSG.

As used herein, the terms "water solubilizing group", "water soluble group" and WSG are used interchangeably and refer to a group or substituent that is well solvated in aqueous environments e.g., under physiological conditions, and which imparts improved water solubility upon the molecule to which it is attached. A WSG can increase the solubility of a multichromophore in a predominantly aqueous solution, as compared to a control multichromophore which lacks the WSG. The water solubilizing groups may be any convenient hydrophilic group that is well solvated in aqueous environments.

A water soluble multichromophore of the present disclosure has solubility under aqueous conditions that makes it especially suitable for application to a variety of biological assays. The subject water soluble multichromophores and polymeric tandem dyes, and conjugates thereof, can be resistant to undesirable aggregation which provides advantageous fluorescence and spectroscopic properties in various biological assays. Aggregation of dyes is undesirable because it can lead to reduced fluorescent signals, e.g., via aggregation-caused quenching of dye fluorescence. The subject water-soluble multichromophores and polymeric tandem dyes can be used as fluorescent reporters for a variety of biosensors and provide signals of exceptional brightness with a range of options for excitation and emission wavelength for applications such as Flow Cytometry, and imaging.

A variety of water soluble polymer groups can be adapted for use in the WSG of the subject multichromophores. Any convenient water solubilizing groups (WSG's) may be included in the multichromophores described herein to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. In some cases, the hydrophilic water solubilizing group is charged, e.g., positively or negatively charged. In certain cases, the hydrophilic water solubilizing group is a neutral hydrophilic group. In some embodiments, the WSG is branched (e.g., as described herein). In certain instances, the WSG is linear. In some embodiments, the WSG is a hydrophilic polymer, e.g., a polyethylene glycol, a modified PEG, a peptide sequence, a peptoid, a carbohydrate, an oxazoline, a polyol, a dendron, a dendritic polyglycerol, a cellulose, a chitosan, or a derivative thereof. Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, amino acid, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3^+$, Y', $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —$(CH_2CH_2O)_{yy}CH_2CH_2XR^{yy}$, —$(CH_2CH_2O)_{yy}CH_2CH_2X$—, —$X(CH_2CH_2O)_{yy}CH_2CH_2$—, glycol, and polyethylene glycol, wherein yy is selected from 1 to 1000, X is selected from O, S, and $NR^{ZZ}$, and $R^{ZZ}$ and $R^{YY}$ are independently selected from H and $C_{1-3}$ alkyl. In some cases, a WSG is $(CH_2)_x(OCH_2CH_2)_yOCH_3$ where each x is independently an integer from 0-20, each y is independently an integer from 0 to 50. In some cases, the water solubilizing group includes a non-ionic polymer (e.g., a PEG polymer) substituted at the terminal with an ionic group (e.g., a sulfonate).

In some embodiments of the formulae, the pendant group of interest includes a substituent selected from $(CH_2)_x(OCH_2CH_2)_yOCH_3$ where each x is independently an integer from 0-20, each y is independently an integer from 0 to 50; and a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, the substituent is $(CH_2)_3(OCH_2CH_2)_{11}OCH_3$. In some embodiments, one or more of the substituents is a benzyl substituted with at least one WSG groups (e.g., one or two WSG groups) selected from $(CH_2)_x(OCH_2CH_2)_yOCH_3$ where each x is independently an integer from 0-20 and each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In certain embodiments, the branching linker is an amino acid, e.g., a lysine amino acid that is connected to three groups via the amino and carboxylic acid groups. In some cases, the incorporation of multiple WSGs via branching linkers imparts a desirable solubility on the multichromophore. In some instances, the WSG is a non-ionic sidechain group capable of imparting solubility in water in excess of 50 mg/mL. In some instances, the WSG is a non-ionic sidechain group capable of imparting solubility in water in excess of 100 mg/mL. In some embodiments, the multichromophore includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 2-20 units).

Water soluble polymers of interest that can be utilized in the WSG include polyethylene glycol (PEG) groups or modified PEG groups. Water-soluble polymers of interest include, but are not limited to, polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Examples of water soluble polymers of interest include, but are not limited to, those containing a polyalkylene oxide, polyamide alkylene oxide, or derivatives thereof, including polyalkylene oxide and polyamide alkylene oxide comprising an ethylene oxide repeat unit of the formula —($CH_2$—$CH_2$—O)—. Further examples of polymers of interest include a polyamide having a molecular weight greater than 1,000 Daltons of the formula —[C(O)—X—C(O)—NH—Y—NH]n- or —[NH—Y—NH—C(O)—X—C(O)]$_n$—, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula —($CH_2$—$CH_2$—O)— or —(O—$CH_2$—$CH_2$)—. The number of such water-soluble repeat units can vary significantly, with the number of such units being from 2 to 500, 2 to 400, 2 to 300, 2 to 200, 2 to 100, 6-100, for example from 2 to 50 or 6 to 50. An example of an embodiment is one in which one or both of X and Y is selected from: —$((CH_2)_{n1}$—$(CH_2$—$CH_2$—$O)_{n2}$—$(CH_2)$— or —$((CH_2)_{n1}$—$(O$—$CH_2$—$CH_2)_{n2}$—$(CH_2)_{n-1}$—), where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is —$(CH_2$—$CH_2)$—, and where Y is —$(CH_2$—$(CH_2$—$CH_2$—$O)_3$—$CH_2$—$CH_2$—$CH_2)$— or —$(CH_2$—$CH_2$—$CH_2$—$(O$—$CH_2$—$CH_2)_3$—$CH_2)$—.

The term modified polymer, such as a modified PEG, refers to water soluble polymers that have been modified or derivatized at either or both terminals, e.g., to include a terminal substituent (e.g., a terminal alkyl, substituted alkyl, alkoxy or substituted alkoxy, etc) and/or a terminal linking functional group (e.g., an amino or carboxylic acid group suitable for attachment via amide bond formation) suitable for attached of the polymer to the multichromophore (e.g., via a branching group). The subject water soluble polymers can be adapted to include any convenient linking groups. It is understood that in some cases, the water soluble polymer can include some dispersity with respect to polymer length, depending on the method of preparation and/or purification of the polymeric starting materials. In some instances, the water soluble polymers are monodisperse.

The water soluble polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The water soluble polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the WSGs disclosed herein.

In some instances, the WSG is a branched non-ionic water soluble group (WSG) that comprises a branching group linked and provides further linkages to two, three or more non-ionic water soluble polymers. In some instances, the branched non-ionic WSG has one of the following formulae:

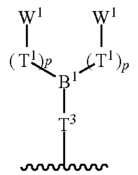

or

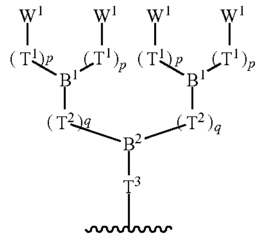

wherein:

each $B^1$ and $B^2$ are independently a branching group;

each $W^1$ is independently a non-ionic water soluble polymer, e.g., comprising 6 or more monomeric units;

$T^3$ is an optional linker to the pendant group or repeat unit of the multichromophore; and each p and q are independently 0 or 1, wherein if present, each $T^1$ and each $T^2$ are independently a linker. In certain instances, each $W^1$ is independently a PEG or modified PEG polymer. In certain instances, each $W^1$ is independently selected from a substituted alkyl, a PEG or modified PEG group and a WSG. In certain instances, each $W^1$ is independently a PEG or modified PEG polymer of 6-30 monomeric units, such as 6-24 or 10-30, 10-24 or 10-20, 12-24, 12-20, 12-16 or 16-20 monomeric units.

In some instances, the branched non-ionic WSG has the following formula:

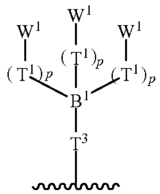

wherein:

each $B^1$ is a branching group;

each $W^1$ is independently a non-ionic water soluble polymer, e.g., comprising 6 or more monomeric units;

$T^3$ is an optional linker to the fused 6-5-6 tricyclic co-monomer; and each p is independently 0 or 1, wherein if present, each $T^1$ is independently a linker. In certain instances, each $W^1$ is independently a PEG or modified PEG polymer. In certain instances, each $W^1$ is independently selected from a substituted alkyl, a PEG or modified PEG group and a WSG. In certain instances, each $W^1$ is independently a PEG or modified PEG polymer of 6-30 monomeric units, such as 6-24 or 10-30, 10-24 or 10-20, 12-24, 12-20, 12-16 or 16-20 monomeric units. In some embodiments of the branched non-ionic WSG, $B^1$ is a tetra-substituted aryl group (e.g., a 1,3,4,5-phenyl).

In some embodiments of the branched non-ionic WSG (e.g., as depicted in the formulae above), $B^1$ is selected from CH, N, C(═O)N, $SO_2N$, a tri-substituted aryl group (e.g., a 1,3,5-phenyl), a tetra-substituted aryl group, and a tri-substituted heteroaryl group. In some embodiments of the branched non-ionic WSG, each p is 0. In some embodiments of the branched non-ionic WSG, p is 1, and each $T^1$ is selected from —$(CH_2)_n$—O—, —O—$(CH_2)_n$—, —$(CH_2)_n$— and —O—, wherein n is from 1 to 12, e.g., 1 to 6. In some embodiments of the branched non-ionic WSG, each $T^2$ and/or $T^3$ is independently a $C_1$-$C_{12}$-alkyl linker, e.g., a $C_1$-$C_6$-alkyl linker, wherein one or more backbone atoms are optionally substituted with a heteroatom.

In some embodiments of the subject multichromophores, the pendant donor chromophore groups are substituted with one or more water solubilizing groups (WSGs) independently selected from the following formulae:

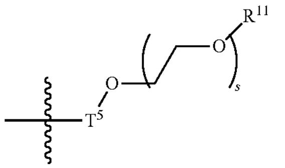

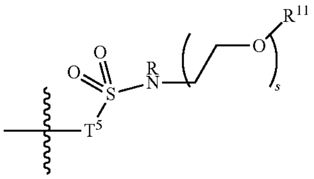

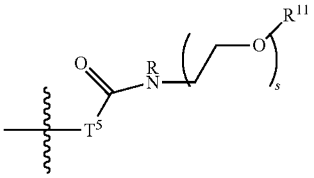

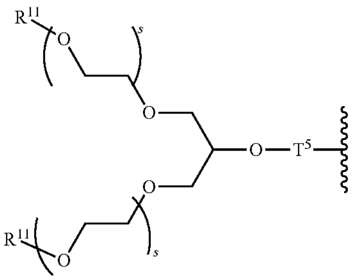

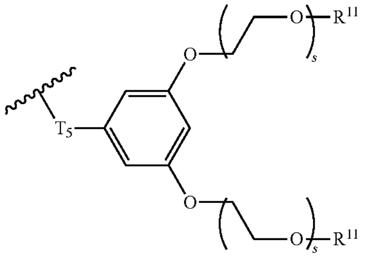

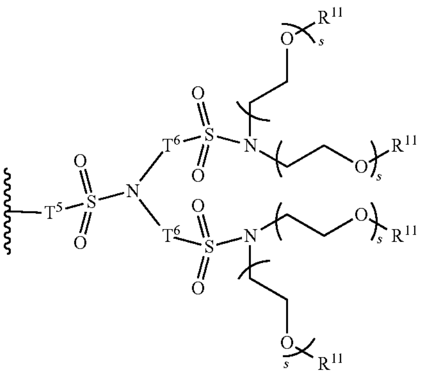

-continued

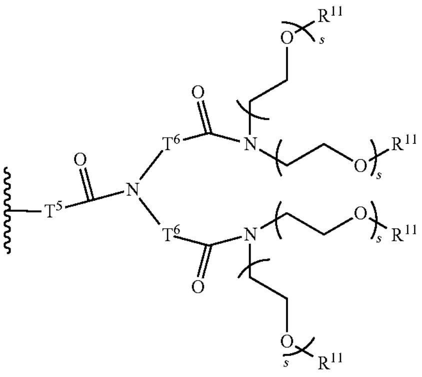

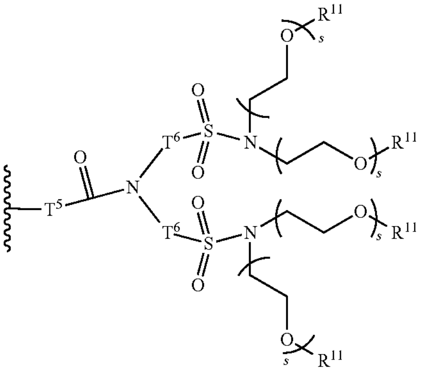

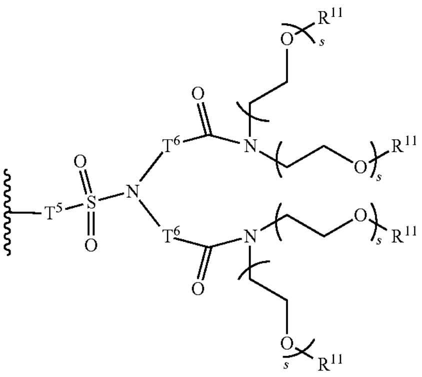

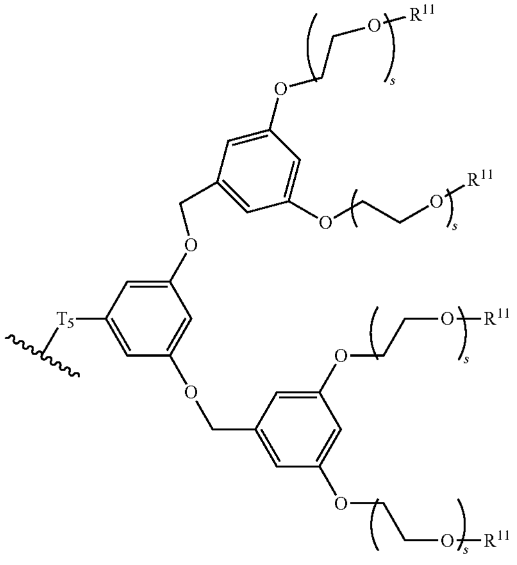

-continued

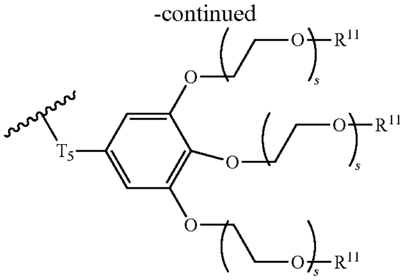

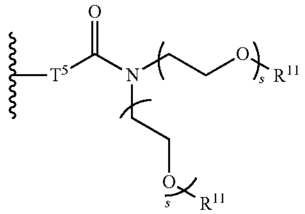

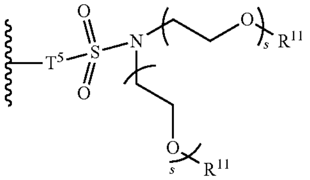

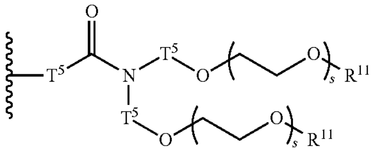

wherein:

$T^5$ is an optional linker;

each $T^6$ is an linker;

$R^{11}$ and R are independently H, alkyl or substituted alkyl; and each s is an integer from 1 to 100 (e.g., 6 to 100 or 6 to 50).

In certain instances, each s is independently 6 to 30, such as 6 to 24, 6 to 20, 11 to 20, 12 to 20, 12 to 18 or 12 to 16. In certain instances, each s is independently 6 to 30, such as 6 to 24, 8 to 24, 10 to 24, 12 to 24, 13 to 24, 14 to 24, 15 to 22 or 16 to 20. In some cases, each s is independently 11, 12, 13, 14, 15, 16, 17, 18, 19, 20, 21, 22, 23 or 24. In some embodiments, each s is independently 7 or more, such as 8, 9 or more, 10 or more, 11 or more, 12 or more, 13 or more, 14 or more, 15 or more, or even more, and in some cases, have up to 50 monomeric units, such as up to 40, up to 30 or up to 24 monomeric units. In some instances, each s is independently 6-30 monomeric units, such as 6-24 or 10-30, 10-24 or 10-20, 12-24, 12-20, 12-16 or 16-20 monomeric units. In some cases, each s is the same. In some embodiments of the WSG, $T^5$ and/or $T^6$ is a $C_1$-$C_{12}$-alkyl linker, e.g., a $C_1$-$C_6$-alkyl linker, wherein one or more backbone atoms are optionally substituted with a heteroatom (e.g., an —O—). In some embodiments of the WSG, each $R^{11}$ is H. In some embodiments of the WSG, each $R^{11}$ is methyl.

It is understood that hydroxy-terminated PEG chains instead of methoxy-terminated PEG chains may be utilized in any of the WSG groups described above. In certain instances of any one of the formulae described herein, one or more of the repeat units or pendant groups is substituted with a WSG that is a dendron selected from one of the following structures:

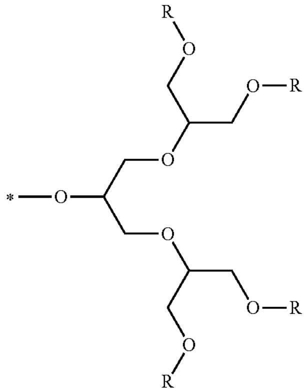

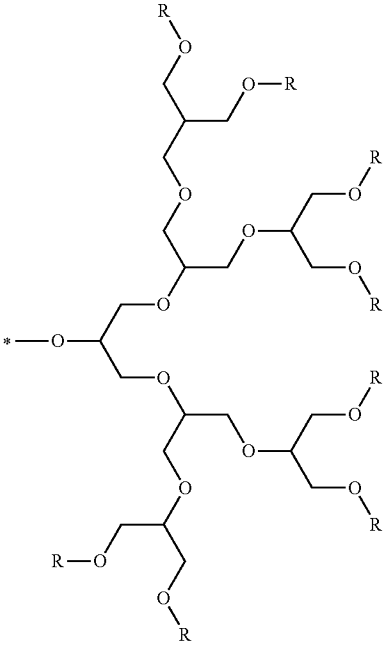

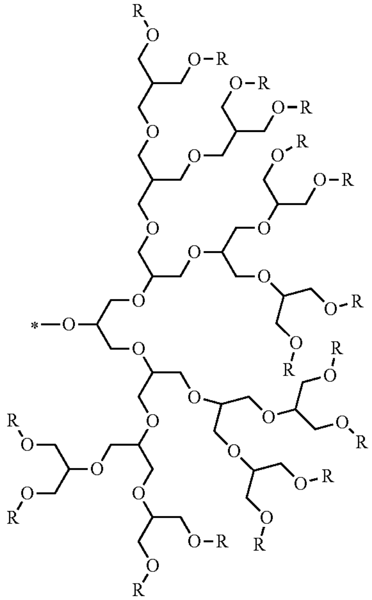

-continued

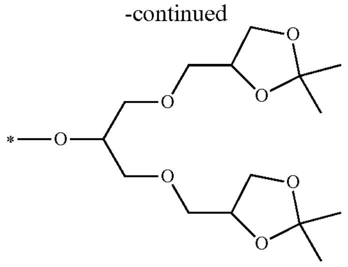

(and higher generations)

where R = H, $CH_3$

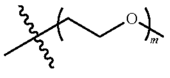

m = 1-16

In certain instances of any one of the formulae described herein, one or more of the repeat units or pendant groups is substituted with a WSG that is a polyol selected from one of the following structures:

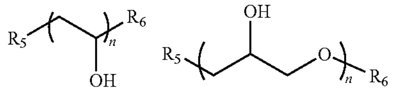

n = 1-50

$R_5$ =

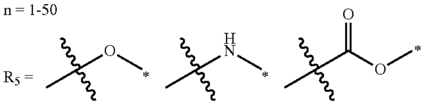

$R_6$ = H

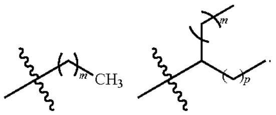

m,p=0-10

In certain instances of any one of the formulae described herein, one or more of the repeat units or pendant groups is substituted with WSG that is an oxazoline of the following

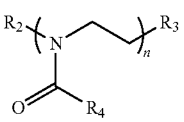

n = 1-50

$R_2$, $R_4$ = H

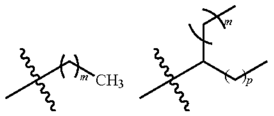

m, p = 0-10 structure:

$R_3$ =

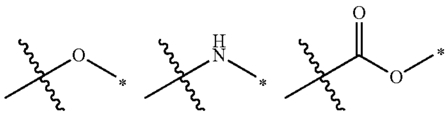

In certain instances of any one of the formulae described herein, one or more of the repeat units or pendant groups is substituted with a WSG that is a peptoid selected from one of the following structures:

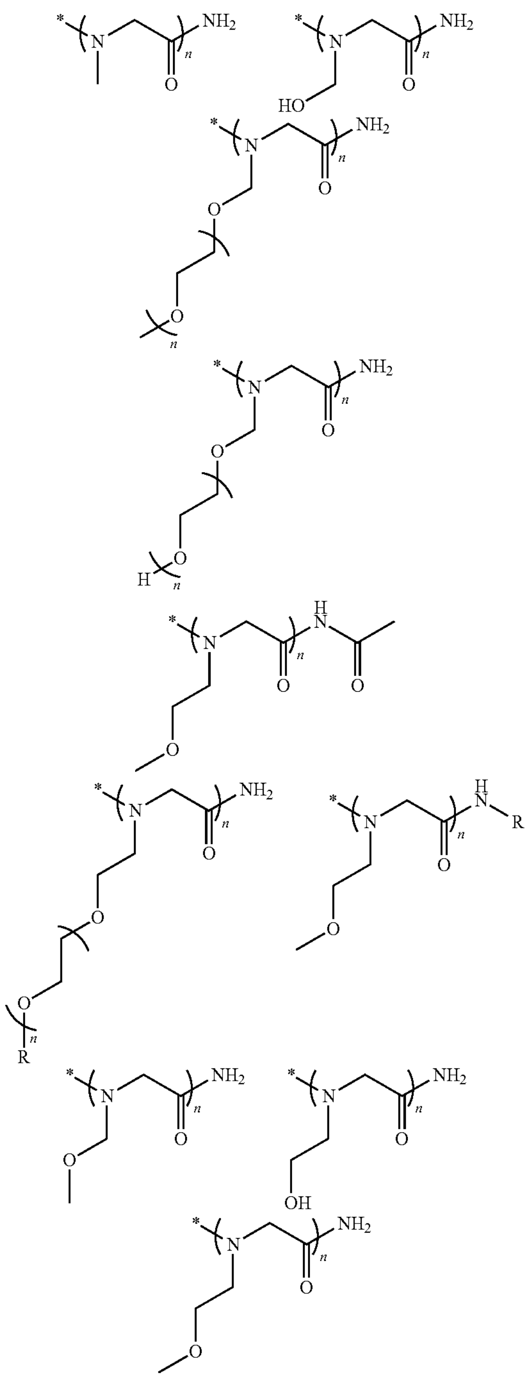

R. H, Me, Ac,

The water soluble group (WSG) can be capable of imparting solubility in water in excess of 10 mg/mL to the multichromophore or polymeric tandem dye, such as in excess of 20 mg/mL, in excess of 30 mg/mL, in excess of 40 mg/mL, in excess of 50 mg/mL, in excess of 60 mg/mL, in excess of 70 mg/mL, in excess of 80 mg/mL, in excess of 90 mg/mL or in excess of 100 mg/mL. In certain cases, the branched non-ionic water soluble group (WSG) is capable of imparting solubility in water (e.g., an aqueous buffer) of 20 mg/mL or more to the multichromophore or polymeric tandem dye, such as 30 mg/mL or more, 40 mg/mL or more, 50 mg/mL or more, 60 mg/mL or more, 70 mg/mL or more, 80 mg/mL or more, 90 mg/mL or more, 100 mg/mL or more, or even more. It is understood that water soluble multichromophores may, under certain conditions, form discrete water solvated nanoparticles in aqueous systems. In certain cases, the water solvated nanoparticles are resistant to aggregation and find use in a variety of biological assays.

The polymeric backbone of the multichromophore may have any convenient length. In some cases, the particular number of monomeric repeat units of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the polymeric backbone of the multichromophore may fall within the range of 2 to 1,000, such as 2 to 500, 2 to 500, 3 to 500, 4 to 500, 5 to 500, 6 to 500, 7 to 500, 8 to 500, 9 to 500, 10 to 500, 10 to 400, 10 to 300, 10 to 200, 10 to 100, or 20 to 100 units or segments.

The multichromophore may be of any convenient molecular weight (MW). In some cases, the MW of the multichromophore may be expressed as an average molecular weight. In some instances, the polymeric dye has an average molecular weight in the range of 500 to 500,000, such as from 1,000 to 100,000, from 2,000 to 100,000 (e.g., from 2,000 to 10,000 or from 10,000 to 100,000) or even an average molecular weight in the range of 50,000 to 100,000. In some cases, the polymeric backbone of the multichromophore is prepared having a particular, discrete sequence of monomers such that the MW of the multichromophore may be expressed as an exact molecular weight. In some instances, the polymeric dye has an exact molecular weight in the range of 500 to 500,000, such as from 1,000 to 100,000, from 1,000 to 50,000, from 2,000 to 50,000 (e.g., from 2,000 to 10,000 or from 10,000 to 50,000) or even an average molecular weight in the range of 50,000 to 100,000.

Polymeric Tandem Dyes

As summarized above, the subject light harvesting multichromophore can include a polymeric backbone of non-conjugated repeat units including a plurality of pendant donor chromophore groups, which groups can each be linked to one of the repeat units. As described above, the subject water soluble light harvesting multichromophores are capable of homo-energy transfer between pendant donor chromophores which can lead to continuous reversible energy transfer amongst equal chromophores rather than emission from a single chromophore. As such, although the multichromophore system can itself be fluorescent, via the process of self-quenching illustrated in FIG. 6A, the multichromophore system can have quantum yields that are significantly lower than those observed for a single isolated chromophore.

The water soluble light harvesting multichromophore is capable of transferring energy to a linked acceptor fluorophore. See e.g., FIG. 6B. As such, the subject polymeric tandem dyes further include a covalently linked acceptor signaling fluorophore in energy-receiving proximity to the donor water solvated light harvesting multichromophore system, i.e., in energy-receiving proximity to at least one pendant donor chromophore group. The terms "acceptor fluorophore" and "acceptor chromophore" are used interchangeably herein.

The acceptor signaling fluorophore can be linked to a non-conjugated repeat unit of the polymeric backbone as a pendant group. Excitation of the multichromophore donor can leads to energy transfer to, and emission from, the covalently attached acceptor signaling fluorophore. The number of repeat units of the donor water solvated light harvesting multichromophore having linked acceptor signaling fluorophore groups may vary, where in some instances the number ranges from 1 mol % to 50 mol % of the repeat units, such as from 1 mol % to 25 mol %, 2 mol % to 25 mol %, 3 mol % to 25 mol %, 4 mol % to 25 mol %, 5 mol % to 25 mol % or from 10 mol % to 25 mol %.

Mechanisms for energy transfer between the light harvesting chromophores of the multichromophore and from these donor chromophores to a linked acceptor signaling fluorophore include, for example, resonant energy transfer (e.g., Förster (or fluorescence) resonance energy transfer, FRET), quantum charge exchange (Dexter energy transfer) and the like. These energy transfer mechanisms can be relatively short range; that is, close proximity of chromophores of the light harvesting multichromophore system to each other and/or to an acceptor fluorophore provides for efficient energy transfer.

Under conditions for efficient energy transfer, amplification of the emission from the acceptor fluorophore can occur where the emission from the luminescent acceptor fluorophore is more intense when the incident light (the "pump light") is at a wavelength which is absorbed by, and transferred from, the chromophores of the light harvesting multichromophore than when the luminescent acceptor fluorophore is directly excited by the pump light.

By "efficient" energy transfer is meant 10% or more, such as 20% or more or 30% or more, 40% or more, 50% or more, of the energy harvested by the donor chromophores is transferred to the acceptor. By "amplification" is meant that the signal from the acceptor fluorophore is 1.5× or greater when excited by energy transfer from the donor light harvesting multichromophore system as compared to direct excitation of the acceptor fluorophore with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the polymeric tandem dye, the acceptor fluorophore emission is 1.5 fold greater or more when excited by the multichromophore as compared to direct excitation of the acceptor fluorophore with incident light, such as 2-fold or greater, 3-fold or greater, 4-fold or greater, 5-fold or greater, 6-fold or greater, 8-fold or greater, 10-fold or greater, 20-fold or greater, 50-fold or greater, 100-fold or greater, or even greater as compared to direct excitation of the acceptor fluorophore with incident light.

Any convenient fluorescent dyes may be utilized in the polymeric tandem dyes as an acceptor fluorophore. The terms "fluorescent dye" and "fluorophore" are used interchangeably herein. The acceptor fluorophore (e.g., each $A^1$) can be a small molecule fluorophore. The acceptor fluorophore (e.g., each $A^1$) can be a dye molecule selected from a rhodamine, a coumarin, a xanthene, a cyanine, a polymethine, a pyrene, a thiazine, an acridine, a dipyrromethene borondifluoride, a napthalimide, a phycobiliprotein, a peridinum chlorophyll protein, conjugates thereof, and combinations thereof. In certain embodiments, the acceptor fluorophore ($A^1$) is a cyanine dye, a xanthene dye, a coumarin dye, a thiazine dye or an acridine dye. In some instances, the acceptor fluorophore ($A^1$) is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. Fluorescent dyes of interest include, but are not limited to, fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a multichromophore linked to an acceptor fluorophore selected from Cy3, Cy3.5, Cy5, Cy5.5, Cy7, Alexa488, Alexa 647 and Alexa700. In certain embodiments, the polymeric tandem dye includes a multichromophore linked to an acceptor fluorophore selected from Dyomics dyes (such as DY 431, DY 485XL, DY 500XL, DY 530, DY 610, DY 633, DY 640, DY 651, DY 654, DY 682, DY 700, DY 701, DY 704, DY 730, DY 731, DY 732, DY 734, DY 752, DY 754, DY 778, DY 782, DY 800 or DY 831), Biotium CF 555, Cy 3.5, and diethylamino coumarin.

In some instances, the acceptor fluorophore is a BODIPY group, e.g., a BODIPY group of any one of formula (XI)-(XIXa) or any embodiment thereof described herein. It is understood that any convenient BODIPY group described herein having a suitable absorption and emission profile can be configured as an acceptor fluorophore in energy receiving proximity to the donor water solvated light harvesting multichromophore system, i.e., in energy-receiving proximity to at least one compatible pendant donor chromophore group.

In some embodiments, the acceptor fluorophore that is selected has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of signaling chromophore of interest include, but are not limited to: 395 nm±5 nm, 420 nm±5 nm, 430 nm±5 nm, 440 nm±5 nm, 450 nm±5 nm, 460 nm±5 nm, 470 nm±5 nm, 480 nm±5 nm, 490 nm±5 nm, 500 nm±5 nm, 510 nm±5 nm, 520 nm±5 nm, 530 nm±5 nm, 540 nm±5 nm, 550 nm±5 nm, 560 nm±5 nm, 570 nm±5 nm, 580 nm±5 nm, 590 nm±5 nm, 605 nm±5 nm, 650 nm±5 nm, 680 nm±5 nm, 700 nm±5 nm, 805 nm±5 nm.

The linked luminescent acceptor fluorophore emission of the polymeric tandem dye can have a quantum yield of 0.03 or more, such as a quantum yield of 0.04 or more, 0.05 or more, 0.06 or more, 0.07 or more, 0.08 or more, 0.09 or more, 0.1 or more, 0.15 or more, 0.2 or more, 0.3 or more or even more. In some instances, the polymeric tandem dye has an extinction coefficient of $5\times10^5$ $cm^{-1}M^{-1}$ or more, such as $6\times10^5$ $cm^{-1}M^{-1}$ or more, $7\times10^5$ $cm^{-1}M^{-1}$ or more, $8\times10^5$ $cm^{-1}M^{-1}$ or more, $9\times10^5$ $cm^{-1}M^{-1}$ or more, such as $1\times10^6$ $cm^{-1}M^{-1}$ or more, $1.5\times10^6$ $cm^{-1}M^{-1}$ or more, $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $cm^{-1}M^{-1}$ or more, $5\times10^6$ $cm^{-1}M^{-1}$ or more, $6\times10^6$ $cm^{-1}M^{-1}$ or more, $7\times10^6$ $cm^{-1}M^{-1}$ or more, or $8\times10^6$ $cm^{-1}M^{-1}$ or more. In some embodiments, the polymeric tandem dye has a molar extinction coefficient of $5\times10^5$ $M^{-1}$ $cm^{-1}$ or more. In certain embodiments, the polymeric tandem dye has a molar extinction coefficient of $1\times10^6$ $M^{-1}$ $cm^{-1}$ or more.

The subject polymeric tandem dyes can provide for fluorescence emissions from luminescent signaling chromophore dyes that are brighter than the emissions which are possible from such luminescent dyes in isolation. The linked luminescent signaling chromophore emission of the polymeric tandem dye can have a brightness of 50 $mM^{-1}$ $cm^{-1}$ or more, such as 60 $mM^{-1}$ $cm^{-1}$ or more, 70 $mM^{-1}$ $cm^{-1}$ or more, 80 $mM^{-1}$ $cm^{-1}$ or more, 90 $mM^{-1}$ $cm^{-1}$ or more, 100 $mM^{-1}$ $cm^{-1}$ or more, 150 $mM^{-1}$ $cm^{-1}$ or more, 200 $mM^{-1}$ $cm^{-1}$ or more, 250 $mM^{-1}$ $cm^{-1}$ or more, 300 $mM^{-1}$ $cm^{-1}$ or more, or even more. In certain instances, the linked signaling chromophore emission of the polymeric tandem dye has a brightness that is at least 5-fold greater than the brightness of a directly excited luminescent dye, such as at least 10-fold greater, at least 20-fold greater, at least 30-fold greater, at least 50-fold greater, at least 100-fold greater, at least 300-fold greater, or even greater than the brightness of a directly excited luminescent dye.

The subject polymeric tandem dyes can provide for fluorescence emissions having a Stokes shift of 100 nm or more, such as 110 nm or more, 120 nm or more, 130 nm or more, 140 nm or more, or 150 nm or more. In some cases, the Stokes shift is 300 nm or less, such as 200 nm or less.

In some embodiments, a polymeric tandem dye includes a water soluble light harvesting multichromophore of any one of formulae (I)-(IX), where the $Z^1$ chemoselective tag is replaced with an acceptor fluorophore group ($A^1$). It is understood that any of the embodiments of the subject multichromophores of formulae (I)-(IX) can also be practiced for a polymeric tandem dye of the present disclosure. In certain instances of the formulae (I)-(IX), one or more of the $Z^1$ groups can be conjugated to an acceptor fluorophore precursor to provide an acceptor fluorophore group ($A^1$). As such, the polymeric tandem dye can include a segment of the formula (Ia):

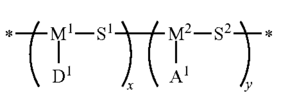

(Ia)

wherein:

each $M^1$ and $M^2$ is independently an unsaturated co-monomer (e.g., an aryl or heteroaryl co-monomer);

each $S^1$ and $S^2$ is independently a non-conjugated spacer unit;

each $D^1$ is independently a pendant donor chromophore (e.g., as described herein) linked to $M^1$;

each $A^1$ is independently an acceptor fluorophore linked to $M^2$;

x is 75 mol % or more; and y is 25 mol % or less.

The first ($M^1$-$S^1$) and second repeat units ($M^2$-$S^2$) can be arranged in a random or co-block configuration. In certain cases of formula (Ia), the $D^1$ pendant groups of the first repeat units include two or more (e.g., two or three) distinct types of pendant light absorbing chromophores that together provide a light harvesting multichromophore system. In certain instances of formula (Ia), the $D^1$ pendant groups of the first repeat units are all the same.

In some instances of formula (Ia), x is 80 mol % or more, such as 85 mol % or more, 90 mol % or more, 95 mol % or more, 96 mol % or more, 97 mol % or more, 98 mol % or more, or 99 mol % or more. In some instances of formula (Ia), y is 20 mol % or less, such as 15 mol % or less, 10 mol % or less, 5 mol % or less, 4 mol % or less, 3 mol % or less, 2 mol % or less, 1 mol % or less.

In some instances, the polymeric tandem dye includes a segment of formula (IIa):

(IIa)

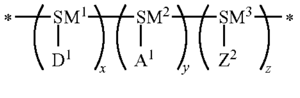

wherein:

- the polymeric backbone of non-conjugated repeat units comprises $SM^1$, $SM^2$ and $SM^3$ co-monomers that are each independently a non-conjugated co-monomer;
- each $D^1$ is independently a pendant donor chromophore linked to $SM^1$;
- each $A^1$ is independently an acceptor fluorophore linked to $SM^2$;
- each $Z^2$ is an optional sidechain group linked to $SM^3$;
- x is 50 mol % or more; and
- y+z is 50 mol % or less.

$Z^2$ can be absent or any convenient sidechain group, such as a light absorbing chromophore, a chemoselective tag, a linker, a linked biomolecule, a acceptor fluorophore, a WSG, etc. In certain cases of formula (IIa), $SM^3$ is a spacer co-monomer where $Z^2$ is absent. In certain instances of formula (IIa), $SM^3$ is a co-monomer including a $Z^2$ group that is a second pendant light absorbing chromophore, where each $D^1$ and each $Z^2$ together provide a light harvesting multichromophore system. In some cases, $SM^3$ is a co-monomer including a second chemoselective tag ($Z^2$), e.g., a protected functional group or a tag that is orthogonal to $Z^1$ that provides for the selective installation of a moiety of interest.

In certain cases of formula (IIa), x is 60 mol % or more, such as 65 mol % or more, 70 mol % or more, 75 mol % or more, 80 mol % or more, 85 mol % or more, 90 mol % or more, 95 mol % or more, or even more. In certain instances of formula (IIa), y+z is 40 mol % or less, such as 30 mol % or less, 25 mol % or less, 20 mol % or less, 15 mol % or less, 10 mol % or less, 5 mol % or less, or even less. In certain instances of formula (IIa), y is at least 1 mol % and 25 mol % or less, such as 20 mol % or less, 15 mol % or less, 10 mol % or less, 5 mol % or less, or even less. In certain instances of formula (IIa), z is at least 1 mol % and 10 mol % or less, such as 5 mol % or less, or even less.

In some instances, the polymeric tandem dye includes a segment of formula (IIIa):

(IIIa)

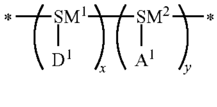

wherein:

- the polymeric backbone of non-conjugated repeat units comprises $SM^1$ and $SM^2$ co-monomers that are each independently a non-conjugated co-monomer;
- each $D^1$ is independently a pendant donor chromophore linked to $SM^1$;
- each $A^1$ is independently an acceptor fluorophore linked to $SM^2$;
- x is 75 mol % or more; and
- y is 25 mol % or less.

In certain embodiments of formula (IIIa), $SM^1$ and $SM^2$ are each independently a saturated non-conjugated co-monomer, e.g., a co-monomer providing only single covalent C—C bonds. In some embodiments of formula (IIIa), $SM^1$ and $SM^2$ are each independently a partially saturated non-conjugated co-monomer, e.g., a co-monomer providing an isolated double C═C covalent bond in a backbone of saturated covalent bonds. The first and second repeat units ($SM^1$ and $SM^2$) of formula (IIIa) can be arranged in a random configuration, a block or co-block configuration, or in a particular sequence. In certain cases of formula (IIIa), the $D^1$ pendant groups of the $SM^1$ include two or more (e.g., two or three) distinct types of pendant light absorbing chromophores that together provide a light harvesting multichromophore system. In certain instances of formula (IIIa), the $D^1$ pendant groups of the first repeat units are all the same.

In some instances of formula (IIIa), x is 80 mol % or more, such as 85 mol % or more, 90 mol % or more, 95 mol % or more, 96 mol % or more, 97 mol % or more, 98 mol % or more, or 99 mol % or more. In some instances of formula (IIIa), y is 20 mol % or less, such as 15 mol % or less, 10 mol % or less, 5 mol % or less, 4 mol % or less, 3 mol % or less, 2 mol % or less, 1 mol % or less.

In certain instances, the polymeric tandem dye is of formula (IVa):

(IVa)

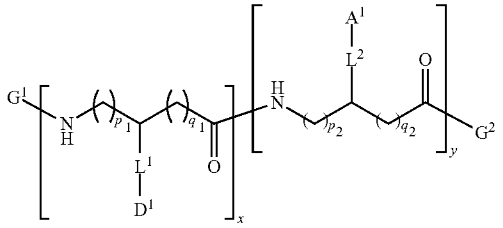

wherein:

- each $D^1$ is independently a pendant donor chromophore group;
- each $A^1$ is independently an acceptor fluorophore;
- each $L^1$ and $L^2$ are independently a linker;
- $p_1$ and $q_1$ are independently 0 or 1 wherein $p_1+q_1 \leq 1$;
- $p_2$ and $q_2$ are independently 0 or 1 wherein $p_1+q_1 \leq 1$;
- x is 75 mol % or more;
- y is 25 mol % or less; and
- $G^1$ and $G^2$ are each independently selected from a terminal group, a polymer segment, a light absorbing (e.g., donor) chromophore group, an acceptor fluorophore, a linker and a linked specific binding member.

In some embodiments of formula (IVa), $p_1$ and $p_2$ are each 0 and $q_1$ and $q_2$ are each 1 (e.g., β3-amino acid residues). In some embodiments of formula (IVa), $p_1$ and $p_2$ are each 1 and $q_1$ and $q_2$ are each 0 (e.g., β2-amino acid residues). In some cases, $p_1$, $p_2$, $q_1$ and $q_2$ are each 0 and the polymeric tandem dye is of formula (Va):

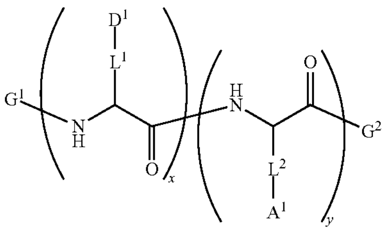

wherein:

each $D^1$ is independently a pendant donor chromophore group;

each $A^1$ is independently an acceptor fluorophore;

$L^1$ and $L^2$ are each independently a linker;

x is 75 mol % or more;

y is 25 mol % or less; and $G^1$ and $G^2$ are each independently selected from a terminal group, a polymer segment, a light absorbing (e.g., donor) chromophore group, a linker and a linked specific binding member. It is understood that the multichromophores described by formula (Va) include any convenient arrangements of co-monomers in a defined linear sequence, which have in total the defined mol % ratios of x and y. In some cases, the $A^1$ containing co-monomers are spaced throughout the sequence of the polymeric backbone and as such are always flanked on both sides by one or more D1 containing co-monomers.

In certain instances of formula (Va), the polymeric tandem dye includes a segment of formula (VIa):

(VIa)

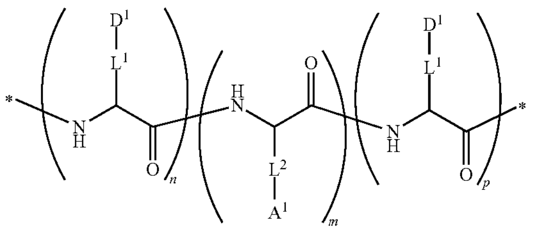

wherein:

each $D^1$ is independently a pendant donor chromophore group;

each $A^1$ is independently an acceptor chromophore;

each $L^1$ and $L^2$ are independently a linker;

n and p are each independently an integer from 1 to 20 wherein n+p≥2; and m is 1 or 2.

In some cases of formula (VIa), n and p are each independently 1 to 10 such as 2 to 20, 3 to 10 or 3 to 6. In some instances of formula (VIa), n+p is an integer from 2 to 20, such as 3 to 20, 4 to 20, 5 to 20, 5 to 15 or 5 to 12. In certain embodiments of formula (VIa), m is 1.

The subject polymeric tandem dyes can include multiple segments of formula (VIa) where each segment includes one isolated $A^1$ containing co-monomers flanked by blocks of $D^1$ containing co-monomers. In some cases, the multichromophore includes two or more segments of formula (VIa) located directed adjacent to each other to provide two isolated $A^1$ containing co-monomers separated by a block of 2-20 $D^1$ containing co-monomers, such as a block of 3 to 20, 4 to 20, 5 to 20, 5 to 15 or 5 to 12 $D^1$ containing co-monomers. As such, in certain embodiments, the polymeric tandem dye includes q segments of a block copolymer and is of formula (VIIa):

(VIIa)

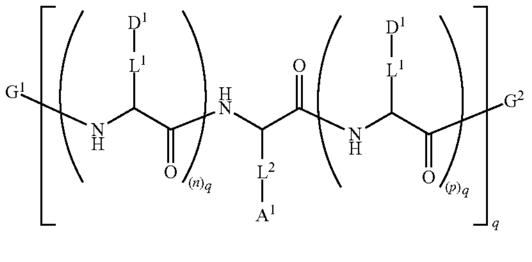

wherein: each $(n)_q$ and each $(p)_q$ is independently an integer from 1 to 20, wherein for each of the q segments $(n)_q+(p)_q \geq 3$; and q is an integer from 1 to 100.

In certain embodiments, the polymeric tandem dye has the formula (VIIIa):

(VIIIa)

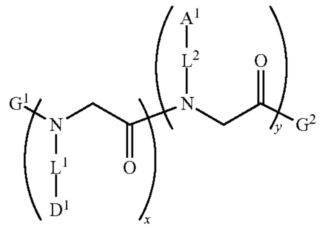

wherein each $D^1$ is independently a pendant donor chromophore group;

each $A^1$ is independently an acceptor chromophore;

each $L^1$ and $L^2$ is independently a linker;

x is 75 mol % or more;

y is 25 mol % or less; and $G^1$ and $G^2$ are each independently selected from a terminal group, a polymer segment, a donor chromophore group, a linker and a linked specific binding member.

In certain embodiments, the polymeric tandem dye has the formula (IXa):

(IXa)

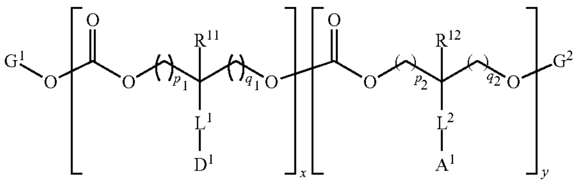

wherein:

each $D^1$ is independently a pendant BODIPY donor chromophore;

each $A^1$ is independently an acceptor fluorophore;

each $L^1$ and $L^2$ is independently a linker;

x is 75 mol % or more;

y is 25 mol % or less; and $G^1$ and $G^2$ are each independently selected from the group consisting of a terminal group, a polymer segment, a donor chromophore group, an acceptor fluorophore, a linker and a linked specific binding member.

In some instances of formulae (IVa), (Va), (XIIIa) and (IXa), x is 80 mol % or more, such as 85 mol % or more, 90 mol % or more, 95 mol % or more, 96 mol % or more, 97 mol % or more, 98 mol % or more, or 99 mol % or more. In some instances of formula (IV), (V), (XIII) and (IX), y is 20 mol % or less, such as 15 mol % or less, 10 mol % or less, 5 mol % or less, 4 mol % or less, 3 mol % or less, 2 mol % or less, 1 mol % or less.

In certain embodiments, the polymeric tandem dye has the formula (Xa):

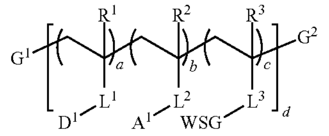

wherein:

each $D^1$ is independently a pendant donor chromophore;

each $A^1$ is independently an acceptor fluorophore;

each $L^1$, $L^2$ and $L^3$ is independently a linker;

a, b and c are mol % values for each co-monomer;

d represents the total polymerization or average length of the polymer (e.g., d is 2-1000, such as 2-500, 2-200, 2-100 or 2-50);

WSG is a water solubilizing group (e.g., as described herein); and $G^1$ and $G^2$ are each independently selected from the group consisting of a terminal group, a polymer segment, a donor chromophore group, an acceptor fluorophore, a linker and a linked specific binding member.

In some instances of formula (Xa), c=0. In some instances of formula (Xa), a>0 and b>0. In some instances of formula (Xa), a is 80 mol % or more, such as 85 mol % or more, 90 mol % or more, 95 mol % or more, 96 mol % or more, 97 mol % or more, 98 mol % or more, or 99 mol % or more. In some instances of formula (Xa), b is 20 mol % or less, such as 15 mol % or less, 10 mol % or less, 5 mol % or less, 4 mol % or less, 3 mol % or less, 2 mol % or less, 1 mol % or less. In some instances of formula (Xa), a is 65-95 mol %, b is 5-35 mol % and c is 0-30 mol %, where a+b+c=100%.

In certain instances of formula (Xa), each $D^1$ is a linked BODIPY group (e.g., as described herein). In some cases, each acceptor dye $A^1$ is chosen from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, iFluor dyes 350, 405, 488, 514, 532, 594, 660, 680, 700, 710, 790, Tide Fluor dyes 5WS, 7WS, 8ws, ICG, BODIPY-based dyes, Biotium CF 555, Cy 3.5 and diethylamino coumarin. In certain instances of formula (Xa), $L^1$-$D^1$ is selected from the following:

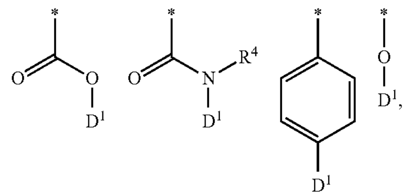

where $R^4$ is H, lower alkyl, substituted lower alkyl and WSG.

Alternatively, in some cases of formula (Xa), pairs of donor and acceptor dyes $D^1$ and $A^1$ can be chosen from the following: Dyomics dyes DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, iFluor dyes 350, 405, 488, 514, 532, 594, 660, 680, 700, 710, 790, Tide Fluor dyes 5WS, 7WS, 8ws, ICG, BODIPY-based dyes, Biotium CF 555, Cy 3.5 and diethylamino coumarin. In certain instances of formula (Xa), the WSG is a water solubilizing group as described in any one of the embodiments and structures of such groups described herein.

In certain instances, the polymeric tandem dye is derived from a multichromophore of formula (XXI), wherein the chemoselective tag $Z^1$ of $SM^2$ is conjugated to an acceptor fluorophore. As such, exemplary polymeric tandem dye structures are shown in Example 3 of the experimental section and in the following structures:

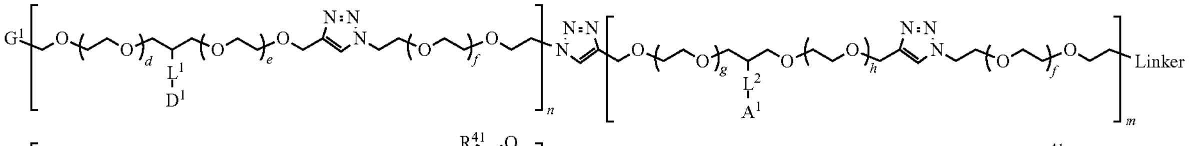

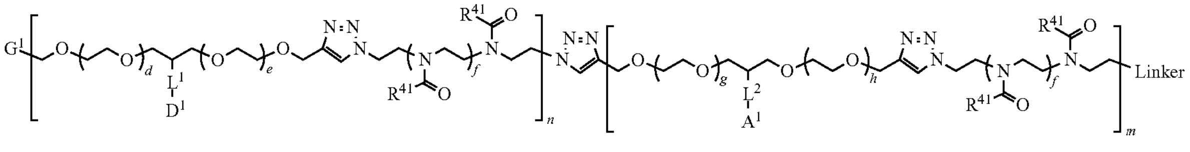

wherein:

$G^1$ is a terminal group (e.g., as described herein);

$L^1$ and $L^2$ are independently a linker;

$D^1$ is a pendant chromophore (e.g., as described herein);

$A^1$ is an acceptor fluorophore;

each d, e, f, g and h are independently 1-6;

each n and m is independently 1-1000 (e.g., 2-1000, 2-500, 2-100 or 2-50);

each $R^{41}$ is selected from alkyl, substituted alkyl and WSG; and

"Linker" is a linker including an optional chemoselective functional group, e.g., for conjugation to a co-monomer or a biomolecule. In certain instance, each $D^1$ is a BODIPY chromophore group (e.g., as described herein). In some instances, the polymeric tandem dye derived from formula (XXI) is described by the following general structure:

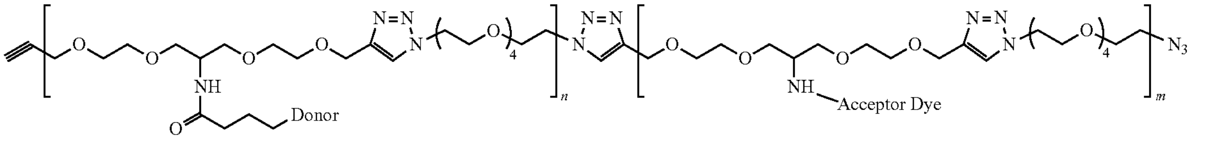

where each n and m is independently 1-1000 (e.g., 2-1000, 2-500, 2-100 or 2-50). In some cases, the donor chromophore is a BODIPY chromophore (e.g., as described herein), and the acceptor dye is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, iFluor dyes 350, 405, 488, 514, 532, 594, 660, 680, 700, 710, 790, Tide Fluor dyes 5WS, 7WS, 8ws, ICG, BODIPY-based dyes, Biotium CF 555, Cy 3.5 and diethylamino coumarin.

Labelled Specific Binding Members

Aspects of the present disclosure include labelled specific binding members. A labelled specific binding member is a conjugate of a subject polymeric dye (e.g., as described herein) and a specific binding member. Any of the polymeric dyes or polymeric tandem dyes described herein may be conjugated to a specific binding member. The specific binding member and the polymeric dye can be conjugated (e.g., covalently linked) to each other at any convenient locations of the two molecules, via an optional linker. In some embodiments, the labelled specific binding member is aggregation resistant. As used herein, by "aggregation-resistant" is meant a labelled specific binding member capable of forming a homogenous aqueous composition without aggregated precipitate at a concentration of 1 mg/ml or more in an aqueous buffer of interest, such as 2 mg/ml or more, 3 mg/ml or more, 4 mg/ml or more, 5 mg/ml or more, 6 mg/ml or more, 7 mg/ml or more, 8 mg/ml or more, 9 mg/ml or more, 10 mg/mL or more or even more of the labelled specific binding member.

In certain embodiments, the labelled specific binding member comprises: a water solvated polymeric dye having a deep ultraviolet excitation spectrum and comprising a segment of π-conjugated co-monomers and a conjugation-modifying repeat unit; and a specific binding member covalently linked to the multichromophore.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus, the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10\times10^{-9}$ M or less, such as $1\times10^{-9}$ M or less, $3\times10^{-10}$ M or less, $1\times10^{-10}$ M or less, $3\times10^{-11}$ M or less, $1\times10^{-11}$ M or less, $3\times10^{-12}$ M or less or $1\times10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a $F(ab')_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In some embodiments, the labelled specific binding member includes: a water solvated light harvesting multichromophore (e.g., as described herein); and a signaling chromophore covalently linked to the multichromophore in energy-receiving proximity therewith (e.g., as described herein); and a specific binding member covalently linked to the multichromophore. In some instances of the labelled specific binding member, the multichromophore of any of the formula described herein, wherein: $G^1$ and $G^2$ are each independently selected from the group consisting of a terminal group (e.g., end group), a linker and a linked specific binding member, wherein at least one of $G^1$ and $G^2$ is a linked specific binding member.

In certain embodiments of the formulae described herein, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags (e.g., as described herein) that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In certain embodiments, a carboxylic acid functional group or derivative thereof is included at $G^1$ and/or $G^2$ and an amino functional group or derivative thereof is included at $Z^2$.

In some embodiments of the formulae described herein, at least one of $G^1$ and $G^2$ is $-L^3-Z^4$ where $L^3$ is a linker (e.g., as described herein) and $Z^4$ is a specific binding member (e.g., as described herein). In some embodiments of formulae described herein, at least one of $G^1$ and $G^2$ is $-L^3-Z^3$ where $L^3$ is a linker (e.g., as described herein) and $Z^3$ is a chemoselective tag (e.g., as described herein). Any convenient chemoselective tag and conjugation chemistries can be adapted for use in the subject multichromophores. Chemoselective tags of interest include, but are not limited to, amine, active ester, maleimide, thiol, sulfur(VI) fluoride exchange chemistry (SuFEX), sulfonyl fluoride, Diers Alder cycloaddition click reagents and click chemistry, tetrazine, transcyclooctene, aldehyde, alkoxylamine, alkynes, cyclooctynes, azide, and the like. In some instances, $Z^3$ is selected from the group consisting of carboxylic acid, active ester (e.g., N-hydroxy succinimidyl ester (NHS) or sulfo-NHS), amino, maleimide, iodoacetyl and thiol.

Biomolecules of interest include, but are not limited to, polypeptides, polynucleotides, carbohydrates, fatty acids, steroids, purines, pyrimidines, derivatives, structural analogs thereof and combinations thereof. In certain instances, $Z^4$ is an antibody. In some instances, $Z^4$ is an antibody fragment or binding derivative thereof. In some cases, the antibody fragment or binding derivative thereof is selected from the group consisting of a Fab fragment, a $F(ab')_2$ fragment, a scFv, a diabody and a triabody.

Methods of Use

As summarized above, aspects of the present disclosure include methods of evaluating a sample for the presence of a target analyte. Aspects of the method include contacting the sample with a polymeric dye conjugate that specifically binds the target analyte to produce a labelling composition contacted sample. As used herein, the terms "polymeric dye conjugate" and "labelled specific binding member" are used interchangeably. As such, the polymeric dye conjugate can include: (i) a water solvated polymeric dye (e.g., as described herein); and (ii) a specific binding member (e.g., as described herein). In some instances, the polymeric dye conjugate further comprises a signaling chromophore covalently linked to a multichromophore of the polymeric dye in energy-receiving proximity therewith.

Any convenient method may be used to contact the sample with a polymeric dye conjugate that specifically binds to the target analyte to produce the labelling composition contacted sample. In some instances, the sample is contacted with the polymeric dye conjugate under conditions in which the specific binding member specifically binds to the target analyte, if present. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term “a target protein” refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term “target protein” is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes lysing the cell.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labelled specific binding members find use in the subject methods, e.g., for labeling a target cell, particle, target or analyte with a polymeric dye or polymeric tandem dye. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

In some instances of the method, the labelled specific binding member includes a multichromophore as described herein (e.g., according to any one of formulae (I)-(IX)). In certain cases, $G^1$ and $G^2$ are each independently selected from the group consisting of a terminal group, a polymeric segment, a linker, a chemoselective tag and a linked specific binding member, wherein at least one of $G^1$ and $G^2$ is a linked specific binding member.

Aspects of the method include assaying the labelling composition contacted sample for the presence of a polymeric dye conjugate-target analyte binding complex to evaluate whether the target analyte is present in the sample. Once the sample has been contacted with the polymeric dye conjugate, any convenient methods may be utilized in assaying the labelling composition contacted sample that is produced for the presence of a polymeric dye conjugate-target analyte binding complex. The polymeric dye conjugate-target analyte binding complex is the binding complex that is produced upon specific binding of the specific binding member of the conjugate to the target analyte, if present. Assaying the labelling composition contacted sample can include detecting a fluorescent signal from the binding complex, if present. In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a polymeric dye conjugate-target analyte binding complex may provide assay results (e.g., qualitative or quantitative assay data) which can be used to evaluate whether the target analyte is present in the sample.

Any convenient supports may be utilized in the subject methods to immobilize any convenient component of the methods, e.g., labelled specific binding member, target, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting the labelled target. Detecting the labelled target may include exciting the multichromophore with one or more lasers and subsequently detecting fluorescence emission from the polymeric tandem dye using one or more optical detectors. Detection of the labelled target can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescently labelled targets in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the labelling composition contacted sample using fluorescence microscopy. Fluorescence microscopy imaging can be used to identify a polymeric dye conjugate-target analyte binding complex in the contacted sample to evaluate whether the target analyte is present. Microscopy methods of interest that find use in the subject methods include laser scanning confocal microscopy.

Also provided are methods of labelling a target molecule. The subject polymeric dyes, find use in a variety of methods of labelling, separation, detection and/or analysis. In some embodiments, the method includes: contacting the target molecule with a polymeric dye (e.g., as described herein) to produce a labelled target molecule, wherein the polymeric dye includes a conjugation tag that covalently links to the target molecule. In some cases, the polymeric dye further includes a signaling chromophore covalently linked to the multichromophore of the polymeric dye in energy-receiving proximity therewith. In some instances of the method, the polymeric dye member includes a multichromophore according to any one of formulae (I)-(IX) (e.g., as described herein), where one of $G^1$ and $G^2$ is a terminal group and the other of $G^1$ and $G^2$ is the conjugation tag.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagent may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa. In certain instances, the conjugation tag includes an alkyne (e.g., a cyclooctyne group) functional group and the target molecule includes an azide functional group, or vice versa, which can be conjugated via Click chemistry.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from the group consisting of a Fab fragment, a $F(ab')_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like.

In some instances, the method further includes detecting and/or analyzing the labelled target molecule. In some instances, the method further includes fluorescently detecting the labelled target molecule. Any convenient methods may be utilized to detect and/or analyze the labelled target molecule in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the polymeric dye or polymeric tandem dye, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Methods of Preparation

Aspects of the present disclosure include methods of preparing the subject multichromophores and polymeric tandem dyes. One advantage of the subject multichromophores is the modularity of the underlying scaffold. In some instances, the modular scaffold is a linear polymer having a defined sequence of repeat units. The pendant chromophores used can be chosen from a wide range of dyes which can be covalently attached to the polymeric backbone, either pre- or post-synthesis of the polymer.

In some embodiments, polymeric backbones of the subject multichromophores (see e.g., formula (IX) as described herein) can be prepared using cyclic carbonate or protected carbonate monomers. Methods and co-monomers of interest include, but are not limited to, those described by Barnes et al. in WO2013036532, Cooley et al. (J. Am. Chem. Soc., 131, 45, 1640-3, 2009), and Rothbard et al. in U.S. Pat. No. 7,169,814. Such monomers can be utilized in a polymerization reaction using an initiator and a suitable feed ratio of cyclic carbonate monomers to provide a polymeric backbone. Alternative, protected carbonate monomers can be assembled in a step wise synthesis to provide a defined sequence.

Co-monomers of interest can be linked using compatible chemoselective functional groups and chemistries. In some instances, co-monomers are linked via Click chemistry, such as copper catalyzed azide-alkyne cycloaddition, strain-promoted azide-alkyne cycloaddition, alkene azide [3+2] cycloaddition, alkene and tetrazine inverse demand Diers-Alder, Staudinger ligation and the like (see e.g., Kolb et al., Angew Chem Int Ed Engl. 40:2004-2021, 2001). As such, linking of co-monomer can be achieved via conjugations of pairs of compatible chemoselective functional groups such as, alkyne/azide, tetrazine/alkene, azide/alkene, phosphine/azide, and the like. Non-limiting examples of azide-alkyne cycloaddition reactions include copper-catalyzed azide-alkyne cycloaddition (CuAAC) reactions and ruthenium-catalyzed azide-alkyne cycloaddition (RuAAC) reactions. CuAAC works over a broad temperature range, is insensitive to aqueous conditions and a pH range over 4 to 12, and tolerates a broad range of functional groups (see Himo et al, J Am Chem Soc. 127:210-216, 2005). The active Cu(I) catalyst can be generated, for example, from Cu(I) salts or Cu(II) salts using sodium ascorbate as the reducing agent. This reaction forms 1,4-substituted products. RuAAC utilizes pentamethylcyclopentadienyl ruthenium chloride [Cp*RuCl] complexes that are able to catalyze the cycloaddition of azides to terminal alkynes, regioselectively leading to 1,5-disubstituted 1,2,3-triazoles (see Rasmussen et al., Org. Lett. 9:5337-5339, 2007). Further, and in contrast to CuAAC, RuAAC can also be used with internal alkynes to provide fully substituted 1,2,3-triazoles.

In some embodiments, polymeric backbones of the subject multichromophores are polypeptides. Any convenient peptide synthesis methods can be utilized in the preparation of such polymeric backbones of the subject multichromophores. In some cases, solid phase peptide synthesis (SPPS) methods are utilized to prepare polymeric backbones of the subject multichromophores via a defined stepwise synthesis. Conventional protecting group strategies provide for deprotection and coupling of amino acid residues of interest in a defined sequence, while sidechain functional groups of interest can be orthogonally protected. In some cases, a Fmoc/tert-butyl methodology is utilized. In some cases, a Boc/benzyl methodology is utilized. Such protecting group strategies can also be adapted for use in the installation of pendant groups of interest on the sidechains of particular amino acid residues, and/or at the polypeptide terminals. In certain instances, one or more of the pendant groups can be installed into the protected amino acid monomer starting materials. In some cases, the pendant groups are installed into the multichromophore after SPPS of the polymeric backbone has been performed. By use of orthogonal protecting groups, different groups of interest can be independently installed onto the polypeptide backbone, e.g., at the N- and C-terminals, and/or at each distinct type of amino acid residue. The polypeptide can include β2-amino acid residues, β3-amino acid residues, α-amino acid residues, or mixtures thereof.

In some embodiments, the method of preparing a light harvesting multichromophore (e.g., as described herein) includes synthesizing a protected polypeptide having a defined amino acid sequence consisting of blocks of first amino acid residues separated by single occurrences of second amino acid residues. As described herein, the preparation of a defined sequence of amino acid residues can provide for a desired configuration of pendant donor chromophores and acceptor fluorophores along the polypeptide. When installation of the pendant groups is achieved post polypeptide synthesis, chemoselective functional groups of the amino acid sidechains along the polypeptide backbone are selectively conjugated to pendant groups. In certain instances, the light harvesting multichromophore is a polypeptide having a defined sequence wherein: each block of first amino acid residues comprises at least two residues; the first amino acid residues each comprise a protected first chemoselective sidechain group; and the second amino acid residues each comprise a protected second chemoselective sidechain group.

Alternatively, installation of the pendant donor chromophore groups can be achieved by utilizing protected amino acid building blocks that already include the chromophore group as part of the sidechain. It is understood that the pendant chromophore groups can be installed first on at least the sidechains of a defined polypeptide sequence to produce a light harvesting multichromophore. A variety of additional pendant groups including acceptor fluorophores can then be installed sequentially via selective conjugation(s) to chemoselective tag(s) attached to particular residues of the sequence.

In some cases, the method further includes coupling reactive acceptor fluorophore moieties to deprotected second chemoselective sidechain groups of the second amino acid residues to produce pendant acceptor fluorophores.

In certain instances of the method, the defined amino acid sequence comprises one or more amino acid sequence segments selected from the following:

XYXX

XXYXX

XXXYXXX

XXXYXXXX

XXXXYXXX

XXXXYXXXX

XXXXXYXXXXX

XXXXXXYXXXXXX

-continued

XXXXXXXYXXXXXXX

XXXXXXXXYXXXXXXXX

XXXXXXXXXYXXXXXXXXX $Y(X)_nY$ $XY(X)_nYX$ $XXY(X)_nYXX$ $XXXY(X)_nYXXX$ $XXXXY(X)_nYXXXX$ $XXXXXY(X)_nYXXXXX$ wherein each X is a first amino acid residue having a first chemoselective functional group, or protected version thereof, and each Y is a second amino acid residue having a second chemoselective functional group, or protected version thereof.

In certain embodiments of the sequences above, each X is a lysine or ornithine residue, or a protected version thereof, having a sidechain amino group that can be selectively covalently N-linked to a pendant donor chromophore group; and each Y is a cysteine residue or a protected cysteine residue having a sidechain thiol group that can be selectively covalently linked to a pendant acceptor fluorophore.

Polypeptide sequences comprising two or more of the sequence segments described above can be prepared, optionally separated by additional third amino acid residues (e.g., (segment 1)-Z-(segment 2) where Z is the third residue). This third amino acid residue can be a spacer residue (e.g., not having a sidechain or a tag), or a residue having a chemoselective functional group suitable for selective installation of an additional moiety of interest, such as a second pendant light absorbing chromophore, a chemoselective tag (e.g., a bio-orthogonal click chemistry tag), a linker, a linked biomolecule, a acceptor fluorophore, a WSG, etc. In certain instances the additional moiety of interest is incorporated into the third amino acid residue prior to polypeptide synthesis.

Similarly, a variety of moieties can be installed at the N- and/or C-terminal of the polypeptide during or after peptide synthesis. In certain instances, the method further includes deprotecting the N-terminal of the protected polypeptide and coupling a G1 group (e.g., as described herein) to the N-terminal of the N-terminal deprotected polypeptide. G1 can be any convenient terminal group (e.g., a capping group such as an alkanoyl, e.g., acetyl), a donor chromophore group, a linker having a particular chemoselective tag or a biomolecule of interest.

In some cases, the method further includes installing a G2 group at the C-terminal of the polypeptide. This can be achieved in a variety of ways: e.g., during SPPS where the C-terminal group G2 is installed between the solid support and the first amino acid residue of the sequence; during cleavage of the polypeptide from the solid support; or post synthesis where a moiety of interest (e.g., a specific binding member) or a particular chemoselective tag directed to same, can be coupled to the C-terminal of the polypeptide. In some instances, native chemical ligation methods can be utilized to prepare a C-terminal thioester polypeptide suitable for coupling to a polypeptide fragment or a moiety of interest.

Any of the polypeptide multichromophores described herein can be prepared according to the subject methods, e.g., polypeptides of formulae (IV)-(VII), and synthetic precursors thereof, as described herein.

A summary of some of the various methods available for synthesizing the subject polypeptide multichromphores can be found in Steward et al., in "Solid Phase Peptide Synthesis", W.H. Freeman Co., San Francisco, 1969; Bodanszky et al., in "Peptide Synthesis", John Wiley & Sons, Second Edition, 1976 and Meienhofer, in "Hormonal Proteins and Peptides", Vol. 2, p. 46, Academic Press (New York), 1983; and Kent, Ann. Rev. Biochem., 57, 957, 1988, for solid phase peptide synthesis, and Schroder et al., in "The Peptides", Vol. 1, Academic Press (New York), 1965 for solution synthesis. Any convenient protecting group strategies may be used such as, but are not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based or other convenient protecting groups may be used for the protection of sidechain functional groups. In Fmoc solid-phase peptide synthesis a Fmoc-amino protecting group is used at the amino terminal and tert-butyl or benzyl-based or other convenient protecting groups may be used for protection of sidechain functional groups. Convenient protecting groups that may be used in such synthetic methods are described in the above references and by McOmic in "Protective Groups in Organic Chemistry", Plenum Press, New York, 1973; and Greene and Wuts, "Protective Groups in Organic Synthesis", John Wiley & Sons, 4th Edition, 2006.

Systems

Aspects of the invention further include systems for use in practicing the subject methods and compositions. A sample analysis system can include sample field of view or a flow channel loaded with a sample and a labelled specific binding member. In some embodiments, the system is a flow cytometric system including: a flow cytometer including a flow path; a composition in the flow path, wherein the composition includes: a sample; and a labelled specific binding member (e.g., as described herein). In some embodiments, the system for analyzing a sample is a fluorescence microscopy system, including: a fluorescence microscope comprising a sample field of view; and a composition disposed in the sample field of view, wherein the composition comprises a sample; and a labelled specific binding member (e.g., as described herein).

In some instances of the systems, the labelled specific binding member includes: a water solvated light harvesting multichromophore (e.g., as described herein) and a specific binding member that specifically binds a target analyte covalently linked to the multichromophore. In some cases, the labelled specific binding member further comprises a signaling chromophore covalently linked to the multichromophore of the polymeric dye in energy-receiving proximity therewith. In some instances of the subject systems, the labelled specific binding member, the multichromophore is described by any one of formulae (I)-(IX) (e.g., as described herein), wherein: $G^1$ and $G^2$ are each independently selected from the group consisting of a terminal group, a polymeric conjugated segment, a linker and a linked specific binding member, wherein at least one of $G^1$ and $G^2$ is a linked specific binding member.

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from the group consisting of a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Suitable flow cytometer systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry,* 3rd ed., Wiley-Liss (1995); Virgo, et al. (2012) *Ann Clin Biochem*. January; 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, BD Biosciences Accuri™ systems, BD Biosciences FACSCanto™ systems, BD Biosciences FACSCelesta™ systems, BD Biosciences FACSLyric™ systems, BD Biosciences FACSVerse™ systems, BD Biosciences FACSymphony™ systems, BD Biosciences LSRFortessa™ systems, BD Biosciences Influx™ cell sorter, BD Biosciences FACSJazz™ cell sorter and BD Biosciences FACSAria™ cell sorter, BD Biosciences FACSMelody™ cell sorter, and the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit can include a polymeric dye including a water solvated light harvesting multichromophore (e.g., as described herein) and a container. Any convenient containers can be utilized, such as tubes, bottles, or wells in a multi-well strip or plate, a box, a bag, an insulated container, and the like. The subject kits can further include one or more components selected from a polymeric tandem dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from the group consisting of a Fab fragment, a F(ab')2 fragment, a scFv, a diabody and a triabody.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The polymeric dyes, compositions, methods and systems as described herein may find use in a variety of applications, including diagnostic and research applications, in which the labelling, detection and/or analysis of a target of interest is desirable. Such applications include methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

EXAMPLES

Example 1

The synthesis of the subject polymeric dyes can be achieved by a Suzuki coupling method. Other methods such as a C—H bond arylation or a Stille coupling method can also be utilized to construct and polymerize a repeat unit including an aryl or heteroaryl co-monomer with a saturated PEG co-monomer.

The formula of a tandem dye based on multichromophore A (MC) is depicted in FIG. 1. A series of tandem dyes having the following core structure with different acceptor fluorophores ("Dye") was prepared:

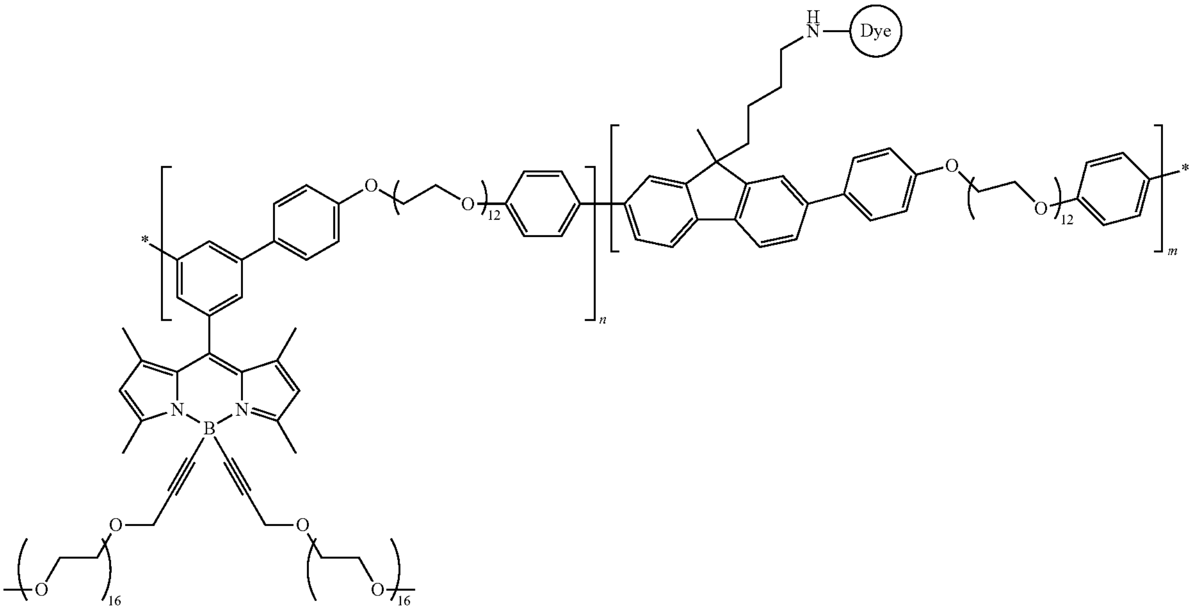

Figure 2:
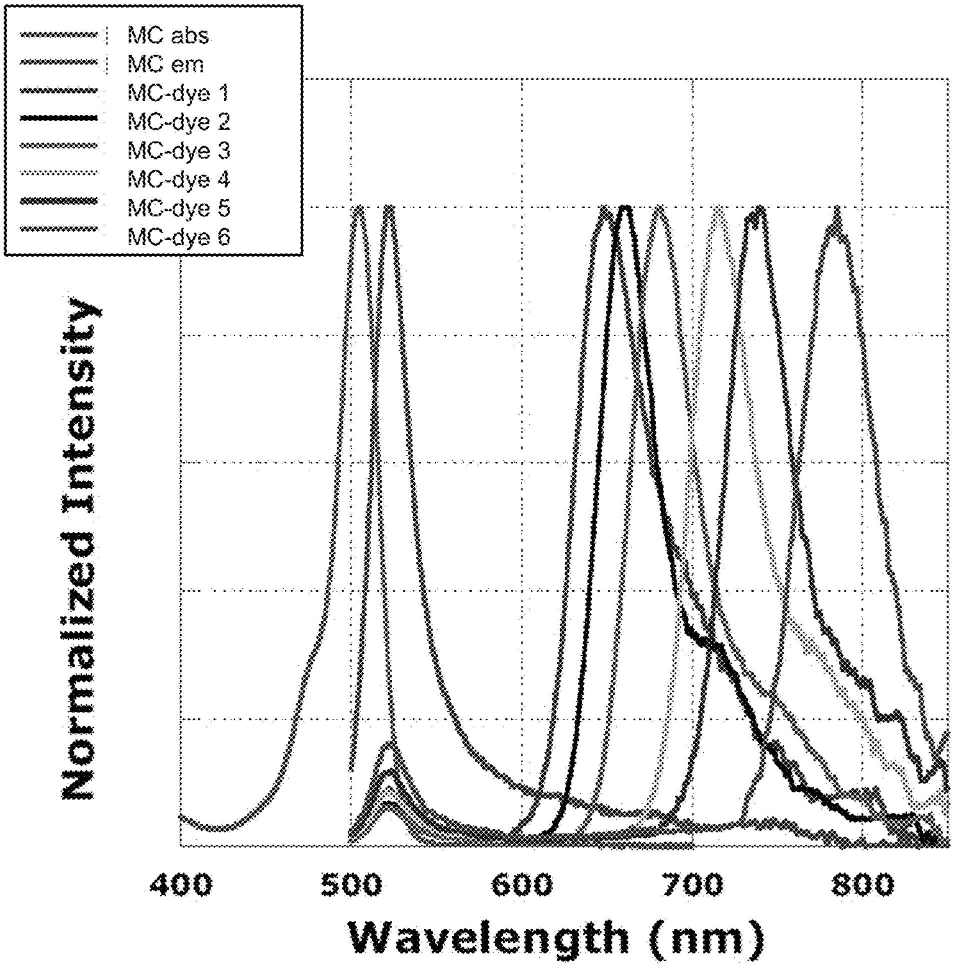
FIG. 2 shows a normalized absorption spectrum for an exemplary multichromophore and emission spectra for a series of polymeric tandem dyes including the multichromophore.
Figure 3:
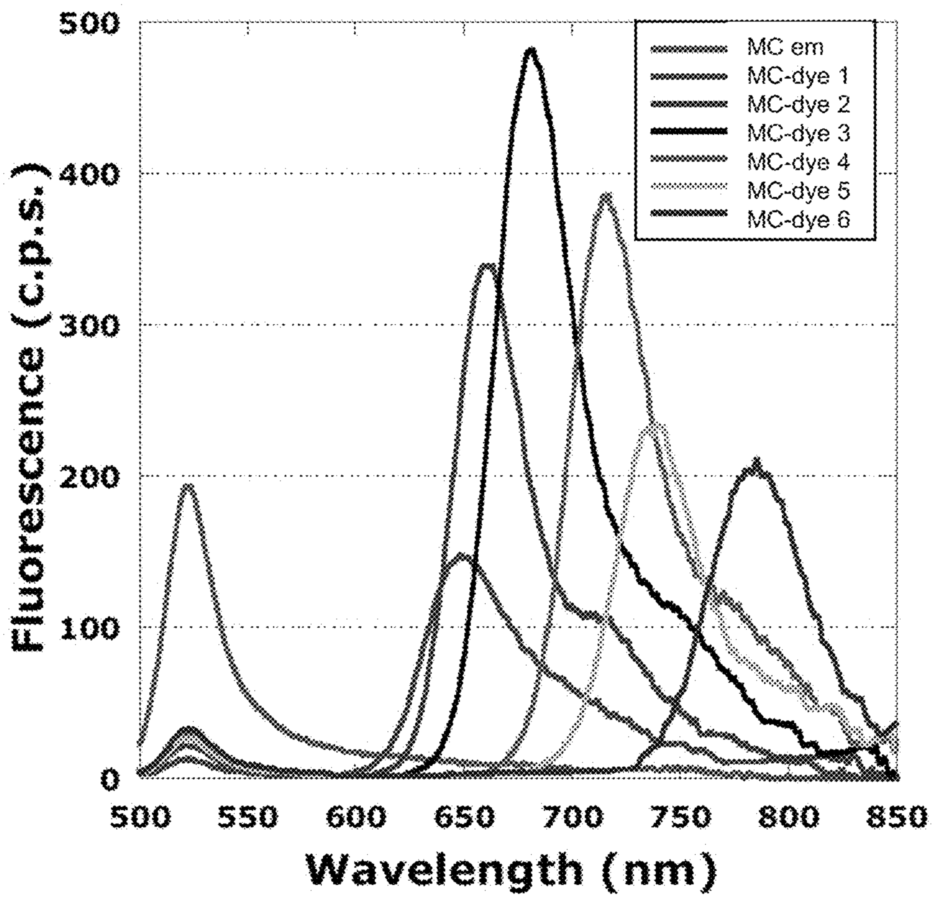
FIG. 3 shows emission spectra for an exemplary multichromophore and a series of polymeric tandem dyes including the multichromophore, all at 0.04 OD absorption.

The spectroscopic properties of the exemplary polymeric tandem dyes was evaluated, as shown in FIG. 2 and FIG. 3.

TABLE 1

Spectroscopic data for a pendant multichromophore and corresponding tandem dyes

| Emitter | $\lambda max_{(em)}$ (nm) | D/A | Quantum Yield (%) | Amplification factor |
|---|---|---|---|---|
| MC | 523 | N/A | 9 | N/A |
| MC-dye 1 | 649 | 0.09 | 12 | 5.1 |
| MC-dye 2 | 661 | 0.06 | 23 | 2.1 |
| MC-dye 3 | 682 | 0.06 | 33 | 1.8 |
| MC-dye 4 | 717 | 0.08 | 27 | 2.2 |
| MC-dye 5 | 740 | 0.12 | 16 | 2.3 |
| MC-dye 6 | 786 | 0.16 | 14 | 2.1 |

Example 2

Figure 4:
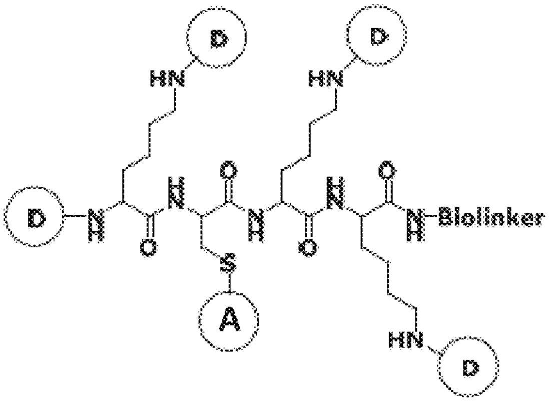
FIG. 4 depicts the structure of an exemplary polymeric tandem dye having a peptidic backbone. D is a BODIPY donor pendant group, A is an acceptor dye and biolinker is a linker including a chemoselective functional group for attachment of the tandem dye to a biomolecule.
Figure 4:
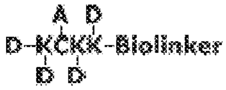

Solid phase peptide synthesis methods were used to prepare a sequence of lysine and cysteine amino acid residues KCKK, as shown in FIG. 4. Carboxylic acid-substituted BODIPY groups were conjugated to the N-terminal and to the sidechain amino groups of the lysine residues of the peptide via amide bond coupling. A maleimide-substituted acceptor fluorophore (Dye 7) was conjugated to the cysteine residue utilizing maleimide-thiol coupling chemistry. The peptide was prepared with a C-terminal linker suitable for conjugation to a biomolecule, e.g., protein.

Figure 5A:
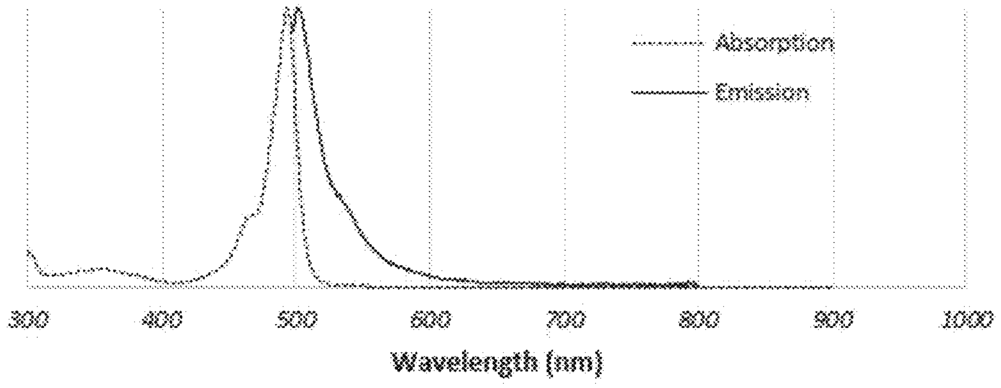
FIG. 5A shows absorption and emission spectra for the BODIPY donor pendant group that was used to prepare the multichromophore of FIG. 4.
Figure 5B:
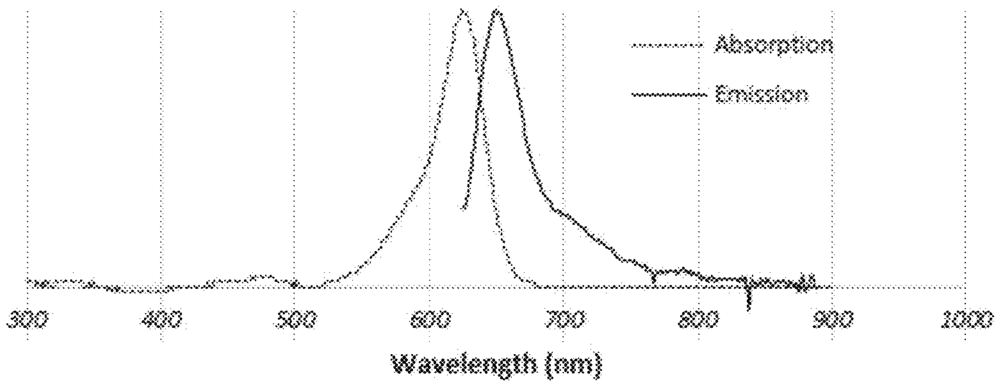
FIG. 5B shows absorption and emission spectra for the acceptor dye used to prepare the multichromophore of FIG. 4.
Figure 5C:
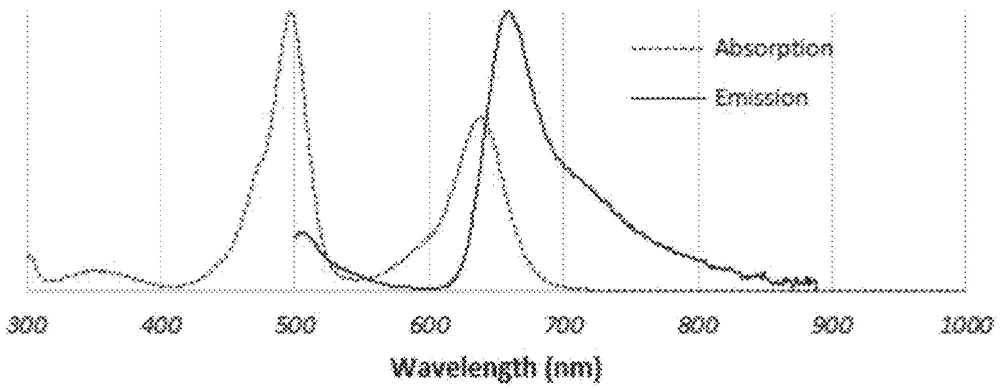
FIG. 5C shows absorption and emission spectra for the exemplary polymeric tandem dye of FIG. 4.

The spectroscopic properties of the BODIPY-based tandem dye of FIG. 4 were characterized. FIG. 5A shows absorption and emission spectra for the BODIPY donor pendant group. FIG. 5B shows absorption and emission spectra for the acceptor dye (Dye 7). FIG. 5C shows absorption and emission spectra for the exemplary polymeric tandem dye of FIG. 4. For the emission spectrum of the scaffolded chromophore, the primary chromophore is being excited. For this system, the emission of the donor is nearly completely quenched and most of the emission is that of the acceptor fluorophore. The quantum yield of the polymeric tandem dye is comparable to the acceptor fluorophore (Dye 7), suggesting the tandem dye exhibits an efficient energy transfer process. The fluorescence of this exemplary tandem dye was amplified by approximately 2-fold over that of the acceptor fluorophore alone (Dye 7).

Polypeptides providing a ratio of donor to acceptor of 5:1. 6:1, 7:1, 8:1, 9:1, 10:1 and 20:2 are prepared and characterized using the methods described above.

Example 3

Figure 9A:
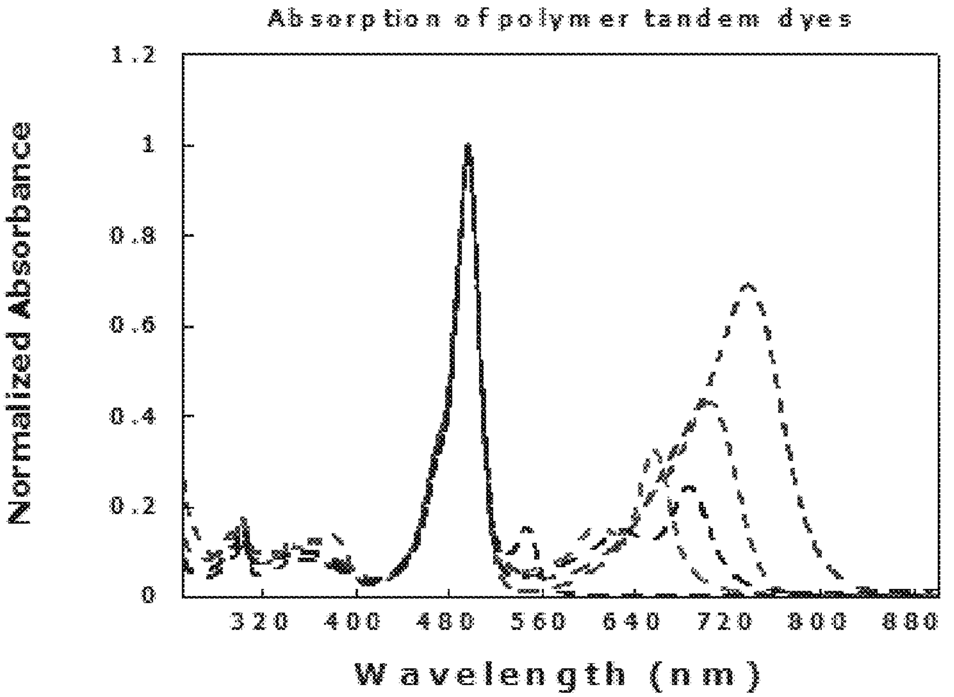
FIG. 9A-9B show the absorption (FIG. 9A) and emission spectra (FIG. 9B) of a series of exemplary polymeric tandem dyes including linked pendant BODIPY donor dyes and a variety of acceptor dyes having different emission maximum wavelengths.
Figure 9B:
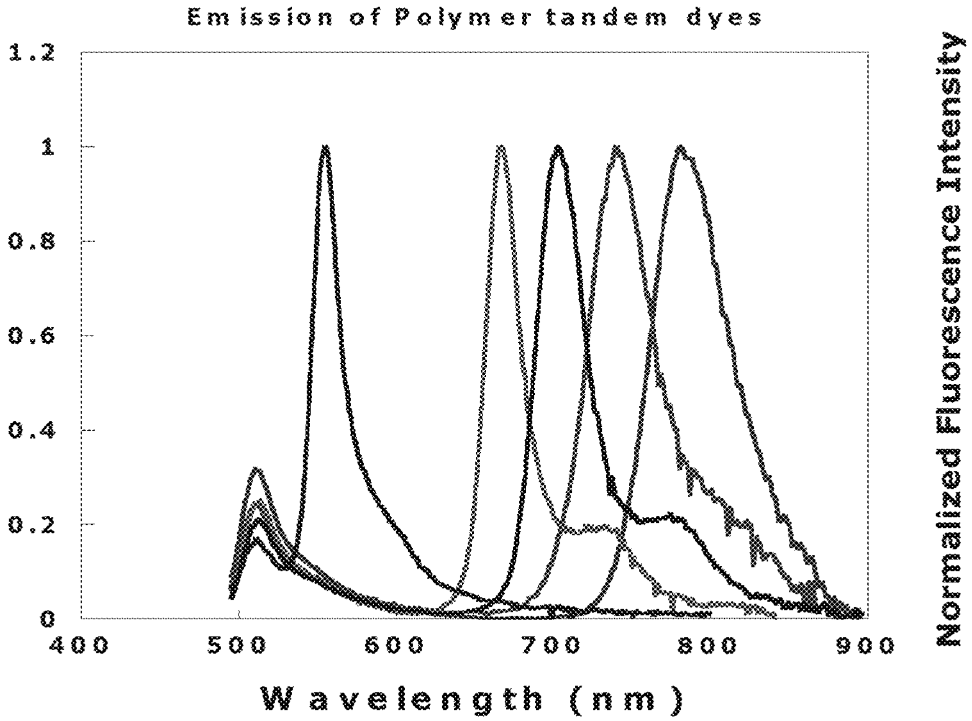

Water-soluble fluorescent polymer dyes can be prepared by click polymerization under mild conditions. These polymers dyes can be covalently bonded to a bio-recognition unit (biomolecule) and serve as fluorescent probes for a target. When secondary dyes are incorporated as acceptors, polymeric tandem dyes are formed. By tuning color of the acceptor dyes, polymeric tandem dyes having the same excitation wavelength (see FIG. 9A) but a range of different alternative emission wavelengths can be prepared (see FIG. 9B).

PEGylated BODIPY dyes with desired narrow absorption are selected as fluorophore pendant dyes. The pendant fluorophore is chemically bounded to water soluble ethylene glycol ether monomers terminated with diazide, dialkyne, or azide/alkyne. The PEG polymer chain with attached BODIPY dyes can be prepared using Cu(I) catalyzed 1,3-dipolar cycloadditions of alkyne to azide in good MW (e.g., as described herein). When only one type of fluorophore dye is attached as a pendant group, the resulted polymer exhibits fluorescence as a simple fluorescent polymer dye (see FIG. 8). When a second acceptor fluorophore is attached, a polymer chain with two fluorophore pedants is achieved. One fluorophore at higher energy level can serve as an energy donor and the 2nd fluorophore at the low energy level as energy acceptor. By mixing the suitable pair and ratio of donor/acceptor, the polymeric tandem dyes with desired emission wavelength can be obtained.

The following polymeric dyes are prepared by click polymerization methods, using co-monomers and methods as described by the synthetic schemes of FIGS. 7A and 7B, where it is understood that n and m together can represent the average length of the polymer and the relative ratios of co-monomers, and that n and m can be selected as desired by controlling the parameters of the polymerization reaction using any convenient methods. It is understood that the depending on the method of polymerization, the n and m repeating units may be present in a random configuration or in a block configuration. In addition, the following polymeric structures can be further conjugated to any convenient molecule of interest, e.g., a biomolecule, using Click chemistry via a terminal azide or alkyne group. In some cases, n and m are each independently selected from 1 to 1000, such as 1 to 500, 1 to 200, 1 to 100, 2 to 100 or 5 to 100.

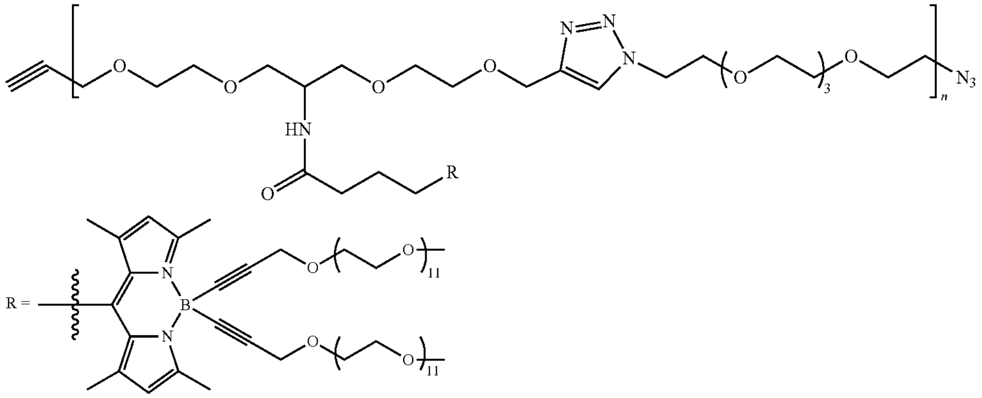

Figure 8:
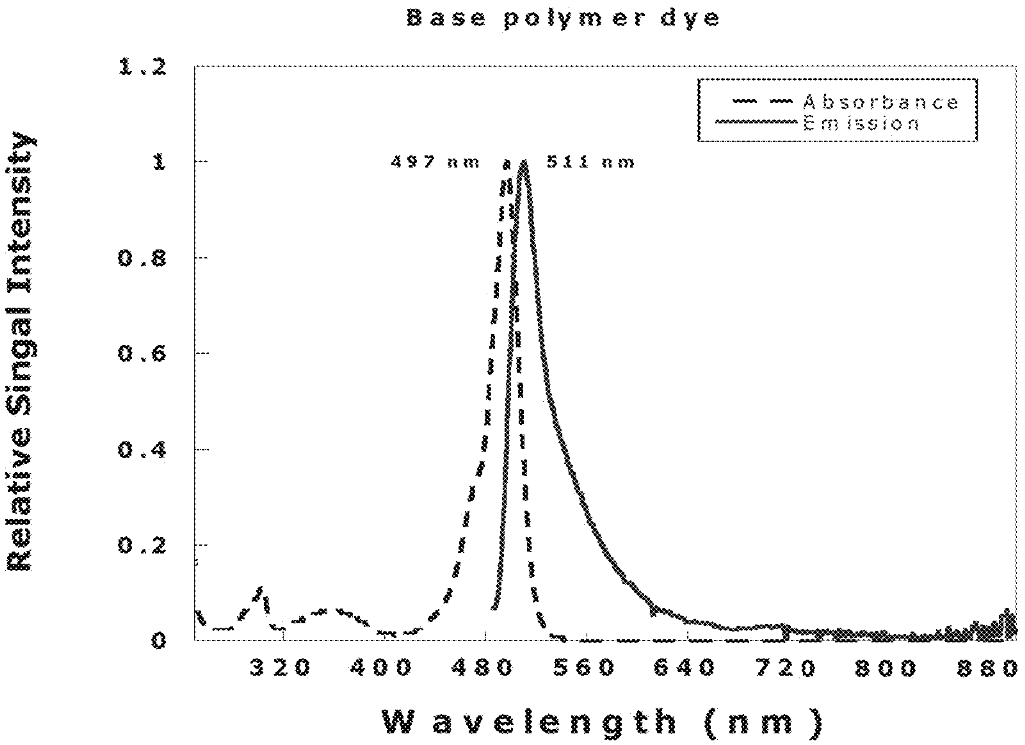
FIG. 8 show the absorption and emission spectra of an exemplary multichromophore of FIG. 7A that includes linked pendant BODIPY dyes.

FIG. 8 shows the absorption and emission spectra of a base polymer dye including a pendant BODIPY dye of the general structure shown above. Other exemplary polymeric dyes where R is a linked donor dye (e.g., a BODIPY dye as described above), and including a sidechain —$NH_2$ group suitable for conjugation (e.g., via an amide bond and linker to an acceptor dye) are:

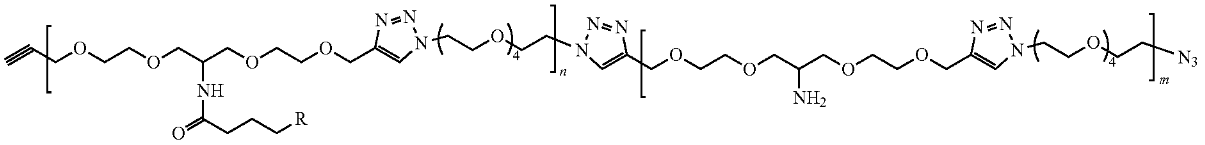

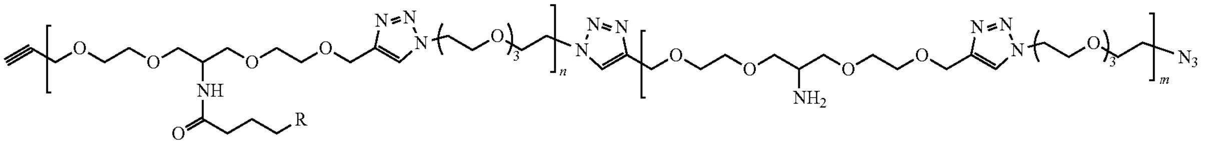

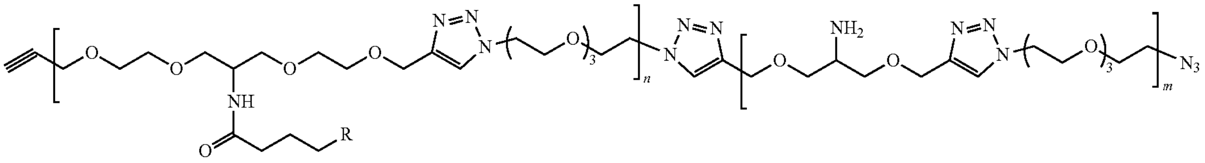

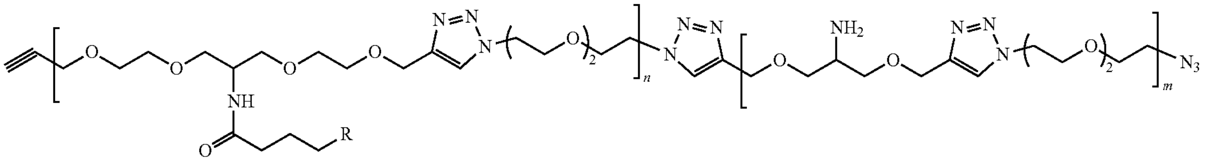

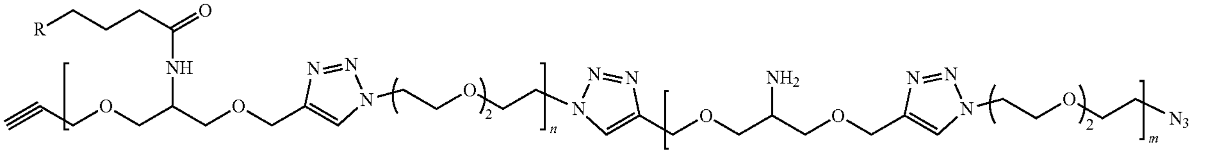

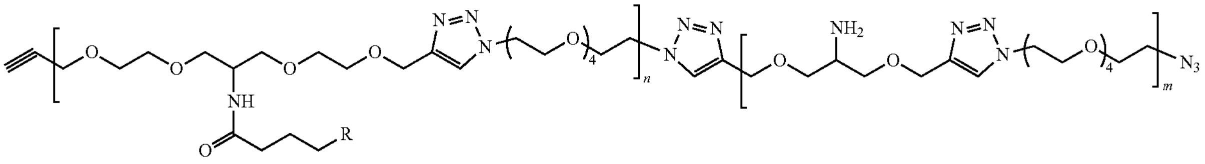

Exemplary polymeric tandem dye structures are shown below where R is a linked donor dye (e.g., a BODIPY dye as described above), and including a linked acceptor dye of interest (e.g., suitable for conjugation (e.g., to an acceptor dye) such as DY-754 or DY-704, where DY refers to a Dyomics dyes having, e.g., emission maximum wavelengths of 754 nm or 704 nm, respectively. By selecting an acceptor dye of interest that overlaps at least partially with the emission spectrum of the base polymer (see FIG. 8), polymeric tandem dyes having a variety of emission wavelengths can be produced. See e.g., FIG. 9A-9B.

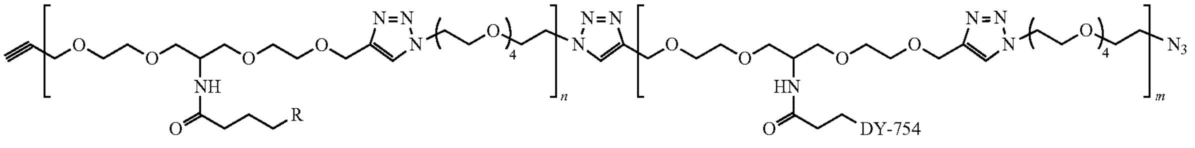

-continued

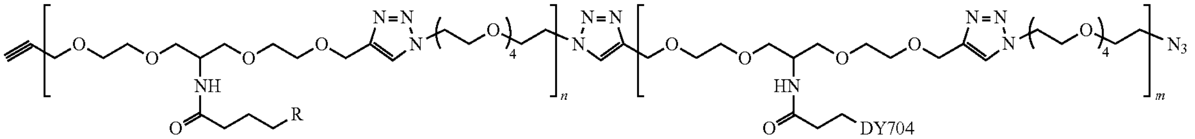

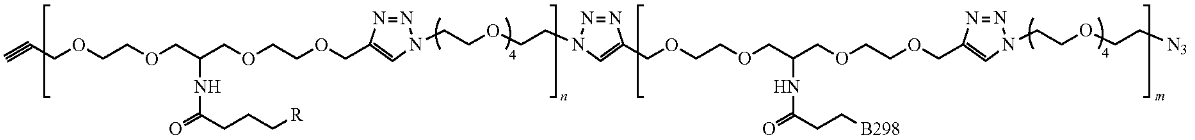

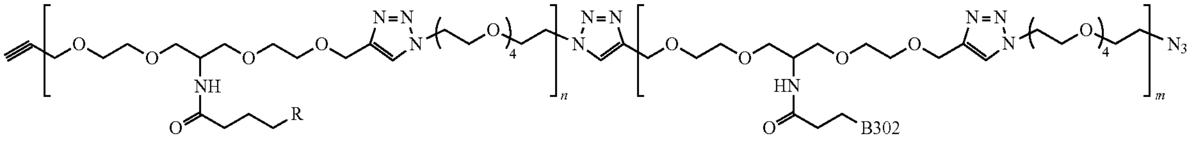

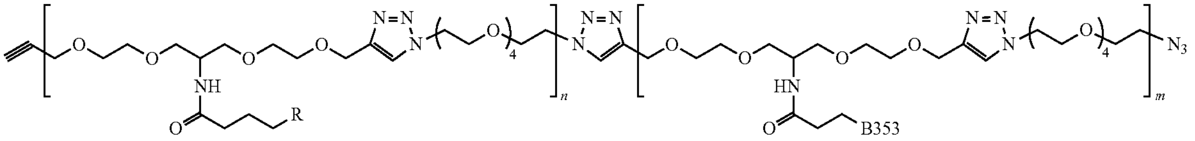

ADDITIONAL EMBODIMENTS

Notwithstanding the appended claims, the disclosure set forth herein is also defined by the following clauses:

Clause 1. A water-soluble light harvesting multichromophore comprising:

a polymeric backbone comprising non-conjugated repeat units; and a plurality of pendant donor chromophore groups each independently linked to a non-conjugated repeat unit of the polymeric backbone.

Clause 2. The multichromophore according to clause 1, wherein the pendant donor chromophore groups are each substituted with a water soluble group.

Clause 3. The multichromophore according to clause 1, wherein the polymeric backbone is a linear polymer.

Clause 4. The multichromophore according to clause 1, wherein the pendant donor chromophore groups are configured in energy-transferring proximity to each other.

Clause 5. The multichromophore according to clause 4, wherein the configuration of pendant donor chromophore groups exhibits, upon excitation with incident light, quenching of fluorescence relative to an unquenched isolated donor chromophore group.

Clause 6. The multichromophore according to any one of clauses 1-5, wherein the pendant donor chromophore groups are selected from a fused tricyclic aryl or heteroaryl group and a BODIPY group.

Clause 7. The multichromophore according to clause 6, wherein the pendant donor chromophore groups are selected from fluorene, carbazole and silole.

Clause 8. The multichromophore according to any one of clauses 6-7, wherein the pendant donor chromophore groups are a fused tricyclic aryl or heteroaryl group having one of the following formulae:

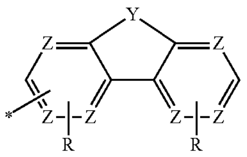

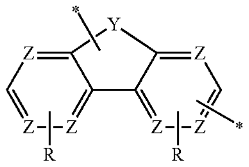

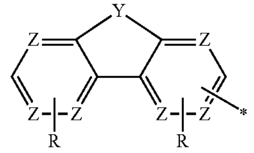

wherein:

* is a point of linkage to a non-conjugated repeat unit of the polymeric backbone;

Y is $C(R^{13})_2$, $—C(R^{13})_2C(R^{13})_2—$, $—C(R^{13})_2Si(R^{13})_2—$, $NR^{13}$, $Si(R^{13})_2$ or Se;

each Z is independently CH, CR or N;

each $R^{13}$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, a WSG and $-L^{11}-Z^1$, wherein $L^{11}$ is a linker and $Z^1$ is a non-conjugated repeat unit, or wherein any two convenient R' groups are optionally cyclically linked; and each R is independently H or one or more substituents and wherein any two convenient R groups are optionally cyclically linked;

wherein one of R and $R^{13}$ is linked to a non-conjugated repeat unit of the polymeric backbone.

Clause 9. The multichromophore according to any one of clauses 1-6, wherein the pendant donor chromophore groups are BODIPY groups.

Clause 10. The multichromophore according to clause 9, wherein the BODIPY groups are described by the formula:

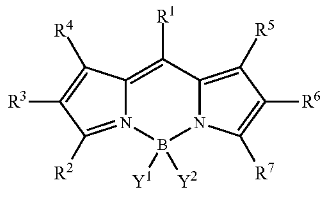

wherein:

$R^1$-$R^7$ are each independently selected from H, alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and -$L^1$-$Z^1$, or optionally any one or more pairs of substituents selected from $R^6$ and $R^7$, $R^2$ and $R^3$, $R^5$ and $R^6$, $R^3$ and $R^4$, $R^4$ and $R^1$ and $R^5$ and $R^1$, together form a divalent radical and are cyclically linked and together with the carbon atoms to which they are bound provide a 5- or 6-membered fused heterocycle, carbocycle, aryl or heteroaryl ring (e.g., a 5- or 6-membered ring comprising carbon atoms and 0-3 heteroatoms selected from O, S and N), which ring may be unsubstituted or further substituted with a substituent independently selected from alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and -$L^1$-$Z^1$;

$L^1$ is a linker;

$Z^1$ is a non-conjugated repeat unit of the polymeric backbone; and $Y^1$ and $Y^2$ are independently selected from F, OH, H, cyano, alkyl, substituted alkyl, aryl, substituted aryl, heteroaryl, substituted heteroaryl, alkoxy, substituted alkoxy, alkenyl, substituted alkenyl, alkynyl, substituted alkynyl and WSG;

wherein one of $Y^1$, $Y^2$ and $R^1$-$R^7$ is linked to a non-conjugated repeat unit of the polymeric backbone.

Clause 11. The multichromophore according to clause 10, wherein $R^1$ is an optionally substituted aryl or heteroaryl linked to a non-conjugated repeat unit of the polymeric backbone.

Clause 12. The multichromophore according to any one of clauses 10-11, wherein $Y^1$ and $Y^2$ each comprise a water solubilizing group (WSG).

Clause 13. The multichromophore according to any one of clauses 10-12, wherein the pendant donor chromophore groups are described by the following structure:

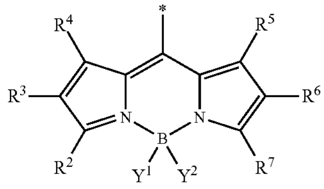

wherein:

* is a point of linkage to a non-conjugated repeat unit of the polymeric backbone;

$Y^1$ and $Y^2$ are each alkynyl substituted with a WSG.

Clause 14. The multichromophore according to clause 13, wherein the pendant donor chromophore groups are described by the following structure:

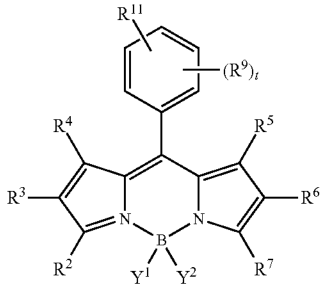

wherein:

$R^{11}$ is $L^1$-$Z^1$ (a linked non-conjugated repeat unit of the polymeric backbone);

each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4.

Clause 15. The multichromophore according to any one of clauses 1-14, wherein the pendant donor chromophore groups are substituted with one or more water solubilizing groups (WSGs) independently selected from the following formula:

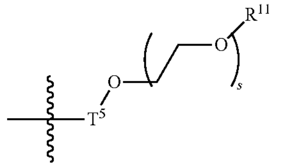

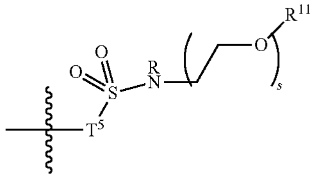

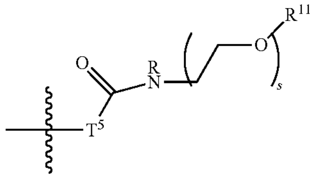

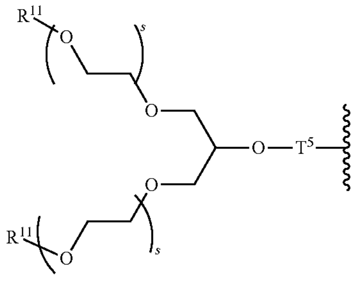

-continued
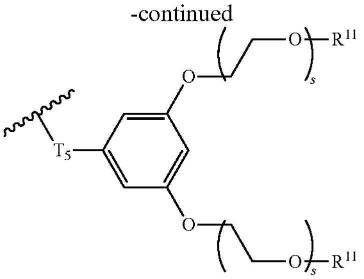
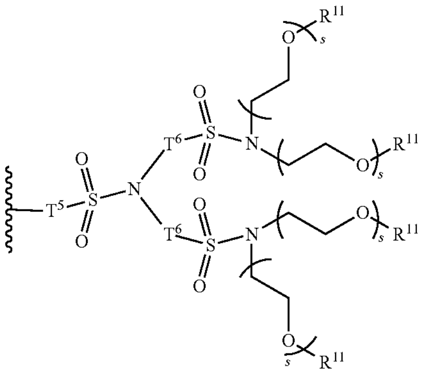
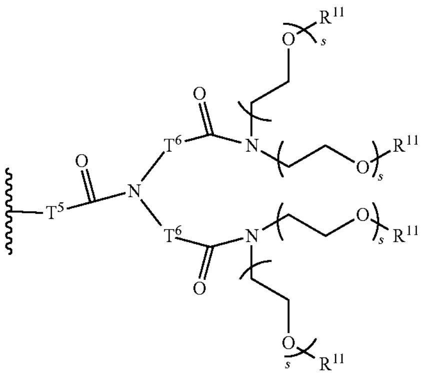
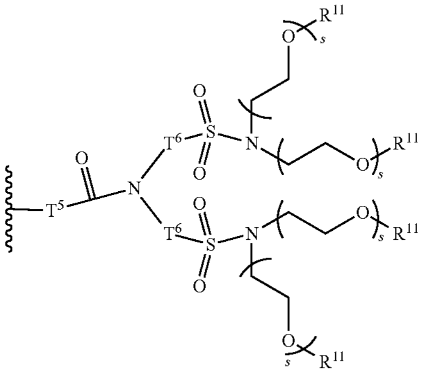
-continued
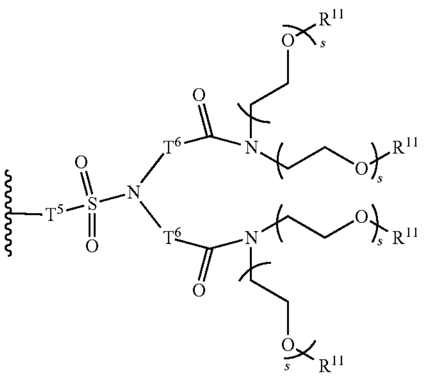
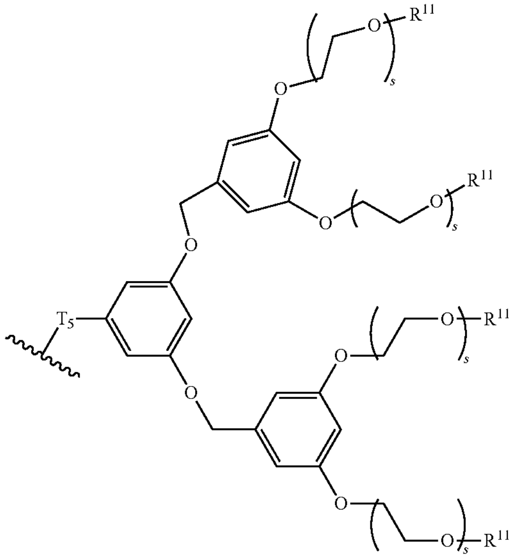
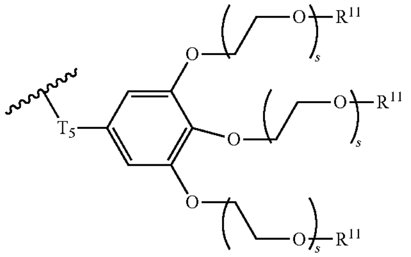
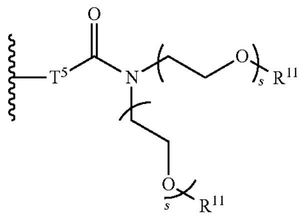
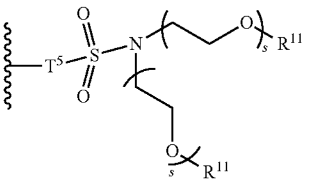

-continued

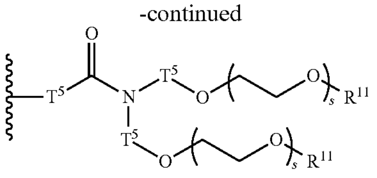

wherein:

$T^5$ is an optional linker;

each $T^6$ is an linker;

$R^{11}$ and R are independently H, alkyl or substituted alkyl; and each s is an integer from 1 to 50.

Clause 16. The multichromophore according to any one of clauses 1-15, comprising a segment of the formula:

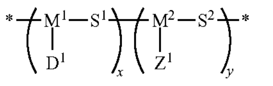

wherein:

each $M^1$ and $M^2$ is independently an aryl or heteroaryl co-monomer;

each $S^1$ and $S^2$ is independently a non-conjugated spacer unit;

each $D^1$ is independently a pendant donor chromophore linked to $M^1$;

each $Z^1$ is independently a chemoselective tag linked to $M^2$;

x is 75 mol % or more; and y is 25 mol % or less.

Clause 17. The multichromophore according to clause 16, wherein the $M^1$-$S^1$ and $M^2$-$S^2$ repeat units of the polymeric backbone have a random configuration.

Clause 18. The multichromophore according to any one of clauses 16-17, wherein:

each $M^1$ and $M^2$ independently comprises one or more groups selected from fluorene, carbazole, silole, biphenylene and phenylene; and each $S^1$ and $S^2$ is independently a saturated spacer unit selected from a divalent polyethylene glycol (PEG) and a divalent modified PEG group.

Clause 19. The multichromophore according to any one of clauses 1-15, comprising a segment of the formula:

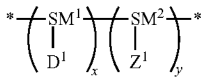

wherein:

the polymeric backbone of non-conjugated repeat units comprises $SM^1$ and $SM^2$ co-monomers that are each independently a saturated non-conjugated co-monomer;

each $D^1$ is independently a pendant donor chromophore linked to $SM^1$;

each $Z^1$ is independently a chemoselective tag linked to $SM^2$;

x is 75 mol % or more; and y is 25 mol % or less.

Clause 20. The multichromophore according to clause 19, wherein the $SM^1$ and $SM^2$ repeat units of the polymeric backbone have a random configuration.

Clause 21. The multichromophore according to any one of clauses 19-20, wherein $SM^1$ and $SM^2$ are co-monomers derived from an acrylate, a methacrylate, an acrylamide, a polystyrene, a ROMP monomer, an ADMET monomer or a cyclic carbonate.

Clause 22. The multichromophore according to clause 21, wherein $SM^1$ and $SM^2$ are selected from the following formulae:

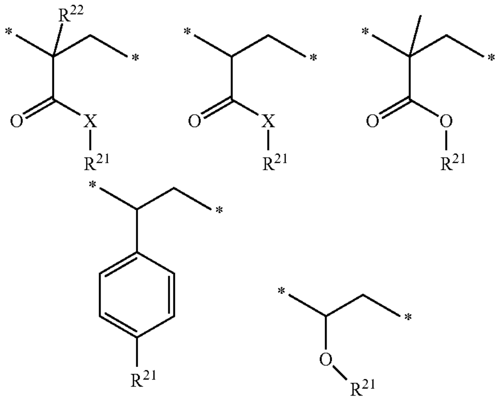

wherein:

$R^{21}$ is $-L^1-D^1$ or $-L^2-Z^1$;

$D^1$ is the pendant donor chromophore linked to $M^1$;

$Z^1$ is a chemoselective tag linked to $M^2$;

$L^1$ and $L^2$ are optional linkers;

X is O or NR";

$R^{22}$ is H or lower alkyl;

R" is H or lower alkyl, substituted lower alkyl and WSG; and

* is a connection to the polymeric backbone.

Clause 23. The multichromophore according to clause 19, wherein the multichromophore is of formula (XXI):

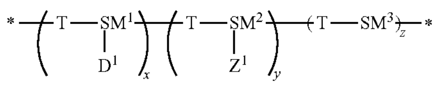

(XXI)

wherein:

the polymeric backbone of non-conjugated repeat units comprises $SM^1$, $SM^2$ and $SM^3$ co-monomers that are each linked via a group T that is the product of a click chemistry or chemoselective group conjugation reaction;

$SM^3$ optionally comprises a linked WSG;

each $D^1$ is independently a pendant light absorbing chromophore linked to $SM^1$;

each $Z^1$ is independently a chemoselective tag linked to $SM^2$;

x is 50 mol % or more; and y+z is 50 mol % or less, where * is a connection to the polymeric backbone of the multichromophore or a terminal group.

Clause 24. The multichromophore according to clause 23, wherein $SM^1$, $SM^2$ and $SM^3$ comprise the following structures:

SM[1]

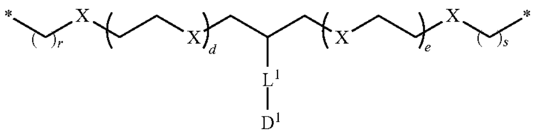

SM[2]

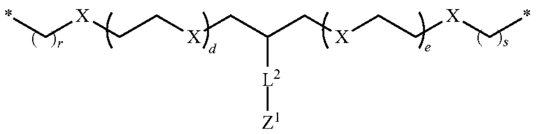

SM[3]

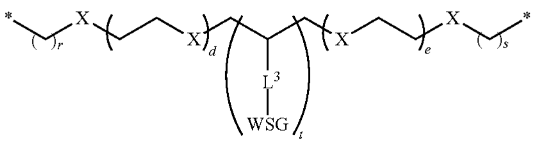

wherein:

each X is independently O or $NR^{31}$ wherein $R^{31}$ is H, alkyl, substituted alkyl, alkanoyl or substituted alkanoyl;

each r and s is independently 1-6 (e.g., 1, 2 or 3);

each d and e is independently 1-12 (e.g., 1-6, such as 1, 2, 3, 4, 5 or 6);

t is 0 or 1;

$D^1$ is a pendant donor chromophore;

$Z^1$ is a chemoselective tag (e.g., as described herein);

WSG is a water solubilizing group (e.g., as described herein);

each $L^1$, $L^2$ and $L^3$ is independently a linker; and

* is a connection to a 1,4-substituted 1,2,3-triazole (T) having one of the following structures:

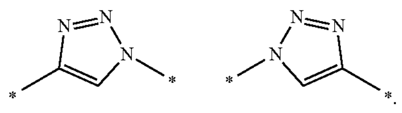

or a terminal group $G^1$ or $G^2$ (e.g., as described herein).

Clause 25. The multichromophore according to clause 19, wherein the repeat units of the polymeric backbone have a defined linear sequence.

Clause 26. The multichromophore according to clause 25, wherein $SM^1$ and $SM^2$ are co-monomers derived from amino acids, peptoid monomers, a protected carbonate monomer or a cyclic carbonate monomer.

Clause 27. The multichromophore according to any one of clauses 19, 25 and 26, wherein the polymeric backbone is a polypeptide having a defined sequence of α-amino acid residues and/or β-amino acid residues.

Clause 28. The multichromophore according to any one of clauses 19 and 25-27, wherein the multichromophore is of the formula:

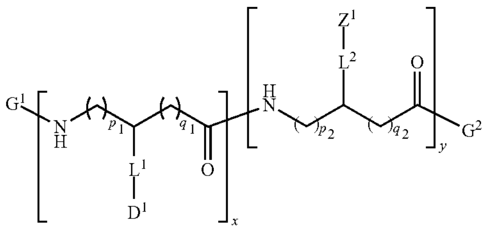

wherein:

each $D^1$ is independently a pendant donor chromophore group;

each $Z^1$ is independently a chemoselective tag;

each $L^1$ and $L^2$ are independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ and $G^2$ are each independently selected from a terminal group, a polymer segment, a donor chromophore group, an acceptor fluorophore group, a linker and a linked specific binding member.

Clause 29. The multichromophore of clause 28, wherein $p_1$ and $p_2$ are each 0 and $q_1$ and $q_2$ are each 1.

Clause 30. The multichromophore of clause 28, wherein $p_1$ and $p_2$ are each 1 and $q_1$ and $q_2$ are each 0.

Clause 31. The multichromophore of clause 28, wherein $p_1$, $p_2$, $q_1$ and $q_2$ are each 0 and the multichromophore is of the formula:

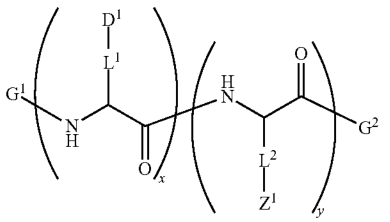

wherein:

each $D^1$ is independently a pendant donor chromophore group;

each $Z^1$ is independently a chemoselective tag;

$L^1$ and $L^2$ are each independently a linker;

x is 75 mol % or more;

y is 25 mol % or less; and $G^1$ and $G^2$ are each independently selected from a terminal group, a polymer segment, a donor chromophore group, an acceptor fluorophore group, a linker and a linked specific binding member.

Clause 32. The multichromophore according to any one of clauses 27, 28 and 31, comprising a segment of the formula:

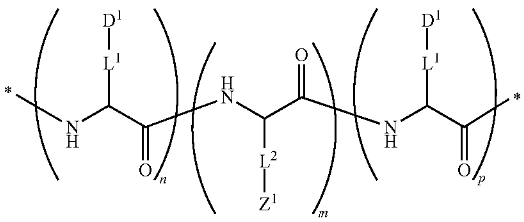

wherein:

each $D^1$ is independently a pendant donor chromophore group;

each $Z^1$ is independently a chemoselective tag;

each $L^1$ and $L^2$ are independently a linker;

n and p are each independently an integer from 1 to 20 wherein $n+p\geq 2$; and m is 1 or 2.

Clause 33. The multichromophore according to clause 32, wherein the multichromophore comprises q segments of copolymer and is of the formula:

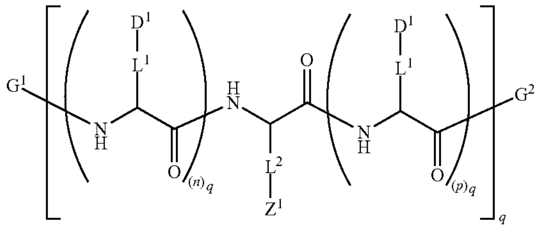

wherein:

each $(n)_q$ and each $(p)_q$ is independently an integer from 1 to 20, wherein for each of the q segments $(n)_q+(p)_q\geq 3$; and q is an integer from 1 to 100.

Clause 34. The multichromophore according to any one of clauses 19, 25-28 and 31-33, wherein the polymeric backbone comprises one or more amino acid sequences selected from the following:

XYXX

XXYXX

XXXYXXX

XXXYXXXX

XXXXYXXX

XXXXYXXXX

XXXXXYXXXXX

XXXXXXYXXXXXX

XXXXXXXYXXXXXXX

XXXXXXXXYXXXXXXXX

XXXXXXXXXYXXXXXXXXX $Y(X)_nY$ $XY(X)_nYX$ $XXY(X)_nYXX$ $XXXY(X)_nYXXX$ $XXXXY(X)_nYXXXX$ $XXXXXY(X)_nYXXXXX$ wherein:

each X is a lysine or ornithine residue covalently N-linked to a pendant donor chromophore group; and each Y is a cysteine residue or a protected cysteine residue.

Clause 35. The multichromophore according to any one of clauses 19, 25 and 26, wherein the multichromophore has the formula:

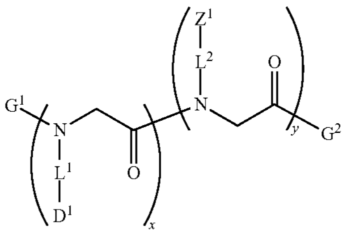

wherein each $D^1$ is independently a pendant donor chromophore group;

each $Z^1$ is independently a chemoselective tag;

each $L^1$ and $L^2$ is independently a linker;

x is 75 mol % or more;

y is 25 mol % or less; and $G^1$ and $G^2$ are each independently selected from a terminal group, a polymer segment, a donor chromophore group, an acceptor fluorophore, a linker and a linked specific binding member.

Clause 36. The multichromophore according to any one of clauses 19-21 and 26, wherein the multichromophore has the formula:

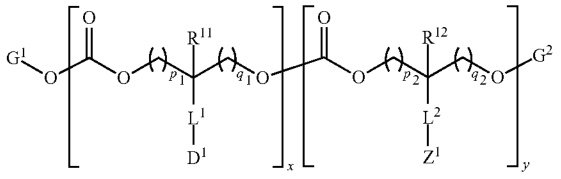

wherein:

each $D^1$ is independently a pendant donor chromophore;

each $Z^1$ is independently a chemoselective tag;

each $L^1$ and $L^2$ is independently a linker;

x is 75 mol % or more;

y is 25 mol % or less; and $G^1$ and $G^2$ are each independently selected from the group consisting of a terminal group, a polymer segment, a donor chromophore group, an acceptor fluorophore, a linker and a linked specific binding member.

Clause 37. The multichromophore according to any one of clauses 16-36, wherein the pendant donor chromophore groups are BODIPY groups.

Clause 38. A polymeric tandem dye comprising:

a light harvesting multichromophore comprising:

a polymeric backbone comprising non-conjugated repeat units; and a plurality of pendant donor chromophore groups each independently linked to a non-conjugated repeat unit of the polymeric backbone; and an acceptor fluorophore linked to a non-conjugated repeat unit of the polymeric backbone and configured in energy-receiving proximity to at least one pendant donor chromophore group of the light harvesting multichromophore.

Clause 39. The polymeric tandem dye according to clause 38, wherein the pendant donor chromophore groups are each substituted with a water soluble group.

Clause 40. The polymeric tandem dye according to clause 38, wherein the polymeric backbone is a linear polymer.

Clause 41. The polymeric tandem dye according to clause 38, wherein the pendant donor chromophore groups are configured in energy-transferring proximity to each other.

Clause 42. The polymeric tandem dye according to clause 36, having a Stokes shift of 100 nm or more.

Clause 43. The polymeric tandem dye according to any one of clauses 36-40, wherein the pendant donor chromophore groups are selected from a fused tricyclic aryl group, a fused tricyclic heteroaryl group, and a BODIPY group.

Clause 44. The polymeric tandem dye according to clause 43, wherein the pendant donor chromophore groups are selected from optionally substituted fluorene, carbazole and silole groups.

Clause 45. The polymeric tandem dye according to any one of clauses 43-44, wherein the pendant donor chromophore groups are fused tricyclic aryl or heteroaryl groups having one of the following formulae:

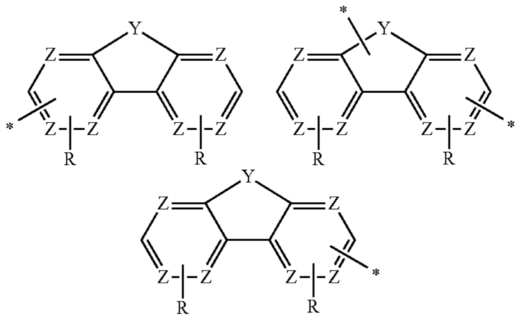

wherein:

* is a point of linkage to a non-conjugated repeat unit of the polymeric backbone;

Y is $C(R^{13})_2$, $—C(R^{13})_2C(R^{13})_2—$, $—C(R^{13})_2Si(R^{13})_2—$, $NR^{13}$, $Si(R^{13})_2$ or Se;

each Z is independently CH, CR or N;

each $R^{13}$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, a WSG and $-L^{11}-Z^1$, wherein $L^{11}$ is a linker and $Z^1$ is a non-conjugated repeat unit, or wherein any two convenient $R^3$ groups are optionally cyclically linked; and each R is independently H or one or more substituents and wherein any two convenient R groups are optionally cyclically linked;

wherein one of R and $R^{13}$ is linked to a non-conjugated repeat unit of the polymeric backbone.

Clause 46. The polymeric tandem dye according to clause 43, wherein the pendant donor chromophore groups are BODIPY groups.

Clause 47. The polymeric tandem dye according to clause 46, wherein the BODIPY groups are described by the formula:

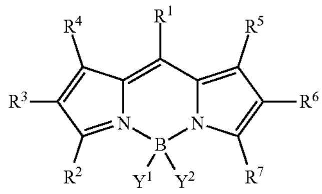

wherein:

$R^1$-$R^7$ are each independently selected from H, alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and $-L^1-Z^1$, or optionally any one or more pairs of substituents selected from $R^6$ and $R^7$, $R^2$ and $R^3$, $R^5$ and $R^6$, $R^3$ and $R^4$, $R^4$ and $R^1$ and $R^5$ and $R^1$, together form a divalent radical and are cyclically linked and together with the carbon atoms to which they are bound provide a 5- or 6-membered fused heterocycle, carbocycle, aryl or heteroaryl ring (e.g., a 5- or 6-membered ring comprising carbon atoms and 0-3 heteroatoms selected from O, S and N), which ring may be unsubstituted or further substituted with a substituent independently selected from alkyl, substituted alkyl, alkoxy, substituted alkoxy, aryl, substituted aryl, heteroaryl, substituted heteroaryl, alkenyl, substituted alkenyl, alkynyl, substituted alkynyl, water solubilizing group (WSG) and $-L^1-Z^1$;

$L^1$ is a linker;

$Z^1$ is a non-conjugated repeat unit of the polymeric backbone; and $Y^1$ and $Y^2$ are independently selected from F, OH, H, cyano, alkyl, substituted alkyl, aryl, substituted aryl, heteroaryl, substituted heteroaryl, alkoxy, substituted alkoxy, alkenyl, substituted alkenyl, alkynyl, substituted alkynyl and WSG;

wherein one of $Y^1$, $Y^2$ and $R^1$-$R^7$ is linked to a non-conjugated repeat unit of the polymeric backbone.

Clause 48. The polymeric tandem dye according to clause 47, wherein $R^1$ is an optionally substituted aryl or heteroaryl linked to a non-conjugated repeat unit of the polymeric backbone.

Clause 49. The polymeric tandem dye according to any one of clauses 47-48, wherein $Y^1$ and $Y^2$ each comprise a water solubilizing group (WSG).

Clause 50. The polymeric tandem dye according to any one of clauses 47-49, wherein the pendant donor chromophore groups are described by the following structure:

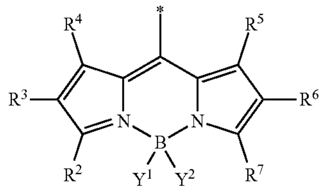

wherein:

* is a point of linkage to a non-conjugated repeat unit of the polymeric backbone;

$Y^1$ and $Y^2$ are each alkynyl substituted with a WSG.

Clause 51. The polymeric tandem dye according to clause 50, wherein the pendant donor chromophore groups are described by the following structure:

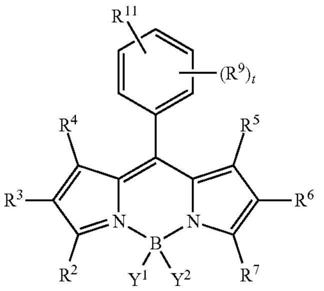

wherein:

$R^{11}$ is $L^1$-$Z^1$ (a linked non-conjugated repeat unit of the polymeric backbone);

each $R^9$ is an optional substituent selected from halogen, hydroxyl, cyano, nitro, alkyl, substituted alkyl, alkoxy, substituted alkoxy, aryl, substituted aryl, heteroaryl and substituted heteroaryl; and t is 0-4.

Clause 52. The polymeric tandem dye according to any one of clauses 38-51, wherein the pendant donor chromophore groups are substituted with one or more water solubilizing groups (WSGs) independently selected from the following formula:

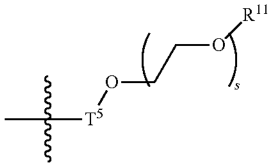

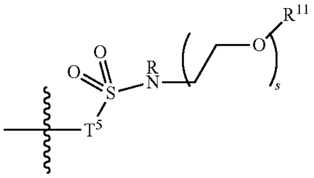

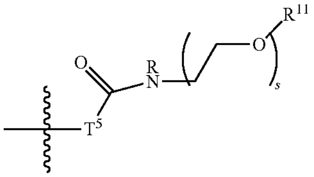

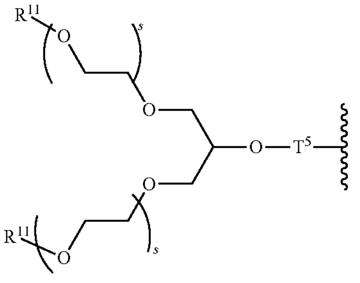

-continued

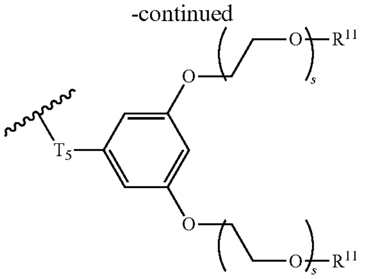

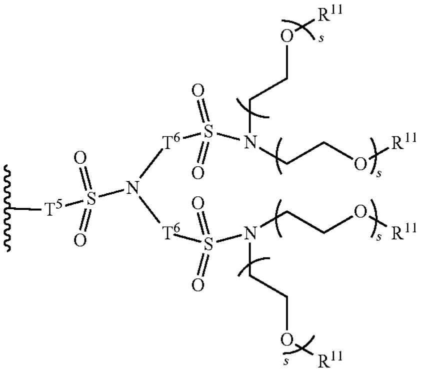

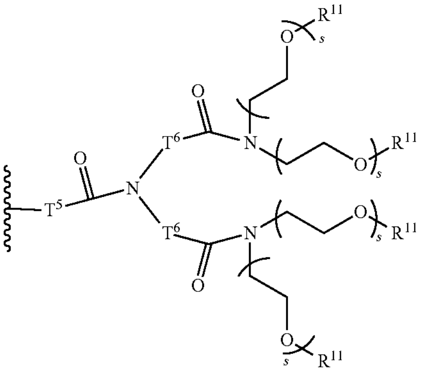

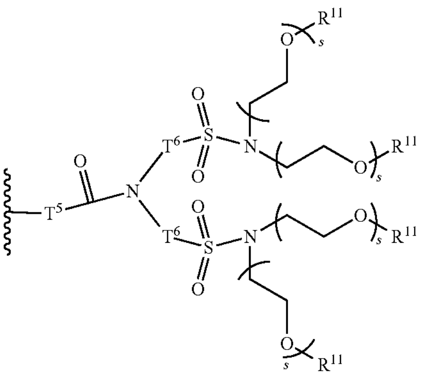

-continued

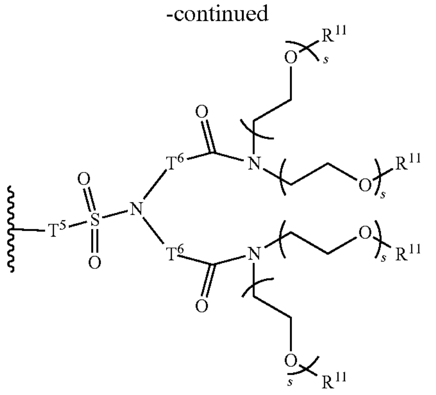

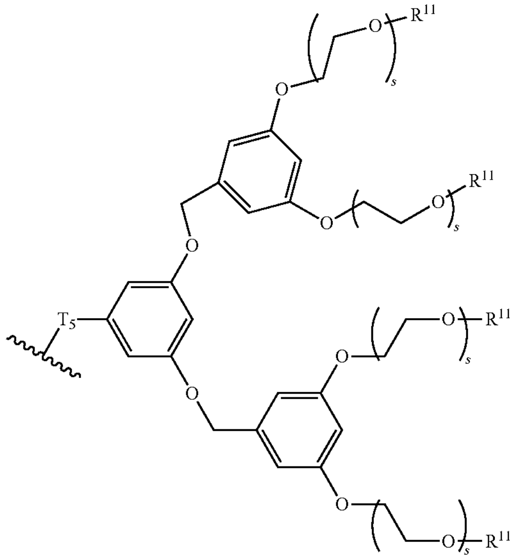

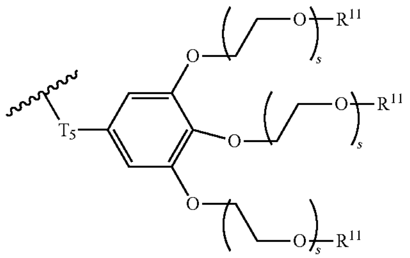

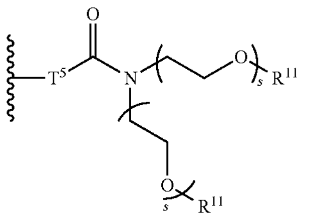

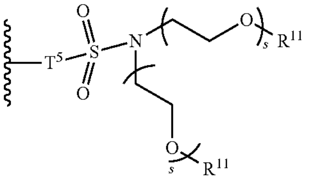

-continued

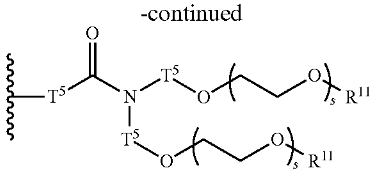

wherein:

$T^5$ is an optional linker;

each $T^6$ is an linker;

$R^{11}$ and R are independently H, alkyl or substituted alkyl; and each s is an integer from 1 to 50.

Clause 53. The polymeric tandem dye according to any one of clauses 38-52, comprising a segment of the formula:

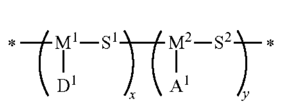

wherein:

each $M^1$ and $M^2$ is independently an aryl or heteroaryl co-monomer;

each $S^1$ and $S^2$ is independently a non-conjugated spacer units;

each $D^1$ is independently a pendant donor chromophore linked to $M^1$;

each $A^1$ is independently an acceptor fluorophore linked to $M^2$;

x is 75 mol % or more; and y is 25 mol % or less.

Clause 54. The polymeric tandem dye according to clause 53, wherein the $M^1$-$S^1$ and $M^2$-$S^2$ repeat units of the polymeric backbone have a random configuration.

Clause 55. The polymeric tandem dye according to any one of clauses 53-54, wherein:

each $M^1$ and $M^2$ independently comprises one or more groups selected from fluorene, carbazole, silole, biphenylene and phenylene; and each $S^1$ and $S^2$ is independently a saturated spacer unit selected from a divalent polyethylene glycol (PEG) and a divalent modified PEG group.

Clause 56. The polymeric tandem dye according to any one of clauses 38-52, comprising a segment of the formula:

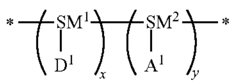

wherein:

the polymeric backbone of non-conjugated repeat units comprises $SM^1$ and $SM^2$ co-monomers that are each independently a non-conjugated co-monomer;

each $D^1$ is independently a pendant donor chromophore linked to $SM^1$;

each $A^1$ is independently an acceptor fluorophore linked to $SM^2$;

x is 75 mol % or more; and y is 25 mol % or less.

Clause 57. The polymeric tandem dye according to clause 56, wherein the repeat units of the polymeric backbone have a random configuration.

Clause 58. The polymeric tandem dye according to any one of clauses 56-57, wherein $SM^1$ and $SM^2$ are co-monomers derived from an acrylate, a methacrylate, an acrylamide, a polystyrene, a ROMP monomer, an ADMET monomer or a cyclic carbonate.

Clause 59. The polymeric tandem dye according to clause 58, wherein $SM^1$ and $SM^2$ are selected from the following formulae:

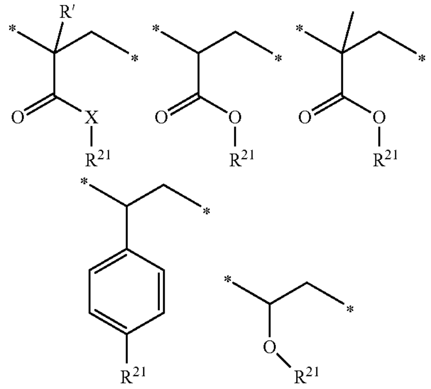

wherein:

$R^{21}$ is $-L^1-D^1$ or $-L^2-Z^1$;

$D^1$ is the pendant donor chromophore linked to $M^1$;

$Z^1$ is a chemoselective tag linked to $M^2$;

$L^1$ and $L^2$ are optional linkers;

X is O or NR";

R' is H or lower alkyl;

R" is H or lower alkyl, substituted lower alkyl and WSG; and

* is a connection to the polymeric backbone.

Clause 60. The polymeric tandem dye according to clause 56, wherein the multichromophore is of formula (XXI):

(XXIa)

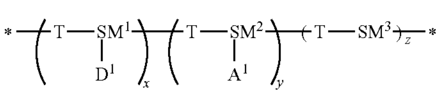

wherein:

the polymeric backbone of non-conjugated repeat units comprises $SM^1$, $SM^2$ and $SM^3$ co-monomers that are each linked via a group T that is the product of a click chemistry or chemoselective group conjugation reaction;

$SM^3$ optionally comprises a linked WSG;

each $D^1$ is independently a pendant light absorbing chromophore linked to $SM^1$;

each $A^1$ is independently an acceptor fluorophore linked to $SM^2$;

x is 50 mol % or more; and y+z is 50 mol % or less, where * is a connection to the polymeric backbone of the multichromophore or a terminal group.

Clause 61. The polymeric tandem dye according to clause 60, wherein $SM^1$, $SM^2$ and $SM^3$ comprise the following structures:

$SM^1$

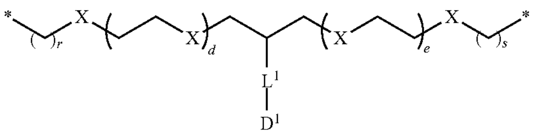

$SM^2$

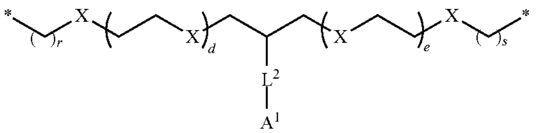

$SM^3$

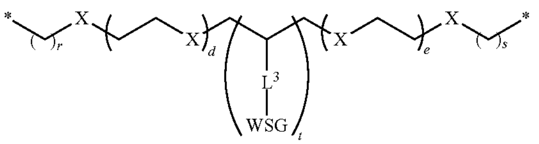

wherein:

each X is independently O or $NR^{31}$ wherein $R^{31}$ is H, alkyl, substituted alkyl, alkanoyl or substituted alkanoyl;

each r and s is independently 1-6 (e.g., 1, 2 or 3);

each d and e is independently 1-12 (e.g., 1-6, such as 1, 2, 3, 4, 5 or 6);

t is 0 or 1;

each $L^1$, $L^2$ and $L^3$ is independently a linker; and

* is a connection to a 1,4-substituted 1,2,3-triazole (T) having one of the following structures:

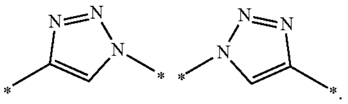

Clause 62. The polymeric tandem dye according to clause 56, wherein the repeat units of the polymeric backbone have a defined linear sequence.

Clause 63. The polymeric tandem dye according to clause 62, wherein $SM^1$ and $SM^2$ are co-monomers derived from amino acids, peptoid monomers, a protected carbonate monomer or a cyclic carbonate monomer.

Clause 64. The polymeric tandem dye according to any one of clauses 56, 62 and 63, wherein the polymeric backbone is a polypeptide having a defined sequence of α-amino acid residues and/or β-amino acid residues.

Clause 65. The polymeric tandem dye according to any one of clauses 56 and 62-64, wherein the multichromophore is of the formula:

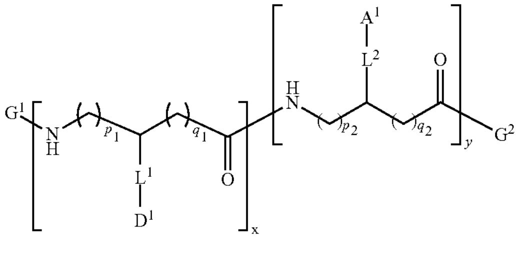

wherein:

each $D^1$ is independently a pendant donor chromophore group;

each $A^1$ is independently an acceptor fluorophore;

each $L^1$ and $L^2$ is independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ and $G^2$ are each independently selected from a terminal group, a polymer segment, a donor chromophore group, an acceptor fluorophore, a linker and a linked specific binding member.

Clause 66. The polymeric tandem dye of clause 65, wherein $p_1$ and $p_2$ are each 0 and $q_1$ and $q_2$ are each 1.

Clause 67. The polymeric tandem dye of clause 65, wherein $p_1$ and $p_2$ are each 1 and $q_1$ and $q_2$ are each 0.

Clause 68. The polymeric tandem dye of clause 65, wherein $p_1$, $p_2$, $q_1$ and $q_2$ are each 0 and the multichromophore is of the formula:

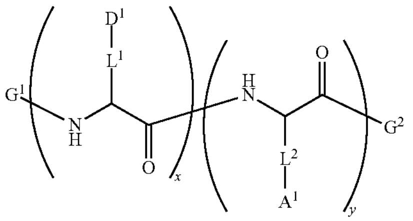

wherein:

each $D^1$ is independently a pendant donor chromophore group;

each $A^1$ is independently an acceptor fluorophore;

$L^1$ and $L^2$ are each independently a linker;

x is 75 mol % or more;

y is 25 mol % or less; and $G^1$ and $G^2$ are each independently selected from a terminal group, a polymer segment, a donor chromophore group, an acceptor fluorophore, a linker and a linked specific binding member.

Clause 69. The polymeric tandem dye according to any one of clauses 64, 65 and 66, comprising a segment of the formula:

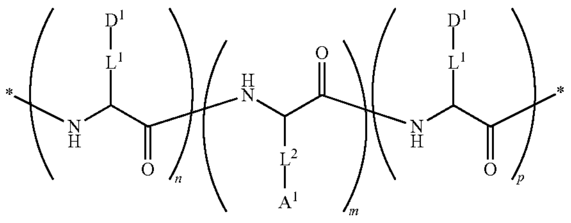

wherein:

each $D^1$ is independently a pendant donor chromophore group;

each $A^1$ is independently an acceptor fluorophore;

each $L^1$ and $L^2$ are independently a linker;

n and p are each independently an integer from 1 to 20 wherein $n+p \geq 2$; and m is 1 or 2.

Clause 70. The polymeric tandem dye according to clause 69, wherein the multichromophore comprises q segments of copolymer and is of the formula:

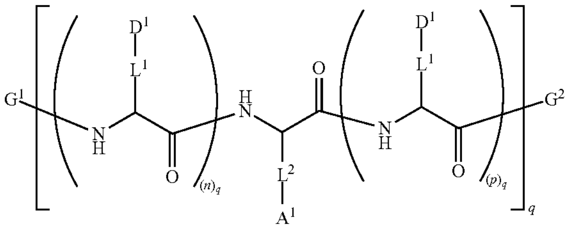

wherein:

each $(n)_q$ and each $(p)_q$ is independently an integer from 1 to 20, wherein for each of the q segments $(n)_q+(p)_q \geq 3$; and q is an integer from 1 to 100.

Clause 71. The polymeric tandem dye according to any one of clauses 56, 62-65 and 68-70, wherein the polymeric backbone comprises an amino acid sequence selected from:

XYXX

XXYXX

XXXYXXX

XXXYXXXX

XXXXYXXX

XXXXYXXXX

XXXXXYXXXXX

XXXXXXYXXXXXX

XXXXXXXYXXXXXXX

XXXXXXXXYXXXXXXXX

XXXXXXXXXYXXXXXXXXX $Y(X)_nY$ $XY(X)_nYX$ $XXY(X)_nYXX$ $XXXY(X)_nYXXX$ $XXXXY(X)_nYXXXX$ $XXXXXY(X)_nYXXXXX$ wherein:

each X is a lysine or ornithine residue covalently N-linked to a pendant donor chromophore group; and each Y is a cysteine residue covalently linked to a pendant acceptor fluorophore group.

Clause 72. The polymeric tandem dye according to any one of clauses 56, 62 and 63, wherein the multichromophore has the formula:

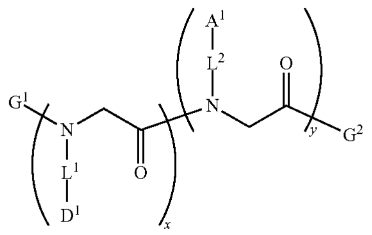

wherein each $D^1$ is independently a pendant donor chromophore group;

each $A^1$ is independently an acceptor chromophore;

each $L^1$ and $L^2$ is independently a linker;

x is 75 mol % or more;

y is 25 mol % or less; and $G^1$ and $G^2$ are each independently selected from a terminal group, a polymer segment, a donor chromophore group, an acceptor fluorophore, a linker and a linked specific binding member.

Clause 73. The polymeric tandem dye according to any one of clauses 56-58 and 63, wherein the multichromophore has the formula:

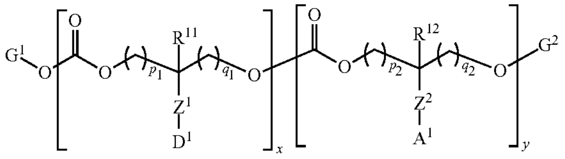

wherein:

each $D^1$ is independently a pendant donor chromophore;

each $A^1$ is independently an acceptor fluorophore;

each $L^1$ and $L^2$ is independently a linker;

x is 75 mol % or more;

y is 25 mol % or less; and $G^1$ and $G^2$ are each independently selected from the group consisting of a terminal group, a polymer segment, a donor chromophore group, an acceptor fluorophore, a linker and a linked specific binding member.

Clause 74. The polymeric tandem dye according to any one of clauses 53-73, wherein the pendant donor chromophore groups are BODIPY groups.

Clause 75. The polymeric tandem dye according to any one of clauses 38-74, wherein the acceptor fluorophore (e.g., each $A^1$) is a small molecule fluorophore.

Clause 76. The polymeric tandem dye according to any one of clauses 38-75, wherein the acceptor fluorophore (e.g., each $A^1$) is selected from a cyanine dye, a rhodamine dye, a xanthene dye, a coumarin dye, a polymethine, a pyrene, a dipyrromethene borondifluoride, a napthalimide, a thiazine dye and an acridine dye.

Clause 77. A labelled specific binding member, comprising:

a polymeric tandem dye comprising:

a light harvesting multichromophore comprising:

a polymeric backbone comprising non-conjugated repeat units; and a plurality of pendant donor chromophore groups each independently linked to a non-conjugated repeat unit of the polymeric backbone; and an acceptor fluorophore linked to a non-conjugated repeat unit of the polymeric backbone and configured in energy-receiving proximity to at least one pendant donor chromophore group of the light harvesting multichromophore; and a specific binding member linked to the polymeric tandem dye.

Clause 78. The labelled specific binding member according to clause 77, wherein the specific binding member is an antibody.

Clause 79. The labelled specific binding member according to clause 77, wherein the specific binding member is an antibody fragment or binding derivative thereof.

Clause 80. The labelled specific binding member according to clause 79, wherein the antibody fragment or binding derivative thereof is selected from the group consisting of a Fab fragment, a $F(ab')_2$ fragment, a scFv, a diabody and a triabody.

Clause 81. The labelled specific binding member according to any one of clauses 77-80, wherein the acceptor fluorophore is selected from a cyanine dye, a rhodamine dye, a xanthene dye, a coumarin dye, a polymethine, a pyrene, a dipyrromethene borondifluoride, a napthalimide, a thiazine dye and an acridine dye.

Clause 82. The labelled specific binding member according to any one of clauses 77-81, wherein the polymeric tandem dye is a dye according to any one of clauses 39-76.

Clause 83. The labelled specific binding member according to any one of clauses 77-81, having the formula:

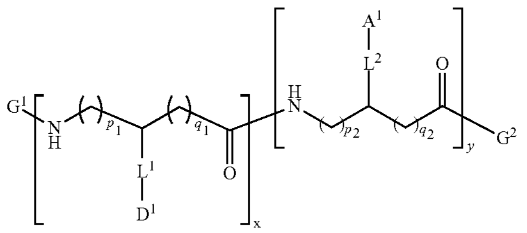

wherein:

each $D^1$ is independently a pendant donor chromophore group;

each $A^1$ is independently an acceptor fluorophore;

each $L^1$ and $L^2$ are independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ is a terminal group, a polymer segment, a donor chromophore group, an acceptor fluorophore, or a linker; and $G^2$ is a linked specific binding member.

Clause 84. The labelled specific binding member according to clause 83, wherein $p_1$, $p_2$, $q_1$ and $q_2$ are each 0 and the multichromophore is of the formula:

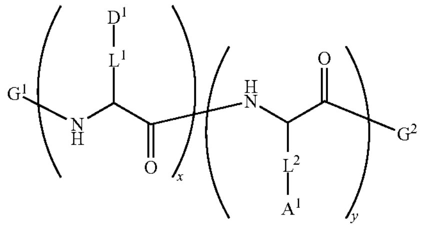

wherein:

each $D^1$ is independently a pendant donor chromophore group;

each $A^1$ is independently an acceptor fluorophore;

$L^1$ and $L^2$ are each independently a linker;

x is 75 mol % or more; y is 25 mol % or less;

$G^1$ is a terminal group, a polymer segment, a donor chromophore group, an acceptor fluorophore or a linker; and $G^2$ is a linked specific binding member.

Clause 85. A method of evaluating a sample for the presence of a target analyte, the method comprising:

(a) contacting the sample with a labelled specific binding member that specifically binds the target analyte to produce a labelling composition contacted sample, wherein the labelled specific binding member comprises:

(i) a polymeric tandem dye according to any one of clauses 38-76; and (ii) a specific binding member linked to the polymeric tandem dye; and (b) assaying the labelling composition contacted sample for the presence of a labelled specific binding member-target analyte binding complex to evaluate whether the target analyte is present in the sample.

Clause 86. The method according to clause 85, wherein the acceptor fluorophore of the polymeric tandem dye is selected from a cyanine dye, a rhodamine dye, a xanthene dye, a coumarin dye, a polymethine, a pyrene, a dipyrromethene borondifluoride, a napthalimide, a thiazine dye and an acridine dye.

Clause 87. The method according to any one of clauses 85-86, further comprising contacting the sample with a second specific binding member that is support bound and specifically binds the target analyte.

Clause 88. The method according to clause 87, wherein the support comprises a magnetic particle.

Clause 89. The method according to any one of clauses 85-88, wherein the target analyte is associated with a cell.

Clause 90. The method according to clause 89, wherein the target analyte is a cell surface marker of the cell.

Clause 91. The method according to clause 90, wherein the cell surface marker is selected from the group consisting of a cell receptor and a cell surface antigen.

Clause 92. The method according to clause 89, wherein the target analyte is an intracellular target, and the method further comprises lysing the cell.

Clause 93. The method according to any one of clauses 85-92, wherein the method further comprises flow cytometrically analyzing the fluorescently labelled target analyte.

Clause 94. A method of labelling a target molecule, the method comprising:

contacting the target molecule with a polymeric tandem dye to produce a labelled target molecule, wherein:

the polymeric tandem dye is a dye according to any one of clauses 38-76 and comprises a conjugation tag that covalently links to the target molecule.

Clause 95. The method according to clause 94, wherein the polymeric tandem dye has the formula:

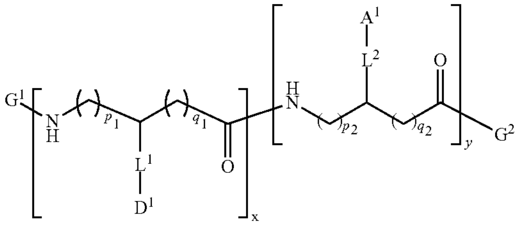

wherein:

each $D^1$ is independently a pendant donor chromophore group;

each $A^1$ is independently an acceptor fluorophore;

each $L^1$ and $L^2$ are independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ is a terminal group, a polymer segment, a donor chromophore group, an acceptor fluorophore or a linker; and $G^2$ is a linker comprising the conjugation tag.

Clause 96. A method of preparing a light harvesting multichromophore, the method comprising:

a) synthesizing a protected polypeptide having a defined amino acid sequence consisting of blocks of first amino acid residues separated by single occurrences of second amino acid residues, wherein:

each block of first amino acid residues comprises at least two residues;

the first amino acid residues each comprise a protected first chemoselective sidechain group; and the second amino acid residues each comprise a protected second chemoselective sidechain group;

b) deprotecting the protected polypeptide to produce a deprotected polypeptide wherein the first and second chemoselective sidechain groups are deprotected;

c) coupling reactive donor chromophore moieties to deprotected first chemoselective sidechain groups of the first amino acid residues to produce pendant donor chromophore groups.

Clause 97. The method according to clause 96, further comprising, sequentially with step c), coupling reactive acceptor fluorophore moieties to deprotected second chemoselective sidechain groups of the second amino acid residues to produce pendant acceptor fluorophores.

Clause 98. The method according to clause 96, further comprising, after step a), deprotecting the N-terminal of the protected polypeptide and coupling a G1 group to the N-terminal of the N-terminal deprotected polypeptide, wherein G1 is a terminal group (e.g., capping group), a donor chromophore group or a linker.

Clause 99. The method according to any one of clauses 96-98, further comprising, after step c), coupling a specific binding member to the C-terminal of the polypeptide.

Clause 100. The method according to any one of clauses 96-99, wherein the light harvesting multichromophore is of the formula:

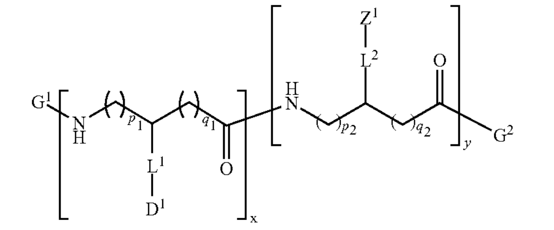

wherein:

$D^1$ is the pendant donor chromophore group;

$Z^1$ is the second chemoselective sidechain group;

each $L^1$ and $L^2$ is independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ and $G^2$ are each independently selected from a terminal group, a polymer segment, a donor chromophore group, an acceptor fluorophore, a linker and a linked specific binding member.

Clause 101. The method according to any one of clauses 96-100, wherein the light harvesting multichromophore is of the formula:

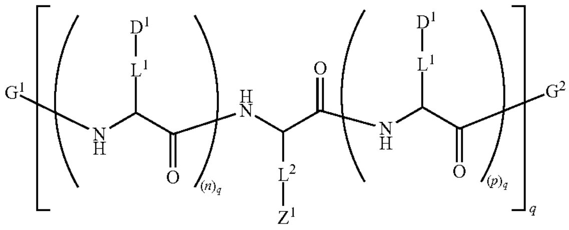

wherein:

each $(n)_q$ and each $(p)_q$ is independently an integer from 1 to 20, wherein for each of the q segments $(n)_q+(p)_q \geq 3$; and q is an integer from 1 to 100.

Clause 102. The method according to any one of clauses 96-101, wherein:

the first amino acid residues are independently selected from lysine and ornithine; and the second amino acid residues are each cysteine.

Clause 103. The method according to any one of clauses 96-102, wherein the defined amino acid sequence comprises an amino acid sequence selected from:

XYXX

XXYXX

XXXYXXX

XXXYXXXX

XXXXYXXX

XXXXYXXXX

XXXXXYXXXXX

XXXXXXYXXXXXX

-continued

XXXXXXXYXXXXXXX

XXXXXXXXYXXXXXXXX

XXXXXXXXXYXXXXXXXXX $Y(X)_nY$ $XY(X)_nYX$ $XXY(X)_nYXX$ $XXXY(X)_nYXXX$ $XXXXY(X)_nYXXXX$ $XXXXXY(X)_nYXXXXX$ wherein:

each X is a lysine or ornithine residue covalently N-inked to a pendant donor chromophore group; and each Y is a cysteine residue or a protected cysteine residue.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A method comprising contacting a sample with a polymeric tandem dye comprising:

a polymeric backbone comprising non-conjugated repeat units;

a pendant donor chromophore independently linked to a non-conjugated repeat unit of the polymeric backbone;

an acceptor fluorophore linked to a non-conjugated repeat unit of the polymeric backbone and configured in energy-receiving proximity to the donor chromophore; and a specific binding member conjugated to the polymeric backbone.

2. The method according to claim 1, wherein the polymeric backbone comprises from 2 to 200 non-conjugated repeat units.

3. The method according to claim 2, wherein the polymeric backbone comprises from 4 to 100 non-conjugated repeat units.

4. The method according to claim 1, wherein the non-conjugated repeat units are selected from the group consisting of amino acids, peptoid monomers, protected carbonate monomers and cyclic carbonate monomers, and combinations thereof.

5. The method according to claim 1, wherein the tandem dye comprises a plurality of pendant donor chromophores each independently linked to a non-conjugated repeat unit of the polymeric backbone.

6. The method according to claim 1, wherein the donor chromophore is selected from a fused tricyclic aryl or heteroaryl group and a BODIPY group.

7. The method according to claim 6, wherein the donor chromophore is a BODIPY group.

8. The method according to claim 1, wherein the acceptor fluorophore is selected from a cyanine dye, a rhodamine dye, a xanthene dye, a coumarin dye, a polymethine, a pyrene, a dipyrromethene borondifluoride, a napthalimide, a thiazine dye and an acridine dye.

9. The method according to claim 1, wherein the number of donor chromophores is greater than the number of acceptor fluorophores.

10. The method according to claim 9, wherein the ratio of donor chromophores to acceptor fluorophores ranges from 5:1 to 10:1.

11. The method according to claim 9, wherein the polymeric backbone comprises 50 mol % or more non-conjugated repeat units that are independently linked to a donor chromophore.

12. The method according to claim 1, wherein method comprises assaying the sample for a target analyte to which the specific binding member binds.

13. The method according to claim 1, wherein the specific binding member is an antibody, an antibody fragment or binding derivative thereof.

14. The method according claim 13, wherein the analyte is associated with a cell.

15. The method according to claim 14, wherein the analyte is a cell surface marker of the cell.

16. The method according to claim 15, wherein the cell surface marker is selected from the group consisting of a cell receptor and a cell surface antigen.

17. The method according to claim 14, wherein the analyte is an intracellular target.

18. The method according to claim 17, wherein the method comprises lysing permeabilizing or lysing the cell.

19. The method according to claim 1, wherein the method comprises flow cytometrically analyzing the sample.

* * * * *

SEQUENCE LISTING

```
Sequence total quantity: 42
SEQ ID NO: 1            moltype = AA  length = 4
FEATURE                 Location/Qualifiers
source                  1..4
                        mol_type = protein
                        organism = synthetic construct
SITE                    1
                        note = wherein the K residue may be protected or covalently
                         linked via the sidechain amino group to a pendant donor
                         chromophore group
SITE                    3..4
                        note = wherein the K residue may be protected or covalently
                         linked via the sidechain amino group to a pendant donor
                         chromophore group
SITE                    2
                        note = wherein the C residue may be protected
SEQUENCE: 1
KCKK                                                                        4

SEQ ID NO: 2            moltype = AA  length = 4
FEATURE                 Location/Qualifiers
source                  1..4
                        mol_type = protein
                        organism = synthetic construct
SITE                    1..2
                        note = wherein the K residue may be protected or covalently
                         linked via the sidechain amino group to a pendant donor
                         chromophore group
SITE                    3
                        note = wherein the C residue may be protected
SITE                    4
                        note = wherein the K residue may be protected or covalently
                         linked via the sidechain amino group to a pendant donor
                         chromophore group
SEQUENCE: 2
KKCK                                                                        4

SEQ ID NO: 3            moltype = AA  length = 5
FEATURE                 Location/Qualifiers
source                  1..5
                        mol_type = protein
                        organism = synthetic construct
SITE                    1..2
                        note = wherein the K residue may be protected or covalently
                         linked via the sidechain amino group to a pendant donor
                         chromophore group
SITE                    4..5
                        note = wherein the K residue may be protected or covalently
                         linked via the sidechain amino group to a pendant donor
                         chromophore group
SEQUENCE: 3
KKYKK                                                                       5

SEQ ID NO: 4            moltype = AA  length = 6
FEATURE                 Location/Qualifiers
source                  1..6
                        mol_type = protein
                        organism = synthetic construct
SITE                    1..3
                        note = wherein the K residue may be protected or covalently
                         linked via the sidechain amino group to a pendant donor
                         chromophore group
SITE                    5..6
                        note = wherein the K residue may be protected or covalently
                         linked via the sidechain amino group to a pendant donor
                         chromophore group
SEQUENCE: 4
KKKYKK                                                                      6

SEQ ID NO: 5            moltype = AA  length = 6
FEATURE                 Location/Qualifiers
source                  1..6
                        mol_type = protein
                        organism = synthetic construct
SITE                    1..2
                        note = wherein the K residue may be protected or covalently
                         linked via the sidechain amino group to a pendant donor
                         chromophore group
```

```
SITE                    4..6
                        note = wherein the K residue may be protected or covalently
                         linked via the sidechain amino group to a pendant donor
                         chromophore group
SEQUENCE: 5
KKYKKK                                                                  6

SEQ ID NO: 6            moltype = AA  length = 7
FEATURE                 Location/Qualifiers
source                  1..7
                        mol_type = protein
                        organism = synthetic construct
SITE                    1..3
                        note = wherein the K residue may be protected or covalently
                         linked via the sidechain amino group to a pendant donor
                         chromophore group
SITE                    5..7
                        note = wherein the K residue may be protected or covalently
                         linked via the sidechain amino group to a pendant donor
                         chromophore group
SEQUENCE: 6
KKKYKKK                                                                 7

SEQ ID NO: 7            moltype = AA  length = 8
FEATURE                 Location/Qualifiers
source                  1..8
                        mol_type = protein
                        organism = synthetic construct
SITE                    1..3
                        note = wherein the K residue may be protected or covalently
                         linked via the sidechain amino group to a pendant donor
                         chromophore group
SITE                    5..8
                        note = wherein the K residue may be protected or covalently
                         linked via the sidechain amino group to a pendant donor
                         chromophore group
SEQUENCE: 7
KKKYKKKK                                                                8

SEQ ID NO: 8            moltype = AA  length = 8
FEATURE                 Location/Qualifiers
source                  1..8
                        mol_type = protein
                        organism = synthetic construct
SITE                    1..4
                        note = wherein the K residue may be protected or covalently
                         linked via the sidechain amino group to a pendant donor
                         chromophore group
SITE                    6..8
                        note = wherein the K residue may be protected or covalently
                         linked via the sidechain amino group to a pendant donor
                         chromophore group
SEQUENCE: 8
KKKKYKKK                                                                8

SEQ ID NO: 9            moltype = AA  length = 9
FEATURE                 Location/Qualifiers
source                  1..9
                        mol_type = protein
                        organism = synthetic construct
SITE                    1..4
                        note = wherein the K residue may be protected or covalently
                         linked via the sidechain amino group to a pendant donor
                         chromophore group
SITE                    5
                        note = wherein the C residue may be protected
SITE                    6..9
                        note = wherein the K residue may be protected or covalently
                         linked via the sidechain amino group to a pendant donor
                         chromophore group
SEQUENCE: 9
KKKKCKKKK                                                               9

SEQ ID NO: 10           moltype = AA  length = 11
FEATURE                 Location/Qualifiers
source                  1..11
                        mol_type = protein
                        organism = synthetic construct
SITE                    1..5
```

```
                        note = wherein the K residue may be protected or covalently
                         linked via the sidechain amino group to a pendant donor
                         chromophore group
SITE                    6
                        note = wherein the C residue may be protected
SITE                    7..11
                        note = wherein the K residue may be protected or covalently
                         linked via the sidechain amino group to a pendant donor
                         chromophore group
SEQUENCE: 10
KKKKKCKKKK K                                                          11

SEQ ID NO: 11           moltype = AA  length = 13
FEATURE                 Location/Qualifiers
source                  1..13
                        mol_type = protein
                        organism = synthetic construct
SITE                    1..6
                        note = wherein the K residue may be protected or covalently
                         linked via the sidechain amino group to a pendant donor
                         chromophore group
SITE                    7
                        note = wherein the C residue may be protected
SITE                    8..13
                        note = wherein the K residue may be protected or covalently
                         linked via the sidechain amino group to a pendant donor
                         chromophore group
SEQUENCE: 11
KKKKKKCKKK KKK                                                        13

SEQ ID NO: 12           moltype = AA  length = 15
FEATURE                 Location/Qualifiers
source                  1..15
                        mol_type = protein
                        organism = synthetic construct
SITE                    1..7
                        note = wherein the K residue may be protected or covalently
                         linked via the sidechain amino group to a pendant donor
                         chromophore group
SITE                    8
                        note = wherein the C residue may be protected
SITE                    9..15
                        note = wherein the K residue may be protected or covalently
                         linked via the sidechain amino group to a pendant donor
                         chromophore group
SEQUENCE: 12
KKKKKKKCKK KKKKK                                                      15

SEQ ID NO: 13           moltype = AA  length = 17
FEATURE                 Location/Qualifiers
source                  1..17
                        mol_type = protein
                        organism = synthetic construct
SITE                    1..8
                        note = wherein the K residue may be protected or covalently
                         linked via the sidechain amino group to a pendant donor
                         chromophore group
SITE                    9
                        note = wherein the C residue may be protected
SITE                    10..17
                        note = wherein the K residue may be protected or covalently
                         linked via the sidechain amino group to a pendant donor
                         chromophore group
SEQUENCE: 13
KKKKKKKKCK KKKKKKK                                                    17

SEQ ID NO: 14           moltype = AA  length = 19
FEATURE                 Location/Qualifiers
source                  1..19
                        mol_type = protein
                        organism = synthetic construct
SITE                    1..9
                        note = wherein the K residue may be protected or covalently
                         linked via the sidechain amino group to a pendant donor
                         chromophore group
SITE                    10
                        note = wherein the C residue may be protected
SITE                    11..19
                        note = wherein the K residue may be protected or covalently
```

```
                       linked via the sidechain amino group to a pendant donor
                       chromophore group
SEQUENCE: 14
KKKKKKKKKC KKKKKKKKK                                                 19

SEQ ID NO: 15          moltype = AA  length = 21
FEATURE                Location/Qualifiers
source                 1..21
                       mol_type = protein
                       organism = synthetic construct
SITE                   1..4
                       note = wherein the K residue may be protected or covalently
                        linked via the sidechain amino group to a pendant donor
                        chromophore group
SITE                   5
                       note = wherein the C residue may be protected
SITE                   6..15
                       note = wherein the K residue may be protected or covalently
                        linked via the sidechain amino group to a pendant donor
                        chromophore group
SITE                   16
                       note = wherein the C residue may be protected
SITE                   17..21
                       note = wherein the K residue may be protected or covalently
                        linked via the sidechain amino group to a pendant donor
                        chromophore group
SEQUENCE: 15
KKKKCKKKKK KKKKKCKKKK K                                              21

SEQ ID NO: 16          moltype = AA  length = 22
FEATURE                Location/Qualifiers
source                 1..22
                       mol_type = protein
                       organism = synthetic construct
VARIANT                2..21
                       note = wherein up to 18 copies of K may be removed
SITE                   1
                       note = wherein the C residue may be protected
SITE                   2..21
                       note = wherein the K residue may be protected or covalently
                        linked via the sidechain amino group to a pendant donor
                        chromophore group
SITE                   22
                       note = wherein the C residue may be protected
SEQUENCE: 16
CKKKKKKKKK KKKKKKKKKK KC                                             22

SEQ ID NO: 17          moltype = AA  length = 24
FEATURE                Location/Qualifiers
source                 1..24
                       mol_type = protein
                       organism = synthetic construct
VARIANT                3..22
                       note = wherein up to 18 copies of K may be removed
SITE                   1
                       note = wherein the K residue may be protected or covalently
                        linked via the sidechain amino group to a pendant donor
                        chromophore group
SITE                   2
                       note = wherein the C residue may be protected
SITE                   3..22
                       note = wherein the K residue may be protected or covalently
                        linked via the sidechain amino group to a pendant donor
                        chromophore group
SITE                   23
                       note = wherein the C residue may be protected
SITE                   24
                       note = wherein the K residue may be protected or covalently
                        linked via the sidechain amino group to a pendant donor
                        chromophore group
SEQUENCE: 17
KCKKKKKKKK KKKKKKKKKK KKCK                                           24

SEQ ID NO: 18          moltype = AA  length = 26
FEATURE                Location/Qualifiers
source                 1..26
                       mol_type = protein
                       organism = synthetic construct
VARIANT                4..23
```

-continued

```
                        note = wherein up to 18 copies of K may be removed
SITE                    1..2
                        note = wherein the K residue may be protected or covalently
                         linked via the sidechain amino group to a pendant donor
                         chromophore group
SITE                    3
                        note = wherein the C residue may be protected
SITE                    4..23
                        note = wherein the K residue may be protected or covalently
                         linked via the sidechain amino group to a pendant donor
                         chromophore group
SITE                    24
                        note = wherein the C residue may be protected
SITE                    25..26
                        note = wherein the K residue may be protected or covalently
                         linked via the sidechain amino group to a pendant donor
                         chromophore group
SEQUENCE: 18
KKCKKKKKKK KKKKKKKKKK KKKCKK                                        26

SEQ ID NO: 19           moltype = AA  length = 28
FEATURE                 Location/Qualifiers
source                  1..28
                        mol_type = protein
                        organism = synthetic construct
SITE                    1..3
                        note = wherein the K residue may be protected or covalently
                         linked via the sidechain amino group to a pendant donor
                         chromophore group
SITE                    4
                        note = wherein the C residue may be protected
VARIANT                 5..24
                        note = wherein up to 18 copies of K may be removed
SITE                    5..24
                        note = wherein the K residue may be protected or covalently
                         linked via the sidechain amino group to a pendant donor
                         chromophore group
SITE                    25
                        note = wherein the C residue may be protected
SITE                    26..28
                        note = wherein the K residue may be protected or covalently
                         linked via the sidechain amino group to a pendant donor
                         chromophore group
SEQUENCE: 19
KKKCKKKKKK KKKKKKKKKK KKKKCKKK                                      28

SEQ ID NO: 20           moltype = AA  length = 30
FEATURE                 Location/Qualifiers
source                  1..30
                        mol_type = protein
                        organism = synthetic construct
SITE                    1..4
                        note = wherein the K residue may be protected or covalently
                         linked via the sidechain amino group to a pendant donor
                         chromophore group
SITE                    5
                        note = wherein the C residue may be protected
VARIANT                 6..25
                        note = wherein up to 18 copies of K may be removed
SITE                    6..25
                        note = wherein the K residue may be protected or covalently
                         linked via the sidechain amino group to a pendant donor
                         chromophore group
SITE                    26
                        note = wherein the C residue may be protected
SITE                    27..30
                        note = wherein the K residue may be protected or covalently
                         linked via the sidechain amino group to a pendant donor
                         chromophore group
SEQUENCE: 20
KKKKCKKKKK KKKKKKKKKK KKKKKCKKKK                                    30

SEQ ID NO: 21           moltype = AA  length = 32
FEATURE                 Location/Qualifiers
source                  1..32
                        mol_type = protein
                        organism = synthetic construct
SITE                    1..5
                        note = wherein the K residue may be protected or covalently
```

-continued

```
                         linked via the sidechain amino group to a pendant donor
                         chromophore group
SITE                    6
                        note = wherein the C residue may be protected
SITE                    7..26
                        note = wherein the K residue may be protected or covalently
                         linked via the sidechain amino group to a pendant donor
                         chromophore group
VARIANT                 7..26
                        note = wherein up to 18 copies of K may be removed
SITE                    27
                        note = wherein the C residue may be protected
SITE                    28..32
                        note = wherein the K residue may be protected or covalently
                         linked via the sidechain amino group to a pendant donor
                         chromophore group
SEQUENCE: 21
KKKKKCKKKK KKKKKKKKKK KKKKKKCKKK KK                                32

SEQ ID NO: 22           moltype =   length =
SEQUENCE: 22
000

SEQ ID NO: 23           moltype =   length =
SEQUENCE: 23
000

SEQ ID NO: 24           moltype =   length =
SEQUENCE: 24
000

SEQ ID NO: 25           moltype =   length =
SEQUENCE: 25
000

SEQ ID NO: 26           moltype =   length =
SEQUENCE: 26
000

SEQ ID NO: 27           moltype =   length =
SEQUENCE: 27
000

SEQ ID NO: 28           moltype =   length =
SEQUENCE: 28
000

SEQ ID NO: 29           moltype =   length =
SEQUENCE: 29
000

SEQ ID NO: 30           moltype =   length =
SEQUENCE: 30
000

SEQ ID NO: 31           moltype =   length =
SEQUENCE: 31
000

SEQ ID NO: 32           moltype =   length =
SEQUENCE: 32
000

SEQ ID NO: 33           moltype =   length =
SEQUENCE: 33
000

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000
```

-continued

```
SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000
```